US010827753B2

(12) United States Patent
Williams et al.

(10) Patent No.: US 10,827,753 B2
(45) Date of Patent: *Nov. 10, 2020

(54) COMPOSITIONS AND METHODS FOR CONTROLLING NEMATODES

(71) Applicant: Monsanto Technology LLC, St. Louis, MO (US)

(72) Inventors: Deryck J. Williams, University City, MO (US); Matt W. Dimmic, Maryland Heights, MO (US); William P. Haakenson, St. Louis, MO (US); Al Wideman, St. Louis, MO (US); Barry J. Shortt, New Melle, MO (US); Tim Cheeseright, Hertfordshire (GB); Michael J. Crawford, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/507,535

(22) Filed: Jul. 10, 2019

(65) Prior Publication Data

US 2019/0343120 A1    Nov. 14, 2019

Related U.S. Application Data

(60) Continuation of application No. 16/137,641, filed on Sep. 21, 2018, now Pat. No. 10,375,958, which is a division of application No. 15/415,170, filed on Jan. 25, 2017, now Pat. No. 10,112,930, which is a division of application No. 14/790,726, filed on Jul. 2, 2015, now Pat. No. 9,642,364, which is a continuation of application No. 13/856,236, filed on Apr. 3, 2013, now Pat. No. 9,125,410, which is a division of application No. 12/190,989, filed on Aug. 13, 2008, now Pat. No. 8,435,999.

(60) Provisional application No. 60/955,448, filed on Aug. 13, 2007.

(51) Int. Cl.
| | | |
|---|---|---|
| *C07D 405/04* | (2006.01) | |
| *C07D 417/04* | (2006.01) | |
| *C07D 413/04* | (2006.01) | |
| *A01N 43/22* | (2006.01) | |
| *A01N 57/28* | (2006.01) | |
| *A01N 57/32* | (2006.01) | |
| *A01N 43/76* | (2006.01) | |
| *A01N 43/82* | (2006.01) | |
| *A01N 47/12* | (2006.01) | |
| *A01N 57/30* | (2006.01) | |
| *A01N 43/56* | (2006.01) | |
| *A01N 43/78* | (2006.01) | |
| *C07D 413/14* | (2006.01) | |

(52) U.S. Cl.
CPC ............ *A01N 43/22* (2013.01); *A01N 43/56* (2013.01); *A01N 43/76* (2013.01); *A01N 43/78* (2013.01); *A01N 43/82* (2013.01); *A01N 47/12* (2013.01); *A01N 57/28* (2013.01); *A01N 57/30* (2013.01); *A01N 57/32* (2013.01); *C07D 405/04* (2013.01); *C07D 413/04* (2013.01); *C07D 413/14* (2013.01); *C07D 417/04* (2013.01)

(58) Field of Classification Search
CPC ... C07D 405/04; C07D 413/04; C07D 417/04
See application file for complete search history.

(56) References Cited

U.S. PATENT DOCUMENTS

| | | |
|---|---|---|
| 3,192,103 A | 6/1965 | Sousa et al. |
| 3,211,742 A | 10/1965 | Lenaers |
| 3,218,331 A | 11/1965 | Eloy |
| 3,227,725 A | 1/1966 | Eloy et al. |
| 3,264,318 A | 8/1966 | Eloy |
| 3,270,029 A | 8/1966 | Palazzo |
| 3,509,153 A | 4/1970 | Hayao et al. |
| 3,770,754 A | 11/1973 | Parsons |
| 3,853,893 A | 12/1974 | Narayanan et al. |
| 3,910,940 A | 10/1975 | Narayanan et al. |
| 3,910,942 A | 10/1975 | Narayanan et al. |
| 4,465,017 A | 8/1984 | Simmons |
| 4,759,945 A | 7/1988 | Nemecek et al. |
| 4,791,124 A | 12/1988 | Lutomski et al. |
| 4,871,753 A | 10/1989 | Rohr |
| 4,908,357 A | 3/1990 | Lutomski |
| 4,943,583 A | 7/1990 | Lüthy |
| 5,080,925 A | 1/1992 | Kouno |
| 5,107,787 A | 4/1992 | Kouno |
| 5,342,851 A | 8/1994 | Sanfilippo et al. |
| 5,389,399 A | 2/1995 | Bazin et al. |
| 5,554,445 A | 9/1996 | Struszczyk et al. |
| 5,633,271 A | 5/1997 | Amoo et al. |
| 5,891,246 A | 4/1999 | Lund |

(Continued)

FOREIGN PATENT DOCUMENTS

| | | |
|---|---|---|
| AU | 2004200420 A1 | 9/2004 |
| CA | 2361816 A1 | 8/2000 |

(Continued)

OTHER PUBLICATIONS

U.S. Appl. No. 12/190,989.
U.S. Appl. No. 13/856,236.
U.S. Appl. No. 14/567,694.
U.S. Appl. No. 14/790,726.
U.S. Appl. No. 15/415,170.
U.S. Appl. No. 16/137,641.
U.S. Appl. No. 12/703,750.
U.S. Appl. No. 12/904,724.
U.S. Appl. No. 13/763,087.

(Continued)

*Primary Examiner* — Shawquia Jackson
(74) *Attorney, Agent, or Firm* — Stinson LLP; Lawrence M. Lavin, Jr.

(57) ABSTRACT

Compositions and methods for controlling nematodes are described herein, e.g., nematodes that infest plants or animals. The compounds include oxazoles, oxadiazoles and thiadiazoles.

25 Claims, 7 Drawing Sheets

(56) References Cited

U.S. PATENT DOCUMENTS

| | | |
|---|---|---|
| 5,912,243 A | 6/1999 | Dowling et al. |
| 5,918,413 A | 7/1999 | Otani et al. |
| 5,985,904 A | 11/1999 | Jeschke et al. |
| 6,001,829 A | 12/1999 | Krämer et al. |
| 6,048,714 A | 4/2000 | Hiromoto |
| 6,107,458 A | 8/2000 | Ohki et al. |
| 6,232,290 B1 | 5/2001 | Ohki et al. |
| 6,265,536 B1 | 7/2001 | Ohki et al. |
| 6,310,049 B1 | 10/2001 | Wada et al. |
| 6,743,776 B2 | 6/2004 | Ohki et al. |
| 6,939,831 B1 | 9/2005 | Caminade et al. |
| 6,992,096 B2 | 1/2006 | Karp et al. |
| 7,041,685 B2 | 5/2006 | Cai et al. |
| 7,144,876 B2 | 12/2006 | Cai et al. |
| 7,202,262 B2 | 4/2007 | Karp et al. |
| 7,304,080 B2 | 12/2007 | Karp et al. |
| 7,317,029 B2 | 1/2008 | Cai et al. |
| 7,419,991 B2 | 9/2008 | Karp et al. |
| 7,683,082 B2 | 3/2010 | Karp et al. |
| 7,772,259 B2 | 8/2010 | Karp et al. |
| 7,834,039 B2 | 11/2010 | Hobson et al. |
| 8,017,555 B2 | 9/2011 | Slomczynska et al. |
| 8,017,631 B2 | 9/2011 | Dahl et al. |
| 8,017,636 B2 | 9/2011 | Karp et al. |
| 8,063,041 B2 | 11/2011 | Andreella et al. |
| 8,129,540 B2 | 3/2012 | Karp et al. |
| 8,163,782 B2 | 4/2012 | Karp et al. |
| 8,163,930 B2 | 4/2012 | Cohen et al. |
| 8,227,494 B2 | 7/2012 | Karp et al. |
| 8,318,776 B2 | 11/2012 | Mizuno |
| 9,051,309 B2 | 6/2015 | Slomczynska et al. |
| 9,125,410 B2 | 9/2015 | Williams et al. |
| 9,642,364 B2 | 5/2017 | Williams et al. |
| 9,961,899 B2 | 5/2018 | Ding et al. |
| 10,112,930 B2 | 10/2018 | Williams et al. |
| 10,117,434 B2 | 11/2018 | Ding et al. |
| 2002/0013326 A1 | 1/2002 | Tiebes et al. |
| 2002/0132813 A1 | 9/2002 | Schaper et al. |
| 2003/0045546 A1 | 3/2003 | Cai et al. |
| 2003/0055085 A1 | 3/2003 | Wagenen et al. |
| 2003/0162812 A1 | 8/2003 | Harmsen et al. |
| 2004/0127521 A1 | 7/2004 | Cai et al. |
| 2004/0204461 A1 | 10/2004 | Karp et al. |
| 2004/0248950 A1 | 12/2004 | Ishizuka et al. |
| 2005/0004005 A1 | 1/2005 | Kasibhatla et al. |
| 2005/0075375 A1 | 4/2005 | Vourloumis et al. |
| 2005/0176796 A1 | 8/2005 | D'Alessio et al. |
| 2006/0166898 A1 | 7/2006 | Chen |
| 2007/0123425 A1 | 5/2007 | Frisch et al. |
| 2008/0015193 A1 | 1/2008 | Mendoza et al. |
| 2009/0012031 A1 | 1/2009 | Chinnaiyan et al. |
| 2009/0048311 A1 | 2/2009 | Williams et al. |
| 2009/0054234 A1 | 2/2009 | Long |
| 2009/0170842 A1 | 7/2009 | Jensen et al. |
| 2010/0210849 A1 | 8/2010 | Slomczynska et al. |
| 2011/0028320 A1 | 2/2011 | Slomcynska et al. |
| 2011/0257010 A1 | 10/2011 | Koltzenburg et al. |
| 2012/0157314 A1 | 6/2012 | Ahrens et al. |
| 2013/0303368 A1 | 11/2013 | Slomczynska et al. |
| 2014/0039197 A1 | 2/2014 | Miller et al. |
| 2014/0187419 A1 | 7/2014 | Ding et al. |
| 2019/0021325 A1 | 1/2019 | Williams et al. |

FOREIGN PATENT DOCUMENTS

| | | |
|---|---|---|
| CA | 2699980 A1 | 2/2009 |
| DE | 19923317 A1 | 11/2000 |
| EP | 0410551 A1 | 1/1991 |
| EP | 0339854 B1 | 5/1993 |
| EP | 1419770 A1 | 5/2004 |
| EP | 1574505 A1 | 9/2005 |
| EP | 1790229 A1 | 5/2007 |
| EP | 1881979 B1 | 8/2010 |
| EP | 2254572 A2 | 12/2010 |
| JP | S47-27025 B | 7/1972 |
| JP | 5-51318 | 3/1993 |
| JP | 2001-505880 A | 5/2001 |
| JP | 2001-316378 A | 11/2001 |
| JP | 2001-522377 A | 11/2001 |
| JP | 2002-234843 A | 8/2002 |
| JP | 2002-308860 | 10/2002 |
| JP | 2002-536365 A | 10/2002 |
| JP | 2003-81832 A | 3/2003 |
| JP | 2005-162612 A | 6/2005 |
| JP | 2005-529850 | 10/2005 |
| JP | 2006-107615 A | 4/2006 |
| JP | 2010-507174 A | 3/2010 |
| WO | 92/09279 A1 | 6/1992 |
| WO | 9213451 A1 | 8/1992 |
| WO | 9404530 A1 | 3/1994 |
| WO | 95/19353 A1 | 7/1995 |
| WO | 98/08830 A1 | 3/1998 |
| WO | 98/027069 A1 | 7/1998 |
| WO | 98/37068 A1 | 8/1998 |
| WO | 9857969 A1 | 12/1998 |
| WO | 00/01679 A1 | 1/2000 |
| WO | 00/35913 A1 | 6/2000 |
| WO | 2000035285 | 6/2000 |
| WO | 2000035913 | 6/2000 |
| WO | 2001066534 A2 | 9/2001 |
| WO | 01/87857 A1 | 11/2001 |
| WO | 02/076983 A1 | 10/2002 |
| WO | 02/100826 A2 | 12/2002 |
| WO | 03/018008 A1 | 3/2003 |
| WO | 03/027085 A2 | 4/2003 |
| WO | 2004/014881 A | 2/2004 |
| WO | 2004/014902 A2 | 2/2004 |
| WO | 2004/058253 A1 | 7/2004 |
| WO | 2004/106285 A1 | 12/2004 |
| WO | 2004110351 A2 | 12/2004 |
| WO | 2005/011685 A1 | 2/2005 |
| WO | 2005026139 A1 | 3/2005 |
| WO | 2005/040144 A1 | 5/2005 |
| WO | 2005/066180 A1 | 7/2005 |
| WO | 2005051932 A1 | 9/2005 |
| WO | 2005089545 A1 | 9/2005 |
| WO | 2006/076009 A2 | 7/2006 |
| WO | 2006/089733 A3 | 8/2006 |
| WO | 2006097030 A1 | 9/2006 |
| WO | 2006/114400 A1 | 11/2006 |
| WO | 2007/043400 A1 | 4/2007 |
| WO | 2007075459 A2 | 7/2007 |
| WO | 2007/130820 A2 | 11/2007 |
| WO | 2007145221 A1 | 12/2007 |
| WO | 2007149395 A2 | 12/2007 |
| WO | 2008049864 A1 | 5/2008 |
| WO | 2008/076356 A1 | 6/2008 |
| WO | 2009023721 A1 | 2/2009 |
| WO | 2009/100438 A2 | 8/2009 |
| WO | 2011/071570 A1 | 6/2011 |
| WO | 2012030887 A1 | 8/2012 |
| WO | 2014089219 A1 | 6/2014 |

OTHER PUBLICATIONS

U.S. Appl. No. 15/147,247.
U.S. Appl. No. 15/817,386.
U.S. Appl. No. 14/096,793.
U.S. Appl. No. 14/649,438.
U.S. Appl. No. 16/143,771.
U.S. Appl. No. 14/210,927.
Cesarini, S., et al., "1,3,4-Oxadiazole Formation as Traceless Release in Solid Phase Organic Synthesis," 2006, Tetrahedron, 62/43:10223-10236.
Klyuchnikova, O.A., et al., "Some Reactions of Tetrazolylthiopheses," 2005, Izvestiya Vysshikh Uchebnykh Zavedenii, Khimiya i Khimicheskaya Tekhnologiya, 48/10:53-58 (English abstract only).
Loughlin et al., "Investigations into the Parallel Synthesis of Novel Pyrrole-Oxazole Analogues of the Insecticide Pirate," 2006, Synthesis, No. 12, 1975-1980.
Machida et al., "Photochemistry of the nitrogen-thiocarbonyl systems. Part 1. Photoinduced reactions. Part 68. Photocycloaddition of

(56) References Cited

OTHER PUBLICATIONS arylcarbothioamides with unsaturated systems. Synthesis of 3,5-diaryl-1,2,4-thiadiazoles and 3-aryl-4,4,5,5-tramethylisothiazolines via photogenerated nitrile sulfides," 1984, Tetrahedron Ltrs, 25/4:409-10, CAPLUS, Document No. 100:174747, 2 pages.
Patsenker et al., "Acylation of 5-phenyl-2-(fur-2-yl)oxazole," 1997, Chem Hetero Compounds, 33/11:1277-1271, XP055136874.
Pulici et al., "Trifluoroacetic Anhydride-Mediated Soled-Phase Version of the Robinson-Gabriel Synthesis of Oxazoles," 2005, J Combinatorial Chem, 7/3:463-473, XP055136879.
Radspieler et al., "Total Synthesis of Phorbazole C," 2001, Tetrahedron, 57:4867-4871.
Shang, Z., "Oxidative c-Cyclization of Aromatic Aldehyde N-acylhdrazones by bis(trifluoroacertoxy)iodobenzene," 2006, Synthetic Communications, 36(20):2927-2937.
Shkumat, A.P. et al, 2-(2-furyl)- and 2-(2-thienyl)-5aryloxazoles, Ukrainskii Khimicheskii Zhumal, 1987, 53/5:529-533, XP-002728980, CAPLUS Record 1988:75262, 1 page.
Sung, H-H., et al., Novel Alternating Fluorene-based Conjugated Polymers Containing Oxadiazole Pendants with Various Terminal Groups, 2004, Macromolecules, 37/21:7945-7954.
Wei, J-Z., et al., "Bacillus thuringiensis Crystal Proteins that Target Nematodes," 2003, PNAS, 100/5:2760-2765.
Yan et al., "Organic reactions in ionic liquids. Oxidative dimerisation of thioamides with phenyliodine(III) diacetate," 2003, J Chem Res, 10:618-619, CAPLUS, DOC No. 1400.357270.
Zhang, Z., et al., "Studies on the Synthesis and Biological Activity of 2-aryl-5-(5-methylisoxazole-3-yl)-1,3,4-oxadiazole derivatives and related property," 1992, Lanzhou Daxue Suebao, Ziran Kexueban, 28/2:103-111 (English Abstract only).
CAS Registry No. 678167-41-4; STN Entry Date Apr. 30, 2004, 2-(2-chlorophenyl)-5-(2-methyl-3-furanyl)-1,3,4-Oxadiazole.
Obukhov, A.E., "Localization of the pump-induced electron interaction and of spin-orbital coupling or the near-lying singlet and triplet excited states in the impurity generation of light in the series multiatomic molecules," 2004, Proceedings of SPIE—The International Society for Optical Engineering, 5402:400-411.
CAS Registry No. 1071700-58-7, Accessed via STN Registry database, entry dated Nov. 9, 2008, Accessed May 28, 2015, 1 page.
Ito, N., et al., "A Medium-Term Rat Liver Bioassay for Rapid in vivo Detection of Carcinogenic Potential of Chemicals," 2003, Cancer Science, 94/1:3-8.
Weaver, G.W., "Product Class 8: 1,3,4-Oxadiazoles," 2004, Science of Synthesis, 13:219-251, 35 pages.
Loughlin, W.A., et al., "Synthesis of a Novel Pyrrole Oxazole Analogue of the Insecticide Pirate," 2004, Aust. J. Chem., 57:227-232.
Loughlin, W.A., et al., "Studies Towards the Synthesis of Phorbazoles A-D: Formation of the Pyrrole Oxazole Skeleton," 1999, Aust. J. Chem., 52:231-234.
Rudi, A., et al., "Phorbazoles A-D, Novel Chlorinated Phenylpyrrolyloxazoles from the Marine Sponge Phorbas aff. clathrate," 1994, Tetrahedron Letters, 35/16:2589-2592, 4 pages.
CAS Registry No. 312921-18-9, Accessed via STN Registry Database, entry dated Jan. 5, 2001, 1 page.
CAS Registry No. 314753-33-8, Accessed via STN Registry Database, entry dated Jan. 18, 2001, 1 page.
CAS Registry No. 310451-46-8, Accessed via STN Registry Database, entry dated Dec. 21, 2000, 1 page.
"Dispersants and Wetting Agents for SC and WDG," 2012, Akzo Morwet Tech Bulletin, v2, indd 1, 2 pages.
"An Introduction to Suspension Concentrates," undated, Vanderbilt Presentation, 27 pages.
Iino Minom et al., "Rational Design and Evaluation of New Lead Compound Structures for Selective β ARKI Inhibitors," 2002, J Med Chem, American Chemical Society, 45:2150-2159.
Sherman et al., "Syntheses With 5-Nitro-2-Furonitrile," 1965, Antibacterial 5-Nitro-2-Furan Derivatives, 85:25-28.
Sherman et al., "5-Nitro-2-Furyl-substituted 1,3,4-oxadiaoles, 1,3,4-thiadiazoles, and 1,3,5-triazines," 1961, JOC, 26:88-95.
Morwick, T., et al., "A Practical Appraoch to the Synthesis of 2,4-Disubstituted Oxazoles from Amino Acids," 2002, Org Ltrs, 4/16:2665-2668, 4 pages.
How to Identity and Manage Pine Wilt Disease and Treat Wood Products Infested by the Pinewood Nematodes [online]. retrieved from the Internet on Jun. 5, 2010. [URL; http://na.fs.fed.us/spfo/pubs/howtos/ht_pinewilt/pinewilt.htm.
Bridge, et al., Musa Pest Fact Sheet No. 2, Nov. 1997.
Barker et al., "Plant and Soil Nematodes: Societal Impact and Focus for the Future," 1994, J Nematol., 26(2):127-137.
Becker, "Seeking New Controls for Costly Nematodes," 1999, Agricultural Research, pp. 22-24.
Carpenter et al., "Township Limits on 1,3-D Will Impact Adjustment to Methyl Bromide Phase-Out," 1001, California Agriculture, 55(3):12-18.
Carter, "Costs Uncertain: Methyl Bromide Phase-Out Becomes Reality" 2001, California Agriculture 55(3):2.
Crow, "Alternatives to Fenamiphos for Management of Plant-Parasitic Nematodes on Bermudagrass," 2005, J Nematol., 37(4):477-482.
Geerts et al., "Anhelmintic Resistance in Human Helminths: Learning from the Problems with Worm Control in Livestock," 1997, Parasitology Today 13:149-151.
Hackney et al., "Marigold, Castor Bean, and Chrysanthemum as Controls of Meloidogyne Incognita and Pratylenchus alleni," 1975, J Nematol., 7(1):84-90.
Prichard, "Anthelmintic Restistance" Veterinary Parasitology 54:259-268, 1994.
Sangster et al., "Pharmacology of Anthelmintic Restistance" 1999, Parasitology Today 15(4):141-146.
Chen et al., "The Human Fetal Cochlea Can Be a Source for Auditory Progenitors I Stem Cells Isolation," 2007, Hearing Research 233:23-29.
Kokare et al., "Design, Synthesis and Utilization of a Novel Coupling Reagent for the Preparation of 0-Alkyl Hydroxamic Acids," 2007, Tetrahedron Letters 48:4437-4440.
Gardiner et al., "Synthesis of 1-Alkoxy-2-Alkyl-Benzimidazoles From 2-Nitroanilines via Tandem N-Alkylation-Cyclization-0-Alkylation," 1995, Tetrahedron 51:4101-4110.
Watson et al., "Solid Phase Synthesis of 5-Aminopyrazoles and Derivatives," 1997, Tetrahedron Letters 38:9065-9068.
Pryor et al., "Purification of Maize Alcohol Dehydrogenase and Competitive Inhibition by Pyrazoles," 1982, Biochemistry International 4:431-438.
Hinzen et al., "Erythropoietin in Sensitizer—A Case Study," 2002, Handbook of Combinatorial Chemistry 2:784-805.
Palmberg et al., "Anil synthesis Part 21 Preparation of Stilbenyl Derivatives of Pyrazole," 1979, Helvetica Chimica Acta, 62:1816-1853.
Berger et al., "Anil Synthesis 20 Preparation of Stilbenyl Derivatives of 1,2,4-Oxadiazoles," 1979, Helvetica Chimica Acta, 62:1411-1428.
Sauer et al., "Ring-Opening of Azoles. III. Acylation of 5-Aryl Tetrazoles; a Duplication Procedure for Preparation of Polyaryls," 1960, Tetrahedron 11:241-251.
Popova et al., "Study of 2, 5-Diaryl-1, 3, 4-Oxadiazoles. 1. Electronic Structure and Spectral-Luminescent Properties of Substituted 2,5-Diphenyl-1,3,4-Oxadiazole," 1983, Khimiya Geterotsiklicheskikh Soedinenii, pp. 26-32.
Franco et al., "Influence of Polymeric Counter-Ions on the Langmuirand LB-Film Stability of Amphiphilic 1,3,4-Oxadiazoles," 2002, Colloids and Surfaces, A: Physicochemical and Engineering Aspects pp. 119-126.
Vergne et al., "Discovery of Thiadiazoles as a Novel Structural Class of Potent and Selective PDE7 Inhibitors. Part 1: Design, Synthesis and Structure-Activity Relationship Studies," 2004, Bioorganic & Medicinal Chemistry Letters 14:4607-4613.
Krasovitskii et al., "Synthesis and Spectral-Luminescence Properties of 4-(5-aryl-2-Oxazolyl)Benzoic Acids and Their Derivatives," 1986, Khimiya Geterotsiklicheskikh Soedinenii 9:1261-1264.
Goddard et al., "5-Heteroaryl-2-Thiophenecarboxylic Acids: Oxazoles and Oxadiazoles," 1991, J Heterocyclic Chem, 28:17-28.

(56) References Cited

OTHER PUBLICATIONS

Zhang et al., "Discovery and Structure-Activity Relationship of 3-Aryl-1, 2, 4-Oxadiazoles as a New Series of Apoptosis Inducers and Potential Anticancer Agents," 2005, J Medicinal Chem, 48:5215-5223.
Voron'Ko et al., "Synthesis of 3,5-Disubstituted 1,2,4-Oxadiazoles and Reactivity of N-Hydroxybenzamidines," 2006, Russian Federation, 49:60-63, 11 pages.
Yale et al., "3, 5-Disubstituted-1, 2, 4-0xadiazoles and 4,5-Dihydro-3,5-Disubstituted 1,2,4-0xadiazoles," 1978, J Heterocyclic Chem, 15:1373-1378.
Minoru et al., "Rational Design and Evaluation of New Lead Compound Structures for Selective β ARKI Inhibitors," 2002, J Medl Chem, 45:2150-2159.
Ying et al., "Rapid and Efficient Synthesis of 1 ,2,4-Oxadiazoles Utilizing Polymer-Supported Reagents Under Microwave Heating," 2005, Organic Letters 7:925-928.
Jessen et al., "The Discovery and Mechanism of Action of Novel Tumor-Selective and Apoptosis-Inducing 3,5-Diary-1,2,4-Oxadiazole Series Using a Chemical Genetics Approach," 2005, Molecular Cancer Therapeutics, 4:761-771.
Prieto et al., "Application of Linear Discriminant Analysis in the Virtual Screening of Antichagasic Drugs Through Trypanothione Reductase Inhibition," 2006, Molecular Diversity 10:361-375.
"1,2,4-0xadiazole,5(3-chloro-2-thienyl)-3-phenoxy," Jun. 8, 2008, Database Accession No. 1026287-93-3, Database Registry, Chemical Abstracts Service, Columbus, OH, 1 page. XP002696671.
Anon., "Herbicidal Oxadiazole Derivatives," 1990, Research Disclosure, 317, 777-779.
Srivastava et al., "Synthesis of3-Aryl-5-[Thien-3-yl Methyl]1,2,4-Oxadiazoles," 1999, Synthetic Communications, 29(9): 1437-1450.
Kwok et al., "A Small-Molecule Screen in C. Elegans Yields a New Calcium Channel Antagonist", 2006, Nature, vol. 441, 32 pages.
Davydov et al., Regioselective Arylation of N-Tributylstannylated 5-Substituted Tetrazoles by Diaryliodonium Salts in the Presence of Cu(OAc)2, 2002, Tetrahedron Letters, 43:6217-6219.
Shawali et al., "Azo Coupling of Benzenesulfonythydrazones of Heterocyclic Aldehydes," 1979, J Hetero Chem, 16/1:123-128.
Smith et al., "Discovery of Highly Potent, Selective, Orally Bioavailable, Metabotropic Glutamate Subtype 5 (mGlu5) Receptor Antagonists Devoid of Cytochrome P450 1A2 Inhibitory Activity," 2004, Bioorgan & Med Chern Lttrs, 14:5481-5484.
International Preliminary Report on Patentability issued in PCT/US2010/023689, dated Feb. 10, 2010, 7 pages.
International Search Report and Written Opinion issued in PCT/US2010/023689, dated Mar. 28, 2011, 12 pages.
International Search Report and Written Opinion issued in PCT/US2011/049847, dated Oct. 24, 2011, 14 pages.
Atkins, J.M., et al., "A Two-Stage Iterative Process for the Synthesis of Poly-oxazoles," 2005, Org Ltrs, 7/15:3351-3354.
Lankau et al., "New GABA-modulating 1,2,4,-Oxadiazole Derivatives and Their Anticonvulsant Activity," 2007, Euro J Med Chem, 42:873-879.
Plaskon et al., "A Synthesis of 5-Hetaryl-3-(2-Hydroxybenzoyl)Pyrroles," 2008, Tetrahedron, 64:5933-5943.
Haugwitz et al., "Antiparasitic Agents. 6. Synthesis and Anthelmintic Activities of Novel Isothiocyanatophenyl-1,2,4-oxadiozoles," 1985, J Med Chem, 28:1234-1241.
Liu, B., "Pesticide Formulation Processing Technology," Chapter 7, 1998, 2nd Edition, pp. 301-335.
Tam, et al., "Medicinal Chemistry and Properties of 1,2,4-thiadiazoles," 2005, Mini Rev Med Chem, 5/4:367-379, Abstract Only, 1 page.
Shi, et al., "Synthesis and Quantitative Structure-Activity Relationships of New 2,5-Disubstituted-1,3,4-oxadiazoles," 2001, J Agric Food Chem, 49:124-130, 7 pages.
Slomczynska, U., et al., "AGRO 39: Tioxazefen: A New Broad-Spectrum Seed Treatment Nematicide,", Aug. 10-14, 2014, 13th IUPAC International Contress of Pesticide Chemistry Crop, Environment, and Public Health Protection Technologies for a Changing World, pp. 1-269, XP55630363, HTTPS://www.iupac2014.org/wp-content/uploadsS/2014/07/IUPAC_CONGRESS_2014_Abstracts.pdf.
Slomczynska, U., et al., "Tioxzafen: A New Broad-Spectrum Seed Treatment Nematicide," ACS Symposium Series, Apr. 11, 2015, XP055429541, vol. 1204:129-147.
STN Registry entry for CAS RN 958734-39-9, entered STN Dec. 19, 2007, accessed Dec. 23, 2019, 1 page.

COMPOSITIONS AND METHODS FOR CONTROLLING NEMATODES

CROSS-REFERENCE TO RELATED APPLICATIONS

This application is a continuation of pending U.S. patent application Ser. No. 16/137,641, filed Sep. 21, 2018, which is a divisional of U.S. patent application Ser. No. 15/415,170, filed Jan. 25, 2017, now issued U.S. Pat. No. 10,112,930, which is a divisional of U.S. patent application Ser. No. 14/790,726, filed Jul. 2, 2015, now issued as U.S. Pat. No. 9,642,364, which is a continuation of U.S. patent application Ser. No. 13/856,236, filed Apr. 3, 2013, now issued as U.S. Pat. No. 9,125,410, which is a divisional of U.S. patent application Ser. No. 12/190,989, filed Aug. 13, 2008, now issued as U.S. Pat. No. 8,435,999, and claims the benefit of U.S. Provisional Patent Application Ser. No. 60/955,448, filed Aug. 13, 2007, the entire disclosures of which are herein incorporated by reference.

BACKGROUND OF THE INVENTION

Nematodes (derived from the Greek word for thread) are active, flexible, elongate, organisms that live on moist surfaces or in liquid environments, including films of water within soil and moist tissues within other organisms. While only 20,000 species of nematode have been identified, it is estimated that 40,000 to 10 million actually exist. Many species of nematodes have evolved to be very successful parasites of plants and animals and are responsible for significant economic losses in agriculture and livestock and for morbidity and mortality in humans (Whitehead (1998) *Plant Nematode Control*. CAB International, New York).

Nematode parasites of plants can infest all parts of plants, including roots, developing flower buds, leaves, and stems. Plant parasites are classified on the basis of their feeding habits into the broad categories migratory ectoparasites, migratory endoparasites, and sedentary endoparasites. Sedentary endoparasites, which include the root knot nematodes (*Meloidogyne*) and cyst nematodes (*Globodera* and *Heterodera*) induce feeding sites and establish long-term infections within roots that are often very damaging to crops (Whitehead, supra). It is estimated that parasitic nematodes cost the horticulture and agriculture industries in excess of $78 billion worldwide a year, based on an estimated average 12% annual loss spread across all major crops. For example, it is estimated that nematodes cause soybean losses of approximately $3.2 billion annually worldwide (Barker et al. (1994) *Plant and Soil Nematodes: Societal Impact and Focus for the Future*. The Committee on National Needs and Priorities in Nematology. Cooperative State Research Service, US Department of Agriculture and Society of Nematologists). Several factors make the need for safe and effective nematode controls urgent. Continuing population growth, famines, and environmental degradation have heightened concern for the sustainability of agriculture, and new government regulations may prevent or severely restrict the use of many available agricultural anthelmintic agents.

There are a very small array of chemicals available to effectively control nematodes (Becker (1999) *Agricultural Research Magazine* 47(3):22-24; U.S. Pat. No. 6,048,714). In general, chemical nematicides are highly toxic compounds known to cause substantial environmental damage and are increasingly restricted in the amounts and locations in which they can be used. For example, the soil fumigant methyl bromide which has been used effectively to reduce nematode infestations in a variety of specialty crops, is regulated under the U.N. Montreal Protocol as an ozone-depleting substance and is undergoing phase out in the US and worldwide (Carter (2001) *California Agriculture*, 55(3): 2). It is expected that strawberry and other commodity crop industries will be significantly impacted if a suitable replacement for methyl bromide is not found. Similarly, broad-spectrum nematicides such as Telone (various formulations of 1,3-dichloropropene) have significant restrictions on their use because of toxicological concerns (Carter (2001) *California Agriculture*, 55(3):12-18). Organophosphate and carbamate pesticides are another important class of nematicides undergoing regulatory review and several of these compounds are currently being phase out (e.g., fenamiphos, terbufos, cadusafos).

To date little success has been achieved in finding safe effective replacements for the toxic but efficacious conventional nematicides. A recent example of the poor efficacy of many newer potential replacements for organophosphates and carbamates is the study of alternatives to fenamiphos for management of plant parasitic nematodes in bermudagrass. In these trials, none of the experimental treatments reduced population densities of the plant parasitic nematodes, or consistently promoted turf visual performance or turf root production (Crow (2005) *Journal of Nematology*, 37(4):477-482). Consequently there remains an urgent need to develop environmentally safe, efficacious methods of controlling plant parasitic nematodes Some plant species are known to be highly resistant to nematodes. The best documented of these include marigolds (*Tagetes* spp.), rattlebox (Crotalaria *spectabilis*), chrysanthemums (*Chrysanthemum* spp.), castor bean (*Ricinus communis*), margosa (Azardiracta indica), and many members of the family Asteraceae (family Compositae) (Hackney & Dickerson. (1975) *J Nematol* 7(1):84-90). In the case of the Asteraceae, the photodynamic compound alpha-terthienyl has been shown to account for the strong nematicidal activity of the roots. Castor beans are plowed under as a green manure before a seed crop is set. However, a significant drawback of the castor plant is that the seed contains toxic compounds (such as ricin) that can kill humans, pets, and livestock and is also highly allergenic. In most cases however, the active principle(s) for plant nematicidal activity has not been discovered and it remains difficult to derive commercially successful nematicidal products from these resistant plants or to transfer the resistance to crops of agronomical importance such as soybeans and cotton.

Genetic resistance to certain nematodes is available in some commercial cultivars (e.g., soybeans), but these are restricted in number and the availability of cultivars with both desirable agronomic features and resistance is limited. Furthermore, the production of nematode resistant commercial varieties by conventional plant breeding based on genetic recombination through sexual crosses is a slow process and is often further hampered by a lack of appropriate germplasm.

Chemical means of controlling plant parasitic nematodes continue to be essential for many crops which lack adequate natural resistance or a source of transgenic resistance. In the specialty markets, economic hardship resulting from nematode infestation is particularly high in strawberries, bananas, and other high value vegetables and fruits. In the high-acreage crop markets, nematode damage is greatest in soybeans and cotton. There are however, dozens of additional crops that suffer from significant nematode infestation including potato, pepper, onion, citrus, coffee, sugarcane, greenhouse ornamentals and golf course turf grasses.

To be useful in modern agriculture nematicides must have high potency, a broad spectrum of activity against different strains of nematodes and should not be toxic to non-target organisms.

Nematode parasites of vertebrates (e.g., humans, livestock and companion animals) include gut roundworms, hookworms, pinworms, whipworms, and filarial worms. They can be transmitted in a variety of ways, including by water contamination, skin penetration, biting insects, or by ingestion of contaminated food.

In domesticated animals, nematode control or "de-worming" is essential to the economic viability of livestock producers and is a necessary part of veterinary care of companion animals. Parasitic nematodes cause mortality in animals (e.g., heartworm in dogs and cats) and morbidity as a result of the parasites' inhibiting the ability of the infected animal to absorb nutrients. The parasite-induced nutrient deficiency leads to disease and stunted growth in livestock and companion animals. For instance, in cattle and dairy herds, a single untreated infection with the brown stomach worm can permanently restrict an animal's ability to convert feed into muscle mass or milk.

Two factors contribute to the need for novel anthelmintics and vaccines to control animal parasitic nematodes. First, some of the more prevalent species of parasitic nematodes of livestock are building resistance to the anthelmintic drugs available currently, meaning that these products are losing their efficacy. These developments are not surprising because few effective anthelmintic drugs are available and most have been used continuously. Some parasitic species have developed resistance to most of the anthelmintics (Geents et al. (1997) *Parasitology Today* 13:149-151; Prichard (1994) *Veterinary Parasitology* 54:259-268). The fact that many of the anthelmintic drugs have similar modes of action complicates matters, as the loss of sensitivity of the parasite to one drug is often accompanied by side resistance—that is, resistance to other drugs in the same class (Sangster & Gill (1999) *Parasitology Today* 15(4):141-146). Secondly, there are some issues with toxicity for the major compounds currently available.

Infections by parasitic nematode worms also result in substantial human mortality and morbidity, especially in tropical regions of Africa, Asia, and the Americas. The World Health Organization estimates 2.9 billion people are infected, and in some areas, 85% of the population carries worms. While mortality is rare in proportion to infections, morbidity is substantial and rivals diabetes and lung cancer in worldwide disability adjusted life year (DALY) measurements.

Examples of human parasitic nematodes include hookworms, filarial worms, and pinworms. Hookworms (1.3 billion infections) are the major cause of anemia in millions of children, resulting in growth retardation and impaired cognitive development. Filarial worms invade the lymphatics, resulting in permanently swollen and deformed limbs (elephantiasis), and the eyes, causing African river blindness. The large gut roundworm *Ascaris lumbricoides* infects more than one billion people worldwide and causes malnutrition and obstructive bowel disease. In developed countries, pinworms are common and often transmitted through children in daycare.

Even in asymptomatic parasitic infections, nematodes can still deprive the host of valuable nutrients and increase the ability of other organisms to establish secondary infections. In some cases, infections can cause debilitating illnesses and can result in anemia, diarrhea, dehydration, loss of appetite, or death.

Despite some advances in drug availability and public health infrastructure and the near elimination of one tropical nematode (the water-borne Guinea worm), most nematode diseases have remained intractable problems. Treatment of hookworm diseases with anthelmintic drugs, for instance, has not provided adequate control in regions of high incidence because rapid re-infection occurs after treatment. In fact, over the last 50 years, while nematode infection rates have fallen in the United States, Europe, and Japan, the overall number of infections worldwide has kept pace with the growing world population. Large scale initiatives by regional governments, the World Health Organization, foundations, and pharmaceutical companies are now underway attempting to control nematode infections with currently available tools, including three programs for control of Onchocerciasis (river blindness) in Africa and the Americas using ivermectin and vector control; The Global Alliance to Eliminate Lymphatic Filariasis using DEC, albendazole, and ivermectin; and the highly successful Guinea Worm Eradication Program. Until safe and effective vaccines are discovered to prevent parasitic nematode infections, anthelmintic drugs will continue to be used to control and treat nematode parasitic infections in both humans and domestic animals.

Certain insecticidal oxazoles (U.S. Pat. No. 4,791,124) and thiazoles (U.S. Pat. No. 4,908,357) and nematicidal pyrazoles (U.S. Pat. No. 6,310,049) have been disclosed in the art. The present invention discloses other oxazoles, oxadiazoles and thiadiazoles with surprisingly potent nematicidal activity showing activity comparable to commercial standards. Commercial level nematicidal potency has not previously been demonstrated with oxazoles, oxadiazoles and thiadiazoles. Importantly, these compounds are broadly active against nematodes yet safe to non-target organisms.

U.S. Pat. No. 4,791,124 disclosed certain oxazoles and thiazoles with nematicidal activity against *Meloidogyne incognita* (root knot nematode) at 10 parts per million. However, compounds were not titrated to lower doses, and as can be seen in table 1D herein certain thiazole analogs which appear highly efficacious at 8 ppm are not comparable in potency to commercial standards and as they do not retain appreciable nematicidal activity at 1 ppm.

U.S. Pat. No. 6,310,049 discloses certain nematicidal pyrazoles with activity against root knot nematode. Several pyrazole compounds are shown having activity at 100 ppm in an in vitro assay with a small subset of the compounds having activity at 50 ppm in a soil based greenhouse. One compound is disclosed as having greenhouse activity at 20 ppm and a single compound as having greenhouse activity at 5 ppm. It is not clear if any of these compounds have potency comparable to commercial standards, i.e., at 1 ppm. As can be seen in table 1D herein, nematicidal activity is seen for 3-(furan-2-yl)-5-phenyl-1H-pyrazole at 8 ppm but not 1 ppm whereas many oxazoles and oxadiazoles have nematicidal potency comparable to commercial standards at 1 ppm.

Some oxadiazoles compounds having substituted furan or thiophene rings but not unsubstituted furan or thiophene rings are disclosed as being apoptosis inducers and useful as chemotherapeutic against certain cancers (Zhang et al. 2005 *J Med Chem.* 48(16):5215-23). Notwithstanding some superficial chemical similarities the nematicidal analogs of this invention do not induce apoptosis in mammalian cells and have equal potency against wild type *C. elegans* nematodes and ced-3 or ced-4 *C. elegans* mutants deficient in apoptosis. These analogs are therefore structurally and functionally distinct from the apoptosis inducing oxadiazoles disclosed by Cai et al in U.S. Pat. No. 7,041,685.

SUMMARY OF THE INVENTION

Compositions and processes for controlling nematodes are described herein, e.g., nematodes that infest plants or the situs of plants. Nematodes that parasitize animals can also be controlled using the methods and compounds described herein.

Described herein are nematicidal compositions comprising an effective amount of a compound or a mixture of compounds having any of the formula described herein, for example the compounds shown below.

Described herein are a compound of Formula I or a salt thereof,

Formula I $$A \underset{B-N}{\overset{O}{\diagdown}} C$$

wherein,

A is phenyl, pyridyl, or pyrazyl each of which can be optionally independently substituted one or more substituents selected from: halogen, $CF_3$, $CH_3$, $OCF_3$, $OCH_3$, CN and C(H)O;

B is C(H) or C($CH_3$); and

C is thienyl, furanyl, oxazolyl or isoxazolyl each of which can be optionally independently substituted with one or more substituents selected from: fluorine, chlorine, $CH_3$, and $OCF_3$.

In various embodiments: A is phenyl; A is pyridyl; A is pyrazyl; B is C(H); B is C($CH_3$); C is thienyl; C is furanyl; C is oxazolyl; and C is isoxazolyl.

Also disclosed are compounds having Formula Ia or a salt thereof,

Formula Ia wherein, $R_1$ and $R_5$ are independently selected from hydrogen, $CH_3$, F, Cl, Br, $CF_3$, and $OCF_3$, with the proviso that $R_1$ and $R_5$ cannot be simultaneously hydrogen;

$R_2$ and $R_4$ are independently selected from hydrogen, F, Cl, Br, and $CF_3$;

$R_3$ is selected from hydrogen, $CH_3$, $CF_3$, F, Cl, Br, $OCF_3$, $OCH_3$, CN, and C(H)O;

$R_7$ and $R_8$ are independently selected from hydrogen and fluorine;

$R_9$ is selected from hydrogen, F, Cl, $CH_3$, and $OCF_3$;

B is C(H) or C($CH_3$); and

E is O or S.

In various embodiments of the compound of Formula Ia: $R_1$ and $R_5$ are independently selected from hydrogen, fluorine and chlorine with the proviso that $R_1$ and $R_5$ cannot be simultaneously hydrogen; $R_1$ and $R_5$ are independently selected from hydrogen, chlorine and fluorine with the proviso that $R_1$ and $R_5$ cannot be simultaneously hydrogen, and $R_3$ is selected from Cl, Br and F; $R_1$ and $R_5$ are independently selected from hydrogen, chlorine and fluorine with the proviso that $R_1$ and $R_5$ cannot be simultaneously hydrogen and $R_3$ is selected from Cl and Br; $R_1$ and $R_5$ are independently selected from hydrogen, chlorine and fluorine with the proviso that $R_1$ and $R_5$ cannot be simultaneously hydrogen, $R_3$ is selected from Cl, Br, F, and E is S; $R_1$ and $R_5$ are independently selected from hydrogen, chlorine and fluorine with the proviso that $R_1$ and $R_5$ cannot be simultaneously hydrogen, $R_3$ is selected from Cl, Br, and F, E is S, and both $R_2$ and $R_4$ are hydrogen; $R_1$ and $R_5$ are independently selected from hydrogen, chlorine and fluorine with the proviso that $R_1$ and $R_5$ cannot be simultaneously hydrogen, $R_3$ is selected from Cl, Br, F, E is S, both $R_2$ and $R_4$ are hydrogen and $R_7$, $R_8$ and $R_9$ are all hydrogen or fluorine; $R_1$ and $R_5$ are independently selected from hydrogen, chlorine and fluorine with the proviso that $R_1$ and $R_5$ cannot be simultaneously hydrogen, $R_3$ selected from Cl, E is S, both $R_2$ and $R_4$ are hydrogen, and $R_7$, $R_8$ and $R_9$ are all hydrogen or fluorine; and $R_1$ and $R_5$ are independently selected from hydrogen, chlorine and fluorine with the proviso that $R_1$ and $R_5$ cannot be simultaneously hydrogen, $R_3$ is selected from Br, E is S, both $R_2$ and $R_4$ are hydrogen and $R_7$, $R_8$ and $R_9$ are all hydrogen or fluorine; $R_1$ and $R_5$ are independently selected from hydrogen and fluorine with the proviso that $R_1$ and $R_5$ cannot be simultaneously hydrogen, $R_3$ is selected from Cl, E is S, $R_2$ and $R_4$ both are hydrogen and $R_7$, $R_8$ and $R_9$ are hydrogen; $R_1$ and $R_5$ are independently selected from hydrogen, chlorine and fluorine with the proviso that $R_1$ and $R_5$ cannot be simultaneously hydrogen, $R_3$ is s Br, E is S, both $R_2$ and $R_4$ are hydrogen, and $R_7$, $R_8$ and $R_9$ are all hydrogen.

Also disclosed are compounds having Formula Ib or a salt thereof,

Formula Ib wherein, $R_1$ and $R_5$ are independently selected from hydrogen, $CH_3$, F, Cl, Br, $CF_3$, and $OCF_3$;

$R_2$ and $R_4$ are independently selected from hydrogen, F, Cl, Br, and $CF_3$;

$R_3$ is selected from hydrogen, $CH_3$, $CF_3$, F, Cl, Br, $OCF_3$, $OCH_3$, CN, and CO;

$R_8$ is selected from hydrogen and fluorine;

$R_6$ and $R_9$ are independently selected from hydrogen, F, Cl, $CH_3$, and $OCF_3$;

B is C(H) or C($CH_3$); and

E is O or S.

In various embodiments of the compound of Formula Ib: $R_1$ and $R_5$ are independently selected from hydrogen, fluorine and chlorine with the proviso that $R_1$ and $R_5$ cannot be simultaneously hydrogen; $R_1$ and $R_5$ are independently selected from hydrogen, chlorine and fluorine with the proviso that $R_1$ and $R_5$ cannot be simultaneously hydrogen, and $R_3$ is selected from Cl, Br and F; $R_1$ and $R_5$ are independently selected from hydrogen, chlorine and fluorine with the proviso that $R_1$ and $R_5$ cannot be simultaneously hydrogen and $R_3$ is selected from Cl and Br; $R_1$ and $R_5$ are independently selected from hydrogen, chlorine and fluorine with the proviso that $R_1$ and $R_5$ cannot be simultaneously hydrogen, $R_3$ is selected from Cl, Br, F, and E is S; $R_1$ and $R_5$ are independently selected from hydrogen, chlorine and fluorine with the proviso that $R_1$ and $R_5$ cannot be simultaneously hydrogen, $R_3$ is selected from Cl, Br, and F, E is S, and both $R_2$ and $R_4$ are hydrogen; $R_1$ and $R_5$ are independently selected from hydrogen, chlorine and fluorine with the proviso that $R_1$ and $R_5$ cannot be simultaneously hydrogen, $R_3$ is selected from Cl, Br, F, E is S, both $R_2$ and $R_4$ are hydrogen and $R_7$, $R_8$ and $R_9$ are all hydrogen or fluorine; $R_1$ and $R_5$ are independently selected from hydrogen, chlorine and fluorine with the proviso that $R_1$ and $R_5$ cannot be simultaneously hydrogen, $R_3$ selected from Cl, E is S, both $R_2$ and $R_4$ are hydrogen, and $R_7$, $R_8$ and $R_9$ are all hydrogen or fluorine; and $R_1$ and $R_5$ are independently selected from hydrogen, chlorine and fluorine with the proviso that $R_1$ and $R_5$ cannot be simultaneously hydrogen, $R_3$ is selected from Br, E is S, both $R_2$ and $R_4$ are hydrogen and $R_7$, $R_8$ and $R_9$ are all hydrogen or fluorine; $R_1$ and $R_5$ are independently selected from hydrogen and fluorine with the proviso that $R_1$ and $R_5$ cannot be simultaneously hydrogen, $R_3$ is selected from Cl, E is S, $R_2$ and $R_4$ both are hydrogen and $R_7$, $R_8$ and $R_9$ are hydrogen; $R_1$ and $R_5$ are independently selected from hydrogen, chlorine and fluorine with the proviso that $R_1$ and $R_5$ cannot be simultaneously hydrogen, $R_3$ is s Br, E is S, both $R_2$ and $R_4$ are hydrogen, and $R_7$, $R_8$ and $R_9$ are all hydrogen.

Disclosed herein are compounds of Formula II or a salt thereof

Formula II wherein,

A is selected from: phenyl, pyridyl, and pyrazyl, each of which can be optionally independently substituted with one or more substituents selected from: halogen, $CF_3$, $CH_3$, $OCF_3$, $OCH_3$, CN, and C(H)O;

B is C(H) or $C(CH_3)$;

C is selected from: thienyl, furanyl, oxazolyl or isoxazolyl, each of which can be optionally independently substituted with one or more substituents selected from: fluorine, chlorine, $CH_3$, and $OCF_3$.

In various embodiments: A is phenyl; A is pyridyl; A is pyrazyl; B is C(H); B is $C(CH_3)$; C is thienyl; C is furanyl; C is oxazolyl; and C is isoxazolyl.

Disclosed herein are compounds having Formula IIa wherein, $R_1$ and $R_5$ are independently selected from hydrogen, $CH_3$, F, Cl, Br, $CF_3$ and $OCF_3$
with the proviso that $R_1$ and $R_5$ cannot be simultaneously hydrogen;

$R_2$ and $R_4$ are independently selected from hydrogen, F, Cl, Br, and $CF_3$;

$R_3$ is selected from hydrogen, $CH_3$, $CF_3$, F, Cl, Br, $OCF_3$, $OCH_3$, CN, and C(H)O;

$R_7$ and $R_8$ are independently selected from hydrogen and F;

$R_9$ is selected from hydrogen, F, Cl, $CH_3$, and $OCF_3$;

B is C(H) or $C(CH_3)$; and

E is O or S.

In various embodiments of the compound of Formula IIa: $R_1$ and $R_5$ are independently selected from hydrogen, fluorine and chlorine with the proviso that $R_1$ and $R_5$ cannot be simultaneously hydrogen; $R_1$ and $R_5$ are independently selected from hydrogen, chlorine and fluorine with the proviso that $R_1$ and $R_5$ cannot be simultaneously hydrogen, and $R_3$ is selected from Cl, Br and F; $R_1$ and $R_5$ are independently selected from hydrogen, chlorine and fluorine with the proviso that $R_1$ and $R_5$ cannot be simultaneously hydrogen and $R_3$ is selected from Cl and Br; $R_1$ and $R_5$ independently selected from hydrogen, chlorine and fluorine with the proviso that $R_1$ and $R_5$ cannot be simultaneously hydrogen, $R_3$ is selected from Cl, Br, F, and E is S; $R_1$ and $R_5$ are independently selected from hydrogen, chlorine and fluorine with the proviso that $R_1$ and $R_5$ cannot be simultaneously hydrogen, $R_3$ is selected from Cl, Br, and F, E is S, and both $R_2$ and $R_4$ are hydrogen; $R_1$ and $R_5$ are independently selected from hydrogen, chlorine and fluorine with the proviso that $R_1$ and $R_5$ cannot be simultaneously hydrogen, $R_3$ is selected from Cl, Br, F, E is S, both $R_2$ and $R_4$ are hydrogen and $R_7$, $R_8$ and $R_9$ are all hydrogen or fluorine; $R_1$ and $R_5$ are independently selected from hydrogen, chlorine and fluorine with the proviso that $R_1$ and $R_5$ cannot be simultaneously hydrogen, $R_3$ selected from Cl, E is S, both $R_2$ and $R_4$ are hydrogen, and $R_7$, $R_8$ and $R_9$ are all hydrogen or fluorine; and $R_1$ and $R_5$ are independently selected from hydrogen, chlorine and fluorine with the proviso that $R_1$ and $R_5$ cannot be simultaneously hydrogen, $R_3$ is selected from Br, E is S, both $R_2$ and $R_4$ are hydrogen and $R_7$, $R_8$ and $R_9$ are all hydrogen or fluorine; $R_1$ and $R_5$ are independently selected from hydrogen and fluorine with the proviso that $R_1$ and $R_5$ cannot be simultaneously hydrogen, $R_3$ is selected from Cl, E is S, $R_2$ and $R_4$ both are hydrogen and $R_7$, $R_8$ and $R_9$ are hydrogen; $R_1$ and $R_5$ are independently selected from hydrogen, chlorine and fluorine with the proviso that $R_1$ and $R_5$ cannot be simultaneously hydrogen, $R_3$ is s Br, E is S, both $R_2$ and $R_4$ are hydrogen, and $R_7$, $R_8$ and $R_9$ are all hydrogen.

Disclosed herein are compounds having Formula IIb or a salt thereof,

Formula IIa

Formula IIb wherein, $R_1$ and $R_5$ are independently selected from hydrogen, $CH_3$, F, Cl, Br, $CF_3$ and $OCF_3$;

$R_2$ and $R_4$ are independently selected from hydrogen, F, Cl, Br and $CF_3$;

$R_3$ is selected from hydrogen, $CH_3$, $CF_3$, F, Cl, Br, $OCF_3$, $OCH_3$, CN and C(H)O;

$R_8$ is selected from hydrogen and fluorine;

$R_6$ and $R_9$ are independently selected from hydrogen, F, Cl, $CH_3$ and $OCF_3$;

B is C(H) or C($CH_3$); and

E is O or S.

In various embodiments of the compound of Formula IIb: $R_1$ and $R_5$ are independently selected from hydrogen, fluorine and chlorine with the proviso that $R_1$ and $R_5$ cannot be simultaneously hydrogen; $R_1$ and $R_5$ are independently selected from hydrogen, chlorine and fluorine with the proviso that $R_1$ and $R_5$ cannot be simultaneously hydrogen, and $R_3$ is selected from Cl, Br and F; $R_1$ and $R_5$ are independently selected from hydrogen, chlorine and fluorine with the proviso that $R_1$ and $R_5$ cannot be simultaneously hydrogen and $R_3$ is selected from Cl and Br; $R_1$ and $R_5$ are independently selected from hydrogen, chlorine and fluorine with the proviso that $R_1$ and $R_5$ cannot be simultaneously hydrogen, $R_3$ is selected from Cl, Br, F, and E is S; $R_1$ and $R_5$ are independently selected from hydrogen, chlorine and fluorine with the proviso that $R_1$ and $R_5$ cannot be simultaneously hydrogen, $R_3$ is selected from Cl, Br, and F, E is S, and both $R_2$ and $R_4$ are hydrogen; $R_1$ and $R_5$ are independently selected from hydrogen, chlorine and fluorine with the proviso that $R_1$ and $R_5$ cannot be simultaneously hydrogen, $R_3$ is selected from Cl, Br, F, E is S, both $R_2$ and $R_4$ are hydrogen and $R_7$, $R_8$ and $R_9$ are all hydrogen or fluorine; $R_1$ and $R_5$ are independently selected from hydrogen, chlorine and fluorine with the proviso that $R_1$ and $R_5$ cannot be simultaneously hydrogen, $R_3$ selected from Cl, E is S, both $R_2$ and $R_4$ are hydrogen, and $R_7$, $R_8$ and $R_9$ are all hydrogen or fluorine; and $R_1$ and $R_5$ are independently selected from hydrogen, chlorine and fluorine with the proviso that $R_1$ and $R_5$ cannot be simultaneously hydrogen, $R_3$ is selected from Br, E is S, both $R_2$ and $R_4$ are hydrogen and $R_7$, $R_8$ and $R_9$ are all hydrogen or fluorine; $R_1$ and $R_5$ are independently selected from hydrogen and fluorine with the proviso that $R_1$ and $R_5$ cannot be simultaneously hydrogen, $R_3$ is selected from Cl, E is S, $R_2$ and $R_4$ both are hydrogen and $R_7$, $R_8$ and $R_9$ are hydrogen; $R_1$ and $R_5$ are independently selected from hydrogen, chlorine and fluorine with the proviso that $R_1$ and $R_5$ cannot be simultaneously hydrogen, $R_3$ is s Br, E is S, both $R_2$ and $R_4$ are hydrogen, and $R_7$, $R_8$ and $R_9$ are all hydrogen.

Disclosed herein are compounds of Formula III or a salt thereof,

Formula III

A—⟨O⟩—C
   N—N wherein,

A is phenyl, pyridyl, or pyrazyl, each of which can be optionally independently substituted with one or more substituents selected from: halogen, $CF_3$, $CH_3$, $OCF_3$, $OCH_3$, CN and C(H)O.

C is thienyl, furanyl, oxazolyl or isoxazolyl each of which can be optionally independently substituted with one or more substituents selected from: fluorine, chlorine, $CH_3$ and $OCF_3$.

In various embodiments: A is phenyl; A is pyridyl; A is pyrazyl; C is thienyl; C is furanyl; C is oxazolyl; and C is isoxazolyl.

Also disclosed are compounds having Formula IIIa or a salt thereof,

Formula IIIa

[Structure showing phenyl ring with $R_1$, $R_2$, $R_3$, $R_4$, $R_5$ substituents connected via oxadiazole to a ring with E, $R_7$, $R_8$, $R_9$ substituents]

wherein, $R_1$ and $R_5$ are independently selected from hydrogen, $CH_3$, F, Cl, Br, $CF_3$, and $OCF_3$, with the proviso that $R_1$ and $R_5$ cannot be simultaneously hydrogen;

$R_2$ and $R_4$ are independently selected from hydrogen, F, Cl, Br, and $CF_3$;

$R_3$ is selected from hydrogen, $CH_3$, $CF_3$, F, Cl, Br, $OCF_3$, $OCH_3$, CN, and C(H)O;

$R_7$ and $R_8$ are independently selected from hydrogen and fluorine;

$R_9$ is selected from hydrogen, F, Cl, $CH_3$, and $OCF_3$; and

E is O or S.

In various embodiments of the compound of Formula IIIa: $R_1$ and $R_5$ are independently selected from hydrogen and $CH_3$ with the proviso that $R_1$ and $R_5$ cannot be simultaneously hydrogen, $R_3$ fluorine, chlorine or bromine, and E is O; $R_1$ and $R_5$ are independently selected from hydrogen and $CH_3$ with the proviso that $R_1$ and $R_5$ cannot be simultaneously hydrogen, $R_3$ fluorine, chlorine and bromine, E is S, and $R_9$ is hydrogen or fluorine; $R_1$ and $R_5$ are independently selected from hydrogen and $CH_3$ with the proviso that $R_1$ and $R_5$ cannot be simultaneously hydrogen, both $R_2$ and $R_4$ are hydrogen, $R_3$ is chlorine or bromine, and E is O; $R_1$ and $R_5$ are independently selected from hydrogen and $CH_3$ with the proviso that $R_1$ and $R_5$ cannot be simultaneously hydrogen, both $R_2$ and $R_4$ are hydrogen, $R_3$ is chlorine or bromine, E is S, and $R_9$ is hydrogen or fluorine; $R_1$ and $R_5$ are independently selected from hydrogen and Cl, $R_3$ is fluorine, chlorine or bromine, E is O, and $R_9$ is fluorine; $R_1$ and $R_5$ are independently selected from hydrogen and $CH_3$ with the proviso that $R_1$ and $R_5$ cannot be simultaneously hydrogen, $R_3$ is fluorine, chlorine or bromine, and E is O; $R_1$ and $R_5$ are independently selected from hydrogen and $CH_3$ with the proviso that $R_1$ and $R_5$ cannot be simultaneously hydrogen, $R_3$ fluorine, chlorine or bromine, E is S, and $R_9$ is hydrogen or fluorine; $R_1$ and $R_5$ are independently selected from hydrogen and $CH_3$ with the proviso that $R_1$ and $R_5$ cannot be simultaneously hydrogen, both $R_2$ and $R_4$ are hydrogen, $R_3$ is chlorine or bromine, and E is O; $R_1$ and $R_5$ are independently selected from hydrogen and $CH_3$ with the proviso that $R_1$ and $R_5$ cannot be simultaneously hydrogen, $R_2$ and $R_4$ are hydrogen, $R_3$ chlorine or bromine, E is S and $R_9$ is hydrogen or fluorine; $R_1$ and $R_5$ are independently selected from hydrogen and $CH_3$ with the proviso that $R_1$ and $R_5$ cannot be simultaneously hydrogen, both $R_2$ and $R_4$ are hydrogen, $R_3$ is chlorine or bromine, and E is O and $R_7$, $R_8$ and $R_9$ are hydrogen; and $R_1$ and $R_5$ are independently selected from hydrogen and Cl, $R_3$ fluorine, chlorine and bromine, E is O and $R_9$ is fluorine.

Also disclosed are compounds having Formula IIIb or a salt thereof,

Formula IIIb wherein, $R_1$ and $R_5$ are independently selected from hydrogen, $CH_3$, F, Cl, Br, $CF_3$, and $OCF_3$;

$R_2$ and $R_4$ are independently selected from hydrogen, F, Cl, Br, and $CF_3$;

$R_3$ is selected from hydrogen, $CH_3$, $CF_3$, F, Cl, Br, $OCF_3$, $OCH_3$, CN, and C(H)O;

$R_8$ is selected from hydrogen and fluorine;

$R_6$ and $R_9$ are independently selected from hydrogen, F, Cl, $CH_3$, and $OCF_3$; and E is O or S.

In various embodiments of the compound of Formula IIIb: $R_1$ and $R_5$ are independently selected from hydrogen and $CH_3$ with the proviso that $R_1$ and $R_5$ cannot be simultaneously hydrogen, $R_3$ fluorine, chlorine or bromine, and E is O; $R_1$ and $R_5$ are independently selected from hydrogen and $CH_3$ with the proviso that $R_1$ and $R_5$ cannot be simultaneously hydrogen, $R_3$ fluorine, chlorine and bromine, E is S, and $R_9$ is hydrogen or fluorine; $R_1$ and $R_5$ are independently selected from hydrogen and $CH_3$ with the proviso that $R_1$ and $R_5$ cannot be simultaneously hydrogen, both $R_2$ and $R_4$ are hydrogen, $R_3$ is chlorine or bromine, and E is O; $R_1$ and $R_5$ are independently selected from hydrogen and $CH_3$ with the proviso that $R_1$ and $R_5$ cannot be simultaneously hydrogen, both $R_2$ and $R_4$ are hydrogen, $R_3$ is chlorine or bromine, E is S, and $R_9$ is hydrogen or fluorine; $R_1$ and $R_5$ are independently selected from hydrogen and Cl, $R_3$ is fluorine, chlorine or bromine, E is O, and $R_9$ is fluorine; $R_1$ and $R_5$ are independently selected from hydrogen and $CH_3$ with the proviso that $R_1$ and $R_5$ cannot be simultaneously hydrogen, $R_3$ is fluorine, chlorine or bromine, and E is O; $R_1$ and $R_5$ are independently selected from hydrogen and $CH_3$ with the proviso that $R_1$ and $R_5$ cannot be simultaneously hydrogen, $R_3$ fluorine, chlorine or bromine, E is S, and $R_9$ is hydrogen or fluorine; $R_1$ and $R_5$ are independently selected from hydrogen and $CH_3$ with the proviso that $R_1$ and $R_5$ cannot be simultaneously hydrogen, both $R_2$ and $R_4$ are hydrogen, $R_3$ is chlorine or bromine, and E is O; $R_1$ and $R_5$ are independently selected from hydrogen and $CH_3$ with the proviso that $R_1$ and $R_5$ cannot be simultaneously hydrogen, $R_2$ and $R_4$ are hydrogen, $R_3$ chlorine or bromine, E is S and $R_9$ is hydrogen or fluorine; and $R_1$ and $R_5$ are independently selected from hydrogen and Cl, $R_3$ is fluorine, chlorine or bromine, E is O and $R_9$ is fluorine.

Also disclosed are compounds of Formula (IV) or a salt thereof

Formula IV wherein,

A is phenyl, pyridyl, pyrazyl, oxazolyl or isoxazolyl each of which can be optionally independently substituted with one or more substituents selected from: halogen, $CF_3$, $CH_3$, $OCF_3$, $OCH_3$, CN, and C(H)O; and C is thienyl, furanyl, oxazolyl or isoxazolyl, each of which can be optionally independently substituted with one or more substituents selected from fluorine, chlorine, $CH_3$, and $OCF_3$.

In various embodiments: A is phenyl; A is pyridyl; A is pyrazyl; A is oxazolyl; A is isoxazolyl; C is thienyl; C is furanyl; C is oxazolyl; and C is isoxazolyl.

Also disclosed are compounds having Formula IVa or a salt thereof,

Formula IVa wherein, $R_1$ and $R_5$ are independently selected from hydrogen, $CH_3$, F, Cl, Br, $CF_3$ and $OCF_3$, with the proviso that $R_1$ and $R_5$ cannot be simultaneously hydrogen;

$R_2$ and $R_4$ are independently selected from hydrogen, F, Cl, Br, and $CF_3$;

$R_3$ is selected from hydrogen, $CH_3$, $CF_3$, F, Cl, Br, $OCF_3$, $OCH_3$, CN, and C(H)O;

$R_7$ and $R_8$ are independently selected from hydrogen and fluorine;

$R_9$ is selected from hydrogen, F, Cl, $CH_3$, and $OCF_3$; and

E is O or S.

In various embodiments of the compound of Formula IVa: $R_1$ and $R_5$ are independently selected from hydrogen and $CH_3$ with the proviso that $R_1$ and $R_5$ cannot be simultaneously hydrogen, $R_3$ is fluorine, chlorine or bromine, and E is O; $R_1$ and $R_5$ are independently selected from hydrogen and $CH_3$ with the proviso that $R_1$ and $R_5$ cannot be simultaneously hydrogen, both $R_2$ and $R_4$ are hydrogen, $R_3$ is chlorine or bromine, and E is O and $R_7$, $R_8$ and $R_9$ are hydrogen; $R_1$ and $R_5$ are independently selected from hydrogen and $CH_3$ with the proviso that $R_1$ and $R_5$ cannot be simultaneously hydrogen, $R_3$ is fluorine, chlorine or bromine, E is S, and $R_9$ is hydrogen or fluorine; $R_1$ and $R_5$ are independently selected from hydrogen and $CH_3$ with the proviso that $R_1$ and $R_5$ cannot be simultaneously hydrogen, both $R_2$ and $R_4$ are hydrogen, $R_3$ is chlorine or bromine, E is O; $R_1$ and $R_5$ are independently selected from hydrogen and $CH_3$ with the proviso that $R_1$ and $R_5$ cannot be simultaneously hydrogen, both $R_2$ and $R_4$ are hydrogen, $R_3$ is chlorine or bromine, E is S, and $R_9$ is hydrogen or fluorine; $R_1$ and $R_5$ are independently selected from hydrogen and Cl, $R_3$ is fluorine, chlorine or bromine, E is O, and $R_9$ is fluorine.

Also disclosed are compounds having Formula IVb or a salt thereof,

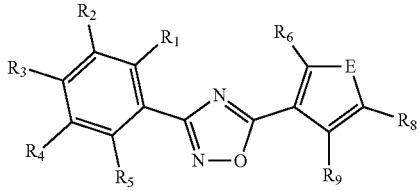

Formula IVb wherein, $R_1$ and $R_5$ are independently selected from hydrogen, $CH_3$, F, Cl, Br, $CF_3$ and $OCF_3$, with the proviso that $R_1$ and $R_5$ cannot be simultaneously hydrogen;

$R_2$ and $R_4$ are independently selected from hydrogen, F, Cl, Br, and $CF_3$;

$R_3$ is selected from hydrogen, $CH_3$, $CF_3$, F, Cl, Br, $OCF_3$, $OCH_3$, CN, and C(H)O;

$R_8$ is selected from hydrogen and fluorine;

$R_6$ and $R_9$ are independently selected from hydrogen, F, Cl, $CH_3$, and $OCF_3$; and E is O or S.

In various embodiments of the compound of Formula IVb: $R_1$ and $R_5$ are independently selected from hydrogen and $CH_3$ with the proviso that $R_1$ and $R_5$ cannot be simultaneously hydrogen, $R_3$ is fluorine, chlorine or bromine, and E is O; $R_1$ and $R_5$ are independently selected from hydrogen and $CH_3$ with the proviso that $R_1$ and $R_5$ cannot be simultaneously hydrogen, $R_3$ is fluorine, chlorine or bromine, E is S, and $R_9$ is hydrogen or fluorine; $R_1$ and $R_5$ are independently selected from hydrogen and $CH_3$ with the proviso that $R_1$ and $R_5$ cannot be simultaneously hydrogen, both $R_2$ and $R_4$ are hydrogen, $R_3$ is chlorine or bromine, E is O; $R_1$ and $R_5$ are independently selected from hydrogen and $CH_3$ with the proviso that $R_1$ and $R_5$ cannot be simultaneously hydrogen, both $R_2$ and $R_4$ are hydrogen, $R_3$ is chlorine or bromine, E is S, and $R_9$ is hydrogen or fluorine; and $R_1$ and $R_5$ are independently selected from hydrogen and Cl, $R_3$ is fluorine, chlorine or bromine, E is O, and $R_9$ is fluorine.

Disclosed herein are compounds of Formula (V) or a salt thereof,

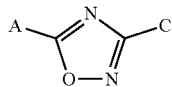

Formula V wherein,

A is phenyl, pyridyl, pyrazyl, oxazolyl or isoxazolyl, each of which can be optionally independently substituted with one or more substituents selected from: halogen, $CF_3$, $CH_3$, $OCF_3$, $OCH_3$, CN, and C(H)O; and C is thienyl, furanyl, oxazolyl or isoxazolyl, each of which can be optionally independently substituted with one or more substituents selected from fluorine, chlorine, $CH_3$, and $OCF_3$.

In various embodiments: A is phenyl; A is pyridyl; A is pyrazyl; A is oxazolyl; A is isoxazolyl; C is thienyl; C is furanyl; C is oxazolyl; and C is isoxazolyl.

Also disclosed are compounds having Formula Va or a salt thereof,

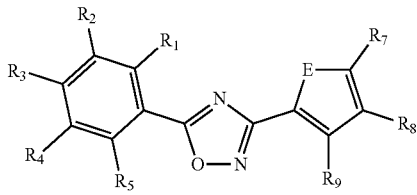

Formula Va wherein, $R_1$ and $R_5$ are independently selected from hydrogen, $CH_3$, F, Cl, Br, $CF_3$ and $OCF_3$, with the proviso that $R_1$ and $R_5$ cannot be simultaneously hydrogen;

$R_2$ and $R_4$ are independently selected from hydrogen, F, Cl, Br, and $CF_3$;

$R_3$ is selected from hydrogen, $CH_3$, $CF_3$, F, Cl, Br, $OCF_3$, $OCH_3$, CN, and C(H)O;

$R_7$ and $R_8$ are independently selected from hydrogen and fluorine;

$R_9$ is selected from hydrogen, F, Cl, $CH_3$, and $OCF_3$; and

E is O or S.

In various embodiments of the compound of Formula Va: $R_1$ and $R_5$ are independently selected from hydrogen and $CH_3$ with the proviso that $R_1$ and $R_5$ cannot be simultaneously hydrogen, $R_3$ is fluorine, chlorine or bromine, E is S, and $R_9$ is hydrogen or fluorine; $R_1$ and $R_5$ are independently selected from hydrogen and $CH_3$ with the proviso that $R_1$ and $R_5$ cannot be simultaneously hydrogen, both $R_2$ and $R_4$ are hydrogen, $R_3$ is chlorine or bromine, E is O; $R_1$ and $R_5$ are independently selected from hydrogen and $CH_3$ with the proviso that $R_1$ and $R_5$ cannot be simultaneously hydrogen, both $R_2$ and $R_4$ are hydrogen, $R_3$ chlorine or bromine, E is S, and $R_9$ is hydrogen or fluorine; $R_1$ and $R_5$ are independently selected from hydrogen and Cl, $R_3$ is fluorine, chlorine or bromine, E is O, and $R_9$ is fluorine.

Also disclosed are compounds having Formula Vb or a salt thereof,

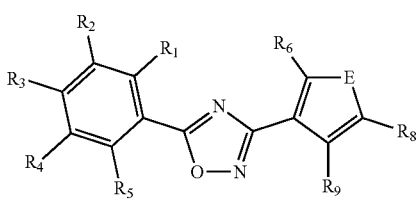

Formula Vb wherein, $R_1$ and $R_5$ are independently selected from hydrogen, $CH_3$, F, Cl, Br, $CF_3$ and $OCF_3$;

$R_2$ and $R_4$ are independently selected from hydrogen, F, Cl, Br, and $CF_3$;

$R_3$ is selected from hydrogen, $CH_3$, $CF_3$, F, Cl, Br, $OCF_3$, $OCH_3$, CN, and C(H)O;

$R_8$ is selected from hydrogen and fluorine;

$R_6$ and $R_9$ are independently selected from hydrogen, F, Cl, $CH_3$, and $OCF_3$; and E is O or S.

In various embodiments of the compound of Formula Vb: $R_1$ and $R_5$ are independently selected from hydrogen and $CH_3$ with the proviso that $R_1$ and $R_5$ cannot be simultaneously hydrogen, $R_3$ is fluorine, chlorine and bromine, and E is O; $R_1$ and $R_5$ are independently selected from hydrogen and $CH_3$ with the proviso that $R_1$ and $R_5$ cannot be simultaneously hydrogen, $R_3$ is fluorine, chlorine or bromine, E is S and $R_9$ is hydrogen or fluorine; $R_1$ and $R_5$ are independently selected from hydrogen and $CH_3$ with the proviso that $R_1$ and $R_5$ cannot be simultaneously hydrogen, both $R_2$ and $R_4$ are hydrogen, $R_3$ is chlorine or bromine, E is O; $R_1$ and $R_5$ are independently selected from hydrogen and $CH_3$ with the proviso that $R_1$ and $R_5$ cannot be simultaneously hydrogen, both $R_2$ and $R_4$ are hydrogen, $R_3$ is chlorine or bromine, E is S, and $R_9$ is hydrogen or fluorine; $R_1$ and $R_5$ are independently selected from hydrogen and Cl, $R_3$ is fluorine, chlorine or bromine, E is O, and $R_9$ is fluorine.

Described herein are compounds having Formula (VI) or a salt thereof,

Formula VI wherein,

A is an optionally substituted aryl or optionally independently singly or multiply substituted arylalkyl or optionally independently singly or multiply substituted heteroaryl or optionally independently singly or multiply substituted heteroarylalkyl wherein the substituents are selected from the group consisting of halo, $C_1$-$C_6$ haloalkyl, $C_6$-$C_{10}$ aryl, $C_4$-$C_7$ cycloalkyl, $C_2$-$C_6$ alkyl, $C_2$-$C_6$ alkenyl, $C_2$-$C_6$ alkynyl, $C_6$-$C_{10}$ aryl($C_1$-$C_6$)alkyl, $C_6$-$C_{10}$ aryl($C_2$-$C_6$)alkenyl, $C_6$-$C_{10}$ aryl($C_2$-$C_6$) alkynyl, $C_1$-$C_6$ hydroxyalkyl, amino, ureido, cyano, $C_1$-$C_6$ acylamino, hydroxy, thiol, $C_1$-$C_6$ acyloxy, azido, $C_1$-$C_6$ alkoxy and carboxy, and C(H)O;

C is a thienyl, furanyl, oxazolyl or isoxazolyl each of which can be optionally independently substituted with one or more with substituents selected from: fluorine, chlorine, $CH_3$, and $OCF_3$.

In various embodiments: A is aryl; A is arylalkyl; A is heteroarylalkyl; A is heteroaryl; C is thienyl; C is furanyl; C is oxazolyl; C is isoxazolyll; A is pyridyl; A is pyrazyl; A is oxazolyl; and A is isoxazolyl; compounds in which both A and C are not thiophenyl and compounds in which both A and C are not furanyl.

Also described herein are compounds having Formula VIa or a salt thereof,

Formula VIa wherein, $R_1$ and $R_5$ are independently selected from hydrogen, $CH_3$, F, Cl, Br, $CF_3$ and $OCF_3$;

$R_2$ and $R_4$ are independently selected from hydrogen, F, Cl, Br, and $CF_3$;

$R_3$ is selected from hydrogen, $CH_3$, $CF_3$, F, Cl, Br, $OCF_3$, $OCH_3$, CN, and C(H)O;

$R_7$ and $R_8$ are independently selected from hydrogen and fluorine;

$R_9$ is selected from hydrogen, F, Cl, $CH_3$, and $OCF_3$; and E is O or S.

In various embodiments of the compound of Formula VIa: $R_1$ and $R_5$ are independently selected from hydrogen, $CH_3$, F and Cl; $R_1$ and $R_5$ are independently selected from hydrogen, $CH_3$, fluorine and Cl, and $R_3$ is $C_1$; $R_1$ and $R_5$ are independently selected from hydrogen, $CH_3$, fluorine and $C_1$, and $R_3$ is Br, $R_1$ and $R_5$ are independently selected from hydrogen, $CH_3$, fluorine and Cl, $R_3$ is $C_1$, and E is O; $R_1$ and $R_5$ are independently selected from hydrogen, $CH_3$, fluorine and $C_1$, and $R_3$ is Br and E is O; $R_1$ and $R_5$ are independently selected from hydrogen and $CH_3$, and $R_3$ is Cl, E is O, and $R_6$, $R_8$ and $R_9$ are selected from hydrogen and fluorine; $R_1$ and $R_5$ are independently selected from hydrogen and $CH_3$, and $R_3$ is Br, E is O, and $R_7$, $R_8$ and $R_9$ are selected from hydrogen and fluorine; $R_1$ and $R_5$ are independently selected from hydrogen and fluorine, and $R_3$ is Cl, E is O, and $R_7$, $R_8$ and $R_9$ are selected from hydrogen and fluorine; $R_1$ and $R_5$ are independently selected from hydrogen and fluorine, $R_3$ is Br, E is O, and $R_7$, $R_8$ and $R_9$ are selected from hydrogen and fluorine; $R_1$ and $R_5$ are independently selected from hydrogen and chlorine, and $R_3$ is Cl, E is O, and $R_7$, $R_8$ and $R_9$ are selected from hydrogen and fluorine; $R_1$ and $R_5$ are independently selected from hydrogen and $CH_3$, $R_3$ is Cl, $R_2$ and $R_4$ are hydrogen E is O, and $R_7$, $R_8$ and $R_9$ are selected from hydrogen and fluorine; $R_1$ and $R_5$ are independently selected from hydrogen and $CH_3$, $R_2$ and $R_4$ are hydrogen, $R_3$ is Br, E is O, and $R_7$, $R_8$ and $R_9$ are selected from hydrogen and fluorine; $R_1$ and $R_5$ are independently selected from hydrogen and fluorine, $R_2$ and $R_4$ are hydrogen, $R_3$ is Cl, E is O, and $R_7$, $R_8$ and $R_9$ are selected from hydrogen and fluorine; $R_1$ and $R_5$ are independently selected from hydrogen and fluorine, $R_2$ and $R_4$ are hydrogen, $R_3$ is Br, E is O, and $R_7$, $R_8$ and $R_9$ are selected from hydrogen and fluorine; $R_1$ and $R_5$ are independently selected from hydrogen and chlorine, $R_2$ and $R_4$ are hydrogen, $R_3$ is Cl, E is O, and $R_7$, $R_8$ and $R_9$ are selected from hydrogen and fluorine.

Also described herein are compounds having Formula VIb or a salt thereof,

Formula VIb wherein, $R_1$ and $R_5$ are independently selected from hydrogen, $CH_3$, F, Cl, Br, $CF_3$, and $OCF_3$;

$R_2$ and $R_4$ are independently selected from hydrogen, F, Cl, Br, and $CF_3$;

$R_3$ is selected from hydrogen, $CH_3$, $CF_3$, F, Cl, Br, $OCF_3$, $OCH_3$, CN, and C(H)O;

$R_8$ is selected from hydrogen and fluorine;

$R_6$ and $R_9$ are independently selected from hydrogen, F, Cl, $CH_3$, and $OCF_3$; and E is O or S.

In various embodiments of the compound of Formula VIb: $R_1$ and $R_5$ are independently selected from hydrogen, $CH_3$, F and $C_1$; $R_1$ and $R_5$ are independently selected from hydrogen, $CH_3$, fluorine and $C_1$, and $R_3$ is $C_1$; $R_1$ and $R_5$ are independently selected from hydrogen, $CH_3$, fluorine and $C_1$, and $R_3$ is Br; $R_1$ and $R_5$ are independently selected from hydrogen, $CH_3$, fluorine and Cl, $R_3$ is $C_1$, and E is O; $R_1$ and $R_5$ are independently selected from hydrogen, $CH_3$, fluorine and $C_1$, and $R_3$ is Br and E is O; $R_1$ and $R_5$ are independently selected from hydrogen and $CH_3$, and $R_3$ is Cl, E is O, and $R_6$, $R_8$ and $R_9$ are selected from hydrogen and fluorine; $R_1$ and $R_5$ are independently selected from hydrogen and $CH_3$, and $R_3$ is Br, E is O, and $R_7$, $R_8$ and $R_9$ are selected from hydrogen and fluorine; $R_1$ and $R_5$ are independently selected from hydrogen and fluorine, and $R_3$ is Cl, E is O, and $R_7$, $R_8$ and $R_9$ are selected from hydrogen and fluorine; $R_1$ and $R_5$ are independently selected from hydrogen and fluorine, $R_3$ is Br, E is O, and $R_7$, $R_8$ and $R_9$ are selected from hydrogen and fluorine; $R_1$ and $R_5$ are independently selected from hydrogen and chlorine, and $R_3$ is Cl, E is O, and $R_7$, $R_8$ and $R_9$ are selected from hydrogen and fluorine; $R_1$ and $R_5$ are independently selected from hydrogen and $CH_3$, $R_3$ is Cl, $R_2$ and $R_4$ are hydrogen E is O, and $R_7$, $R_8$ and $R_9$ are selected from hydrogen and fluorine; $R_1$ and $R_5$ are independently selected from hydrogen and $CH_3$, $R_2$ and $R_4$ are hydrogen, $R_3$ is Br, E is O, and $R_7$, $R_8$ and $R_9$ are selected from hydrogen and fluorine; $R_1$ and $R_5$ are independently selected from hydrogen and fluorine, $R_2$ and $R_4$ are hydrogen, $R_3$ is Cl, E is O, and $R_7$, $R_8$ and $R_9$ are selected from hydrogen and fluorine; $R_1$ and $R_5$ are independently selected from hydrogen and fluorine, $R_2$ and $R_4$ are hydrogen, $R_3$ is Br, E is O, and $R_7$, $R_8$ and $R_9$ are selected from hydrogen and fluorine; $R_1$ and $R_5$ are independently selected from hydrogen and chlorine, $R_2$ and $R_4$ are hydrogen, $R_3$ is Cl, E is O, and $R_7$, $R_8$ and $R_9$ are selected from hydrogen and fluorine.

Described herein are compounds having Formula (VII) or a salt thereof

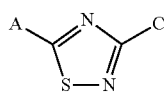

Formula VII wherein,

A is an optionally substituted aryl or optionally independently singly or multiply substituted arylalkyl (e.g., aryl$C_{1-3}$alkyl or aryl$C_1$-$C_6$) or optionally independently singly or multiply substituted heteroaryl or optionally independently singly or multiply substituted heteroarylalkyl (e.g., heteroaryl $C_{1-3}$alkyl or heteroaryl $C_1$-$C_6$) wherein the substituents are selected from the group consisting of halo, $C_1$-$C_6$ haloalkyl, $C_6$-$C_{10}$ aryl, $C_4$-$C_7$ cycloalkyl, $C_2$-$C_6$ alkyl, $C_2$-$C_6$ alkenyl, $C_2$-$C_6$ alkynyl, $C_6$-$C_{10}$ aryl($C_1$-$C_6$)alkyl, $C_6$-$C_{10}$ aryl($C_2$-$C_6$)alkenyl, $C_6$-$C_{10}$ aryl($C_2$-$C_6$) alkynyl, $C_1$-$C_6$ hydroxyalkyl, amino, ureido, cyano, $C_1$-$C_6$ acylamino, hydroxy, thiol, $C_1$-$C_6$ acyloxy, azido, $C_1$-$C_6$ alkoxy and carboxy, C(H)O;

C is a thienyl, furanyl, oxazolyl or isoxazolyl each of which can be optionally independently substituted with one or more with substituents selected from: fluorine, chlorine, $CH_3$, and $OCF_3$.

In various embodiments: A is aryl; A is arylalkyl; A is heteroarylalkyl; A is heteroaryl; C is thienyl; C is furanyl; C is oxazolyl; C is isoxazolyl; A is pyridyl; A is pyrazyl; A is oxazolyl; and A is isoxazolyl; both A and C are not thiophenyl; and both A and C are not furanyl.

Also described herein is a compound having Formula VIIa or a salt thereof,

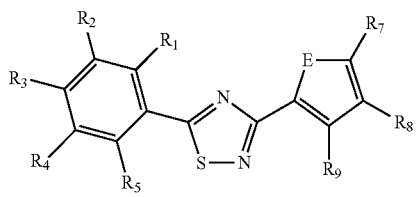

Formula VIIa wherein, $R_1$ and $R_5$ are independently selected from hydrogen, $CH_3$, F, Cl, Br, $CF_3$, and $OCF_3$;

$R_2$ and $R_4$ are independently selected from hydrogen, F, Cl, Br, and $CF_3$;

$R_3$ is selected from hydrogen, $CH_3$, $CF_3$, F, Cl, Br, $OCF_3$, $OCH_3$, CN, and C(H)O;

$R_7$ and $R_8$ are independently selected from hydrogen and fluorine;

$R_9$ is selected from hydrogen, F, Cl, $CH_3$, and $OCF_3$;

E is O or S.

In various embodiments of the compound of Formula VIIa: $R_1$ and $R_5$ are independently selected from hydrogen, $CH_3$, F and $C_1$; $R_1$ and $R_5$ are independently selected from hydrogen, $CH_3$, fluorine and $C_1$, and $R_3$ is $C_1$; $R_1$ and $R_5$ are independently selected from hydrogen, $CH_3$, fluorine and $C_1$, and $R_3$ is Br, $R_1$ and $R_5$ are independently selected from hydrogen, $CH_3$, fluorine and Cl, $R_3$ is $C_1$, and E is O; $R_1$ and $R_5$ are independently selected from hydrogen, $CH_3$, fluorine and $C_1$, and $R_3$ is Br and E is O; $R_1$ and $R_5$ are independently selected from hydrogen and $CH_3$, and $R_3$ is Cl, E is O, and $R_6$, $R_8$ and $R_9$ are selected from hydrogen and fluorine; $R_1$ and $R_5$ are independently selected from hydrogen and $CH_3$, and $R_3$ is Br, E is O, and $R_7$, $R_8$ and $R_9$ are selected from hydrogen and fluorine; $R_1$ and $R_5$ are independently selected from hydrogen and fluorine, and $R_3$ is Cl, E is O, and $R_7$, $R_8$ and $R_9$ are selected from hydrogen and fluorine; $R_1$ and $R_5$ are independently selected from hydrogen and fluorine, $R_3$ is Br, E is O, and $R_7$, $R_8$ and $R_9$ are selected from hydrogen and fluorine; $R_1$ and $R_5$ are independently selected from hydrogen and chlorine, and $R_3$ is Cl, E is O, and $R_7$, $R_8$ and $R_9$ are selected from hydrogen and fluorine; $R_1$ and $R_5$ are independently selected from hydrogen and $CH_3$, $R_3$ is Cl, $R_2$ and $R_4$ are hydrogen E is O, and $R_7$, $R_8$ and $R_9$ are selected from hydrogen and fluorine; $R_1$ and $R_5$ are independently selected from hydrogen and $CH_3$, $R_2$ and $R_4$ are hydrogen, $R_3$ is Br, E is O, and $R_7$, $R_8$ and $R_9$ are selected from hydrogen and fluorine; $R_1$ and $R_5$ are independently selected from hydrogen and fluorine, $R_2$ and $R_4$ are hydrogen, $R_3$ is Cl, E is O, and $R_7$, $R_8$ and $R_9$ are selected from hydrogen and fluorine; $R_1$ and $R_5$ are independently selected from hydrogen and fluorine, $R_2$ and $R_4$ are hydrogen, $R_3$ is Br, E is O, and $R_7$, $R_8$ and $R_9$ are selected from hydrogen and fluorine; $R_1$ and $R_5$ are independently selected from hydrogen and chlorine, $R_2$ and $R_4$ are hydrogen, $R_3$ is Cl, E is O, and $R_7$, $R_8$ and $R_9$ are selected from hydrogen and fluorine.

Also described herein is a compound having Formula VIIb or a salt thereof,

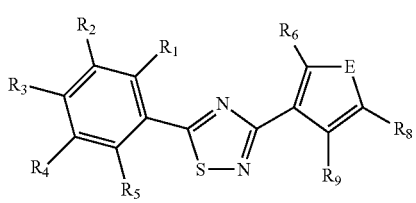

Formula VIIb wherein, $R_1$ and $R_5$ are independently selected from hydrogen, $CH_3$, F, Cl, Br, $CF_3$ and $OCF_3$;

$R_2$ and $R_4$ are independently selected from hydrogen, F, Cl, Br, and $CF_3$;

$R_3$ is selected from hydrogen, $CH_3$, $CF_3$, F, Cl, Br, $OCF_3$, $OCH_3$, CN, and C(H)O;

$R_8$ is selected from hydrogen and fluorine;

$R_6$ and $R_9$ are independently selected from hydrogen, F, Cl, $CH_3$, and $OCF_3$; and E is O or S.

In various embodiments of the compound of Formula VIIa: $R_1$ and $R_5$ are independently selected from hydrogen, $CH_3$, F and $C_1$; $R_1$ and $R_5$ are independently selected from hydrogen, $CH_3$, fluorine and $C_1$, and $R_3$ is $C_1$; $R_1$ and $R_5$ are independently selected from hydrogen, $CH_3$, fluorine and $C_1$, and $R_3$ is Br; $R_1$ and $R_5$ are independently selected from hydrogen, $CH_3$, fluorine and Cl, $R_3$ is $C_1$, and E is O; $R_1$ and $R_5$ are independently selected from hydrogen, $CH_3$, fluorine and $C_1$, and $R_3$ is Br and E is O; $R_1$ and $R_5$ are independently selected from hydrogen and $CH_3$, and $R_3$ is Cl, E is O, and $R_6$, $R_8$ and $R_9$ are selected from hydrogen and fluorine; $R_1$ and $R_5$ are independently selected from hydrogen and $CH_3$, and $R_3$ is Br, E is O, and $R_7$, $R_8$ and $R_9$ are selected from hydrogen and fluorine; $R_1$ and $R_5$ are independently selected from hydrogen and fluorine, and $R_3$ is Cl, E is O, and $R_7$, $R_8$ and $R_9$ are selected from hydrogen and fluorine; $R_1$ and $R_5$ are independently selected from hydrogen and fluorine, $R_3$ is Br, E is O, and $R_7$, $R_8$ and $R_9$ are selected from hydrogen and fluorine; $R_1$ and $R_5$ are independently selected from hydrogen and chlorine, and $R_3$ is Cl, E is O, and $R_7$, $R_8$ and $R_9$ are selected from hydrogen and fluorine; $R_1$ and $R_5$ are independently selected from hydrogen and $CH_3$, $R_3$ is Cl, $R_2$ and $R_4$ are hydrogen E is O, and $R_7$, $R_8$ and $R_9$ are selected from hydrogen and fluorine; $R_1$ and $R_5$ are independently selected from hydrogen and $CH_3$, $R_2$ and $R_4$ are hydrogen, $R_3$ is Br, E is O, and $R_7$, $R_8$ and $R_9$ are selected from hydrogen and fluorine; $R_1$ and $R_5$ are independently selected from hydrogen and fluorine, $R_2$ and $R_4$ are hydrogen, $R_3$ is Cl, E is O, and $R_7$, $R_8$ and $R_9$ are selected from hydrogen and fluorine; $R_1$ and $R_5$ are independently selected from hydrogen and fluorine, $R_2$ and $R_4$ are hydrogen, $R_3$ is Br, E is O, and $R_7$, $R_8$ and $R_9$ are selected from hydrogen and fluorine; $R_1$ and $R_5$ are independently selected from hydrogen and chlorine, $R_2$ and $R_4$ are hydrogen, $R_3$ is Cl, E is O, and $R_7$, $R_8$ and $R_9$ are selected from hydrogen and fluorine.

Also described herein is a method for control of unwanted nematodes, the method comprising administering to mammals, birds, or their food, plants, seeds or soil a composition comprising an effective amount of a compound of any of Formulas I, Ia, Ib, II, IIa, IIb, III, IIIa, IIIb, IV, IVa, IVb, V, Va, Vb, VI, VIa, VIb, VII, VIIa and VIIb without the provisos.

Also described herein is a method for control of unwanted nematodes, the method comprising administering to mammals, birds, or their food, plants, seeds or soil a composition comprising an effective amount of a compound of any of Formulas I, Ia, Ib, II, IIa, IIb, III, IIIa, IIIb, IV, IVa, IVb, V, Va, Vb, VI, VIa, VIb, VII, VIIa and VIIb with the provisos.

Also described is a nematicidal composition comprising a compound of any of Formulas I, Ia, Ib, II, IIa, IIb, III, IIIa, IIIb, IV, IVa, IVb, V, Va, Vb, VI, VIa, VIb, VII, VIIa and VIIb without the provisos. at a concentration sufficient to reduce the viability of a parasitic nematode.

Also described is a nematicidal composition comprising a compound of any of Formulas I, Ia, Ib, II, IIa, IIb, III, IIIa, IIIb, IV, IVa, IVb, V, Va, Vb, VI, VIa, VIb, VII, VIIa and VIIb with the provisos at a concentration sufficient to reduce the viability of a parasitic nematode.

In some cases, the nematicidal composition further includes an aqueous surfactant. Examples of surfactants that can be used include, Span 20, Span 40, Span 80, Span 85, Tween 20, Tween 40, Tween 80, Tween 85, Triton X 100, Makon 10, Igepal CO 630, Brij 35, Brij 97, Tergitol TMN 6, Dowfax 3B2, Physan and Toximul TA 15. In some cases, the nematicidal composition further includes a permeation enhancer (e.g., cyclodextrin). In some cases, the nematicidal composition further includes a co-solvent. Examples of co-solvents that can be used include ethyl lactate, methyl soyate/ethyl lactate co-solvent blends (e.g., Steposol), isopropanol, acetone, 1,2-propanediol, n-alkylpyrrolidones (e.g., the Agsolex series), a petroleum based-oil (e.g., aromatic 200) or a mineral oil (e.g., paraffin oil)). In some cases, the nematicidal composition further includes another pesticide (e.g., nematicide, insecticide or fungicide) such as an avermectin (e.g., ivermectin), milbemycin, imidacloprid, aldicarb, oxamyl, fenamiphos, fosthiazate, metam sodium, etridiazole, penta-chloro-nitrobenzene (PCNB), flutolanil, metalaxyl, mefonoxam, and fosetyl-al. Useful fungicides include, but are not limited to, silthiofam, fludioxonil, myclobutanil, azoxystrobin, chlorothalonil, propiconazole, tebuconazole and pyraclostrobin. The composition may also comprise herbicides (e.g., trifloxysulfuron, glyphosate, halosulfuron) and other chemicals for disease control (e.g., chitosan).

Also described is a nematicidal composition comprising: oxazole, oxadiazole or thiadiazole analogs or mixtures of analogs selected from the group consisting of the compounds 3-phenyl-5-(thiophen-2-yl)-1,2,4-oxadiazole, 3-(4-fluorophenyl)-5-(thiophen-2-yl)-1,2,4-oxadiazole, 3-(4-chlorophenyl)-5-(furan-2-yl)-1,2,4-oxadiazole, 3-(4-chlorophenyl)-5-(thiophen-2-yl)-1,2,4-oxadiazole, 3-(4-chloro-2-methylphenyl)-5-(furan-2-yl)-1,2,4-oxadiazole, 5-(4-chloro-2-methylphenyl)-3-(furan-2-yl)-1,2,4-oxadiazole, 3-(4-bromo-2-methylphenyl)-5-(furan-2-yl)-1,2,4-oxadiazole, 3-(4-fluoro-2-methylphenyl)-5-(thiophen-2-yl)-1,2,4-oxadiazole, difluorophenyl)-5-(thiophen-2-yl)-1,2,4-oxadiazole, 3-(4-bromo-2-fluorophenyl)-5-(thiophen-2-yl)-1,2,4-oxadiazole, 5-(thiophen-2-yl)-3-(2,4,6-trifluorophenyl)-1,2,4-oxadiazole, 3-(2,4-dichlorophenyl)-5-(furan-2-yl)-1,2,4-oxadiazole, 3-(4-bromo-2-chlorophenyl)-5-(furan-2-yl)-1,2,4-oxadiazole, 3-(2-chloro-4-fluorophenyl)-5-(thiophen-2-yl)-1,2,4-oxadiazole, 3-(4-chlorophenyl)-5-(thiophen-2-yl)-1,2,4-thiadiazole, 3-(4-chlorophenyl)-5-(furan-2-yl)-1,2,4-thiadiazole, 3-(4-chlorophenyl)-5-(3-methylfuran-2-yl)-1,2,4-oxadiazole, 5-(4-chloro-2-fluorophenyl)-2-(thiophen-2-yl)oxazole, 2-(4-chloro-2-fluorophenyl)-5-(thiophen-2-yl)oxazole, 5-(4-chloro-2-fluorophenyl)-2-(furan-2-yl)oxazole, 5-(4-chloro-2-methylphenyl)-2-(furan-3-yl)oxazole, 3-(4-chloro-2-methylphenyl)-5-(furan-2-yl)-1,2,4-thiadiazole, 5-(4-chloro-2-methylphenyl)-3-(furan-2-yl)-1,2,4-thiadiazole, 3-(4-bromo-2-methylphenyl)-5-(furan-2-yl)-1,2,4-thiadiazole, 5-(furan-2-yl)-3-(4-methoxy-2-methylphenyl)-1,2,4-oxadiazole, 3-(6-chloropyridin-3-yl)-5-(thiophen-2-yl)-1,2,4-thiadiazole, 3-(6-chloropyridin-3-yl)-5-(furan-2-yl)-1,2,4-thiadiazole, 5-(2,4-difluorophenyl)-2-(thiophen-2-yl)oxazole, 5-(2,4-difluorophenyl)-2-(furan-2-yl)oxazole, 5-(4-bromo-2-fluorophenyl)-2-(thiophen-2-yl)oxazole, 5-(4-bromo-2-fluorophenyl)-2-(furan-2-yl)oxazole, 3-(2,4-difluorophenyl)-5-(furan-2-yl)-1,2,4-thiadiazole, 3-(4-chlorophenyl)-5-(furan-2-yl)-1,2,4-thiadiazole, 3-(4-bromo-2-fluorophenyl)-5-(furan-2-yl)-1,2,4-thiadiazole, 3-(2,4-difluorophenyl)-5-(thiophen-2-yl)-1,2,4-thiadiazole, 3-(4-chloro-2-fluorophenyl)-5-(thiophen-2-yl)-1,2,4-thiadiazole, 3-(4-bromo-2-fluorophenyl)-5-(thiophen-2-yl)-1,2,4-thiadiazole, 5-(furan-2-yl)-3-(4-methoxy-2-methylphenyl)-1,2,4-thiadiazole, 3-(2,4-dichlorophenyl)-5-(furan-2-yl)-1,2,4-thiadiazole, 3-(4-bromo-2-chlorophenyl)-5-(furan-2-yl)-1,2,4-thiadiazole, 3-(2,6-dichloropyridin-3-yl)-5-(furan-2-yl)-1,2,4-thiadiazole, 5-(2,4-dichlorophenyl)-2-(thiophen-2-yl)oxazole, 3-(4-chlorophenyl)-5-(thiophen-3-yl)-1,2,4-oxadiazole, 5-(4-chloro-2-methylphenyl)-2-(furan-3-yl)oxazole.

In various embodiments the composition further comprises an aqueous surfactant. Examples of surfactants that can be used include, Span 20, Span 40, Span 80, Span 85, Tween 20, Tween 40, Tween 80, Tween 85, Triton X 100, Makon 10, Igepal CO 630, Brij 35, Brij 97, Tergitol TMN 6, Dowfax 3B2, Physan and Toximul TA 15. In some cases, the nematicidal composition further includes a permeation enhancer (e.g., cyclodextrin). In some cases, the nematicidal composition further includes a co-solvent. Examples of co-solvents that can be used include ethyl lactate, methyl soyate/ethyl lactate co-solvent blends (e.g., Steposol), isopropanol, acetone, 1,2-propanediol, n-alkylpyrrolidones (e.g., the Agsolex series), a petroleum based-oil (e.g., aromatic 200) or a mineral oil (e.g., paraffin oil)). In some cases, the nematicidal composition further includes another pesticide (e.g., nematicide, insecticide or fungicide) such as an avermectin (e.g., ivermectin), milbemycin, imidacloprid, aldicarb, oxamyl, fenamiphos, fosthiazate, metam sodium, etridiazole, penta-chloro-nitrobenzene (PCNB), flutolanil, metalaxyl, mefonoxam, and fosetyl-al. Useful fungicides include, but are not limited to, silthiofam, fludioxonil, myclobutanil, azoxystrobin, chlorothalonil, propiconazole, tebuconazole and pyraclostrobin. The composition may also comprise herbicides (e.g., trifloxysulfuron, glyphosate, halosulfuron) and other chemicals for disease control (e.g., chitosan).

Also described is a method for control of unwanted parasitic nematode (e.g., nematodes other than C. elegans), the method including administering to vertebrates, plants, seeds or soil a nematicidal composition including a compound of any of the formulae described herein in any of the nematicidal compositions described herein.

In some instances, the nematode infects plants and the nematicidal composition is applied to the soil or to plants. In some instances, the nematicidal composition is applied to soil before planting. In some instances, the nematicidal composition is applied to soil after planting. In some instances, the nematicidal composition is applied to soil using a drip system. In some instances, the nematicidal composition is applied to soil using a drench system. In some instances, the nematicidal composition is applied to plant roots or plant foliage (e.g., leaves, stems). In some instances the nematicide composition is tilled into the soil or applied in furrow. In some instances, the nematicidal composition is applied to seeds. In some instances, the nematode parasite infects a vertebrate. In some instances, the nematicidal composition is administered to non-human vertebrate. In some instances, the nematicidal composition is administered to a human. In some instances, the nematicidal composition is formulated as a drench to be administered to a non-human animal. In some instances, the nematicidal composition is formulated as an orally administered drug. In some instances, the nematicidal composition is formulated as an injectable drug. In some instances, the nematicidal composition is formulated for topical applications such as pour-ons, or for the use in tags or collars.

Also described herein is a method of treating a disorder (e.g., an infection) caused by a parasitic nematode, (e.g., M. incognita, H. glycines, B. longicaudatus, H. contortus, A. suum, B. malayi) in a subject, e.g., a host plant, animal, or person. The method includes administering to the subject an effective amount of a compound having Formula I, Ia, Ib, II, IIa, IIb, III, IIIa, IIIb, IV, IVa, IVb, V, Va, Vb, VI, VIa, VIb, VII, VIIa or VIIb. The compound may be delivered by several means including pre-planting, post-planting and as a feed additive, drench, external application, pill or by injection.

In still another aspect, methods of inhibiting a parasitic nematode (e.g., M. incognita, H. glycines, B. longicaudatus, H. contortus, A. suum, B. malayi) are provided. Such methods can include contacting the nematode (at any stage of growth), with a compound, e.g., a compound having Formula I, Ia, Ib, II, IIa, IIb, III, IIIa, IIIb, IV, IVa, IVb, V, Va, Vb, VI, VIa, VIb, VII, VIIa or VIIb is provided.

In another aspect, methods of reducing the viability or fecundity or slowing the growth or development or inhibiting the infectivity of a nematode using a nematicidal compound, e.g., a compound having Formula I, Ia, Ib, II, IIa, IIb, III, IIIa, IIIb, IV, IVa, IVb, V, Va, Vb, VI, VIa, VIb, VII, VIIa or VIIb is provided. Such methods can include contacting the nematode with specific a compound, e.g., a compound having Formula I, Ia, Ib, II, IIa, IIb, III, IIIa, IIIb, IV, IVa, IVb, V, Va, Vb, VI, VIa, VIb, VII, VIIa or VIIb; (c) reducing the viability or fecundity of the nematode parasite.

Also described is a method for reducing the viability, growth, or fecundity of a nematode parasite, the method comprising exposing the nematode to a compound having Formula I, Ia, Ib, II, IIa, IIb, III, IIIa, IIIb, IV, IVa, IVb, V, Va, Vb, VI, VIa, VIb, VII, VIIa or VIIb and a method of protecting a plant from a nematode infection, the method comprising applying to the plant, to the soil, or to seeds of the plant an compound a compound having Formula I, Ia, Ib, II, IIa, IIb, III, IIIa, IIIb, IV, IVa, IVb, V, Va, Vb, VI, VIa, VIb, VII, VIIa or VIIb.

Also described is a method for protecting a vertebrate (e.g., a bird or a mammal) from a nematode infection, the method comprising administering to the vertebrate a compound having I, Ia, Ib, II, IIa, IIb, III, IIIa, IIIb, IV, IVa, IVb, V, Va, Vb, VI, VIa, VIb, VII, VIIa or VIIb. The bird can be a domesticated fowl (e.g., a chicken, turkey, duck, or goose). The mammal can be a domesticated animal, e.g., a companion animal (e.g., a cat, dog, horse or rabbit) or livestock (e.g., a cow, sheep, pig, goat, alpaca or llama) or can be a human.

Described herein are methods for controlling nematodes parasites by administering a compound described herein. The methods include administering to vertebrates, plants, seeds or soil a nematicidal composition comprising:

an effective amount of a compound or a mixture of compounds having any of the formulae described herein, for example one of the following formulas:

Formulas:

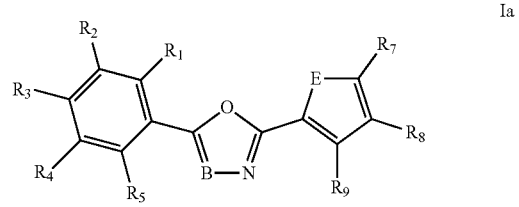

Ia

Formulas:

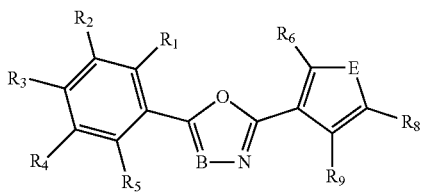
Ib

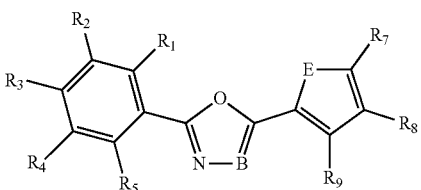
IIa

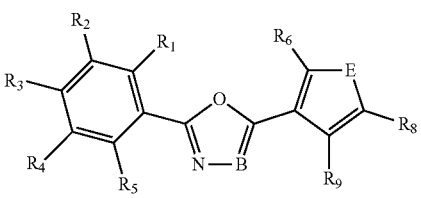
IIb

Formulas:

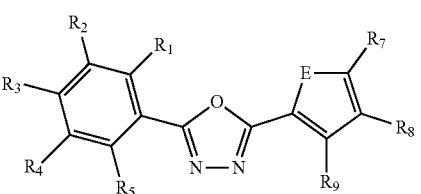
IIIa

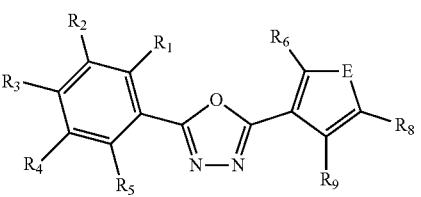
IIIb

Formulas:

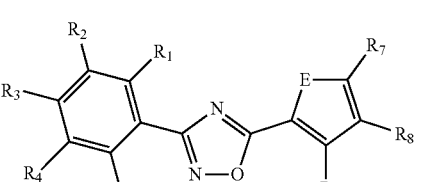
IVa

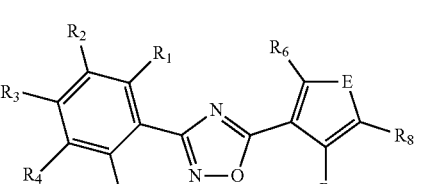
IVb

Formulas:

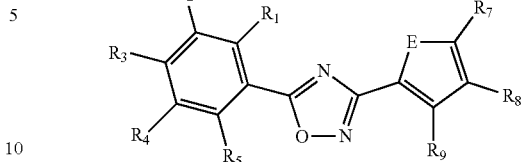
Va

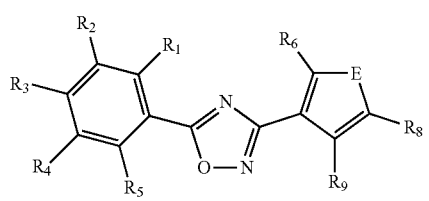
Vb

Formulas:

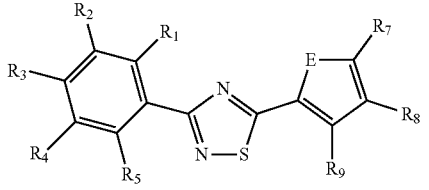
VIa

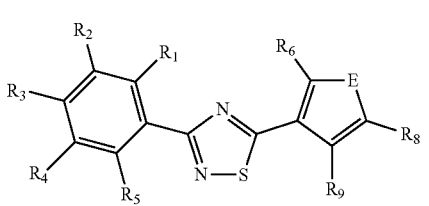
VIb

Formulas:

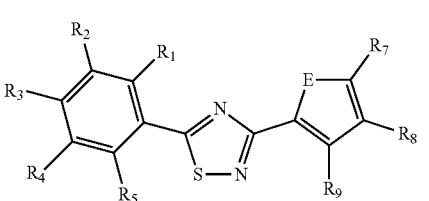
VIIa

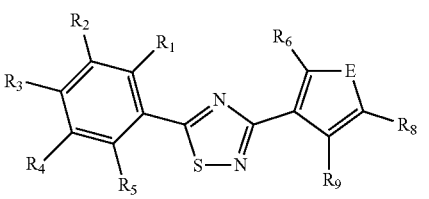
VIIb wherein, $R_1$ and $R_5$ are independently selected from hydrogen, $CH_3$, F, Cl, Br, $CF_3$, and $OCF_3$;

$R_2$ and $R_4$ are independently selected from hydrogen, F, Cl, Br, and $CF_3$;

$R_3$ is selected from hydrogen, $CH_3$, $CF_3$, F, Cl, Br, $OCF_3$, $OCH_3$, CN, and CO;

$R_8$ is selected from hydrogen and fluorine;

$R_6$ and $R_9$ are independently selected from hydrogen, F, Cl, $CH_3$, and $OCF_3$;

B is C(H) or C($CH_3$);

E is O or S.

In some cases, $R_1$ and $R_5$ are not both H.

The compositions can also include an aqueous surfactant. Examples of surfactants that can be used include, Span 20, Span 40, Span 80, Span 85, Tween 20, Tween 40, Tween 80, Tween 85, Triton X 100, Makon 10, Igepal CO 630, Brij 35, Brij 97, Tergitol TMN 6, Dowfax 3B2, Physan and Toximul TA 15. In some cases, the nematicidal composition further includes a permeation enhancer (e.g., cyclodextrin). In some cases, the nematicidal composition further includes a co-solvent. Examples of co-solvents that can be used include ethyl lactate, methyl soyate/ethyl lactate co-solvent blends (e.g., Steposol), isopropanol, acetone, 1,2-propanediol, n-alkylpyrrolidones (e.g., the Agsolex series), a petroleum based-oil (e.g., aromatic 200) or a mineral oil (e.g., paraffin oil)). In some cases, the nematicidal composition further includes another pesticide (e.g., nematicide, insecticide or fungicide) such as an avermectin (e.g., ivermectin), milbemycin, imidacloprid, aldicarb, oxamyl, fenamiphos, fosthiazate, metam sodium, etridiazole, penta-chloro-nitrobenzene (PCNB), flutolanil, metalaxyl, mefonoxam, and fosetyl-al. Useful fungicides include, but are not limited to, silthiofam, fludioxonil, myclobutanil, azoxystrobin, chlorothalonil, propiconazole, tebuconazole and pyraclostrobin. The composition may also comprise herbicides (e.g., trifloxysulfuron, glyphosate, halosulfuron) and other chemicals for disease control (e.g., chitosan).

Also featured is a method for control of unwanted nematodes comprising administering to vertebrates, plants, seeds or soil a nematicidal composition comprising an effective amount of: (a) a compound selected from the group consisting of 3-phenyl-5-(thiophen-2-yl)-1,2,4-oxadiazole, 3-(4-fluorophenyl)-5-(thiophen-2-yl)-1,2,4-oxadiazole, 3-(4-chlorophenyl)-5-(furan-2-yl)-1,2,4-oxadiazole, 3-(4-chlorophenyl)-5-(thiophen-2-yl)-1,2,4-oxadiazole, 3-(4-chloro-2-methylphenyl)-5-(furan-2-yl)-1,2,4-oxadiazole, 5-(4-chloro-2-methylphenyl)-3-(furan-2-yl)-1,2,4-oxadiazole, 3-(4-bromo-2-methylphenyl)-5-(furan-2-yl)-1,2,4-oxadiazole, 3-(4-fluoro-2-methylphenyl)-5-(thiophen-2-yl)-1,2,4-oxadiazole, difluorophenyl)-5-(thiophen-2-yl)-1,2,4-oxadiazole, 3-(4-bromo-2-fluorophenyl)-5-(thiophen-2-yl)-1,2,4-oxadiazole, 5-(thiophen-2-yl)-3-(2,4,6-trifluorophenyl)-1,2,4-oxadiazole, 3-(2,4-dichlorophenyl)-5-(furan-2-yl)-1,2,4-oxadiazole, 3-(4-bromo-2-chlorophenyl)-5-(furan-2-yl)-1,2,4-oxadiazole, 3-(2-chloro-4-fluorophenyl)-5-(thiophen-2-yl)-1,2,4-oxadiazole, 3-(4-chlorophenyl)-5-(thiophen-2-yl)-1,2,4-thiadiazole, 3-(4-chlorophenyl)-5-(furan-2-yl)-1,2,4-thiadiazole, 3-(4-chlorophenyl)-5-(3-methylfuran-2-yl)-1,2,4-oxadiazole, 5-(4-chloro-2-fluorophenyl)-2-(thiophen-2-yl)oxazole, 2-(4-chloro-2-fluorophenyl)-5-(thiophen-2-yl)oxazole, 5-(4-chloro-2-fluorophenyl)-2-(furan-2-yl)oxazole, 5-(4-chloro-2-methylphenyl)-2-(furan-3-yl)oxazole, 3-(4-chloro-2-methylphenyl)-5-(furan-2-yl)-1,2,4-thiadiazole, 5-(4-chloro-2-methylphenyl)-3-(furan-2-yl)-1,2,4-thiadiazole, 3-(4-bromo-2-methylphenyl)-5-(furan-2-yl)-1,2,4-thiadiazole, 5-(furan-2-yl)-3-(4-methoxy-2-methylphenyl)-1,2,4-oxadiazole, 3-(6-chloropyridin-3-yl)-5-(thiophen-2-yl)-1,2,4-thiadiazole, 3-(6-chloropyridin-3-yl)-5-(furan-2-yl)-1,2,4-thiadiazole, 5-(2,4-difluorophenyl)-2-(thiophen-2-yl)oxazole, 5-(2,4-difluorophenyl)-2-(furan-2-yl)oxazole, 5-(4-bromo-2-fluorophenyl)-2-(thiophen-2-yl)oxazole, 5-(4-bromo-2-fluorophenyl)-2-(furan-2-yl)oxazole, 3-(2,4-difluorophenyl)-5-(furan-2-yl)-1,2,4-thiadiazole, 3-(4-chloro-2-fluorophenyl)-5-(furan-2-yl)-1,2,4-thiadiazole, 3-(4-bromo-2-fluorophenyl)-5-(furan-2-yl)-1,2,4-thiadiazole, 3-(2,4-difluorophenyl)-5-(thiophen-2-yl)-1,2,4-thiadiazole, 3-(4-chloro-2-fluorophenyl)-5-(thiophen-2-yl)-1,2,4-thiadiazole, 3-(4-bromo-2-fluorophenyl)-5-(thiophen-2-yl)-1,2,4-thiadiazole, 5-(furan-2-yl)-3-(4-methoxy-2-methylphenyl)-1,2,4-thiadiazole, 3-(2,4-dichlorophenyl)-5-(furan-2-yl)-1,2,4-thiadiazole, 3-(4-bromo-2-chlorophenyl)-5-(furan-2-yl)-1,2,4-thiadiazole, 3-(2,6-dichloropyridin-3-yl)-5-(furan-2-yl)-1,2,4-thiadiazole, 5-(2,4-dichlorophenyl)-2-(thiophen-2-yl)oxazole, 3-(4-chlorophenyl)-5-(thiophen-3-yl)-1,2,4-oxadiazole, 5-(4-chloro-2-methylphenyl)-2-(furan-3-yl)oxazole.

Also featured is a method for control of unwanted nematodes comprising administering to vertebrates a nematicidal composition comprising an effective amount of: (a) a compound selected from the group consisting of 5-(4-bromophenyl)-2-(thiophen-2-yl)oxazole, 2-(2-fluorophenyl)-5-(furan-2-yl)oxazole, 5-(isoxazol-5-yl)-3-(4-(trifluoromethoxy)phenyl)-1,2,4-oxadiazole, 2-phenyl-5-p-tolyl-1,3,4-oxadiazole, 5-(4-fluorophenyl)-2-(thiophen-2-yl)oxazole, 5-(furan-2-yl)-3-p-tolyl-1,2,4-oxadiazole, 2-(4-chlorophenyl)-5-(thiophen-2-yl)oxazole, 2-(3-methoxyphenyl)-5-phenyl-1,3,4-oxadiazole, 5-(4-bromophenyl)-2-(furan-2-yl)oxazole, 5-(4-chlorophenyl)-2-(thiophen-3-yl)oxazole, 2-(furan-2-yl)-5-phenyloxazole, 5-(4-chlorophenyl)-2-(furan-2-yl)oxazole, 5-(furan-2-yl)-3-(4-iodophenyl)-1,2,4-oxadiazole, 5-(furan-2-yl)-3-(oxazol-2-yl)-1,2,4-oxadiazole, 5-(4-propylphenyl)-3-(thiophen-2-yl)-1,2,4-oxadiazole, 2-(4-bromophenyl)-5-(thiophen-2-yl)oxazole, 3-(4-bromophenyl)-5-(furan-2-yl)-1,2,4-oxadiazole, 2-(3-chlorophenyl)-5-(thiophen-2-yl)oxazole.

In certain embodiments of the method the composition further comprises an aqueous surfactant. Examples of surfactants that can be used include, Span 20, Span 40, Span 80, Span 85, Tween 20, Tween 40, Tween 80, Tween 85, Triton X 100, Makon 10, Igepal CO 630, Brij 35, Brij 97, Tergitol TMN 6, Dowfax 3B2, Physan and Toximul TA 15. In some cases, the nematicidal composition further includes a permeation enhancer (e.g., cyclodextrin). In some cases, the nematicidal composition further includes a co-solvent. Examples of co-solvents that can be used include ethyl lactate, methyl soyate/ethyl lactate co-solvent blends (e.g., Steposol), isopropanol, acetone, 1,2-propanediol, n-alkylpyrrolidones (e.g., the Agsolex series), a petroleum based-oil (e.g., aromatic 200) or a mineral oil (e.g., paraffin oil)). In some cases, the nematicidal composition further includes another pesticide (e.g., nematicide, insecticide or fungicide) such as an avermectin (e.g., ivermectin), milbemycin, imidacloprid, aldicarb, oxamyl, fenamiphos, fosthiazate, metam sodium, etridiazole, penta-chloro-nitrobenzene (PCNB), flutolanil, metalaxyl, mefonoxam, and fosetyl-al. Useful fungicides include, but are not limited to, silthiofam, fludioxonil, myclobutanil, azoxystrobin, chlorothalonil, propiconazole, tebuconazole and pyraclostrobin. The composition may also comprise herbicides (e.g., trifloxysulfuron, glyphosate, halosulfuron) and other chemicals for disease control (e.g., chitosan); the nematode infects plants and the nematicidal composition is applied to the soil or to plants; the nematicidal composition is applied to soil before planting; the nematicidal composition is applied to soil after planting; the nematicidal composition is applied to soil using a drip system; the nematicidal composition is applied to soil using a drench system; the nematicidal composition is applied to plant roots; the pesticidal composition is applied to seeds; the nematicidal composition is applied to the foliage of plants; the nematode infects a vertebrate; the nematicidal composition is administered to a bird or non-human mammal; the nematicidal composition is administered to a human; the nematicidal composition is formulated as a drench to be administered to a non-human animal; the nematicidal composition is formulated as an orally administered drug; and the nematicidal composition is formulated as an injectable drug.

The methods described hereon are particularly valuable for the control nematodes attacking the roots of desired crop plants, ornamental plants, and turf grasses. The desired crop plants can be, for example, soybeans, cotton, corn, tobacco, wheat, strawberries, tomatoes, banana, sugar cane, sugar beet, potatoes, or citrus.

Also described is a nematicidal feed for a non-human vertebrate including:

a feed; and a nematicidal composition, including a nematicidal composition described herein.

In some instances, the feed is selected from the group consisting of: soy, wheat, corn, sorghum, millet, alfalfa, clover, and rye.

Also described are feeds that have been supplemented to include one or more of the compounds described herein.

A nematicidal feed for a non-human vertebrate can comprise: (a) an animal feed; and (b) an effective amount of a nematicidal compound or mixtures of compounds having any of the formulae described herein, for example having one of the formula below:

Formulas:

Ia

Ib

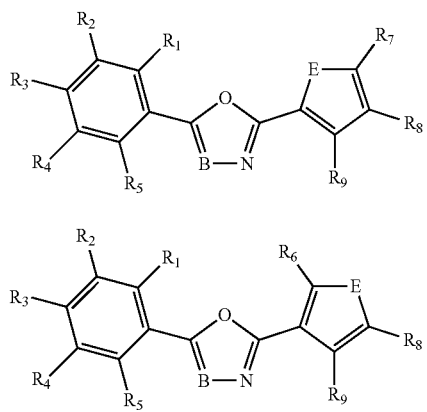

Formulas:

IIa

IIb

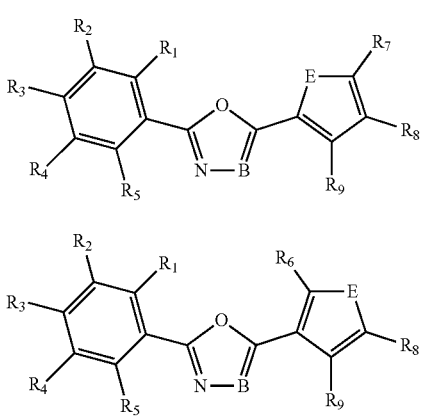

Formulas:

IIIa

IIIb

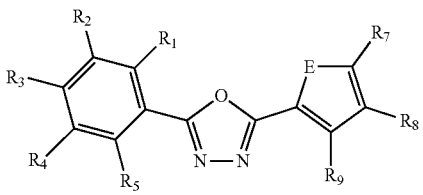

Formulas:

IVa

IVb

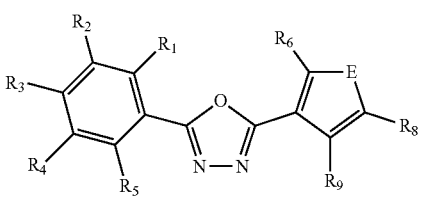

Formulas:

Va

Vb

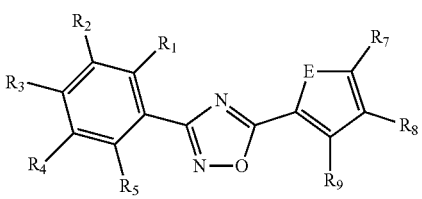

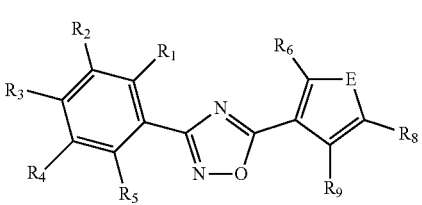

Formulas:

VIa

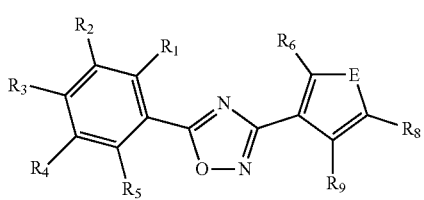

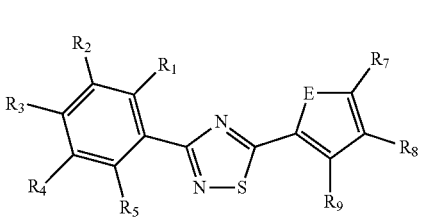

-continued

Formulas:

VIb

VIIa

VIIb wherein, $R_1$ and $R_5$ are independently selected from hydrogen, $CH_3$, F, Cl, Br, $CF_3$, and $OCF_3$;

$R_2$ and $R_4$ are independently selected from hydrogen, F, Cl, Br, and $CF_3$;

$R_3$ is selected from hydrogen, $CH_3$, $CF_3$, F, Cl, Br, $OCF_3$, $OCH_3$, CN, and CO;

$R_8$ is selected from hydrogen and fluorine;

$R_6$ and $R_9$ are independently selected from hydrogen, F, Cl, $CH_3$, and $OCF_3$;

B is C(H), or $C(CH_3)$;

E is O or S.

In some cases, $R_1$ and $R_5$ are not both H.

The feed can be selected from the group consisting of: soy, wheat, corn, sorghum, millet, alfalfa, clover, and rye.

As used herein, an agent with "anthelmintic or anthelminthic or antihelminthic activity" is an agent, which when tested, has measurable nematode-killing activity or results in reduced fertility or sterility in the nematodes such that fewer viable or no offspring result, or compromises the ability of the nematode to infect or reproduce in its host, or interferes with the growth or development of a nematode. The agent may also display nematode repellant properties. In the assay, the agent is combined with nematodes, e.g., in a well of microtiter dish, in liquid or solid media or in the soil containing the agent. Staged nematodes are placed on the media. The time of survival, viability of offspring, and/or the movement of the nematodes are measured. An agent with "anthelmintic or anthelminthic or antihelmthic activity" can, for example, reduce the survival time of adult nematodes relative to unexposed similarly staged adults, e.g., by about 20%, 40%, 60%, 80%, or more. In the alternative, an agent with "anthelmintic or anthelminthic or antihelminthic activity" may also cause the nematodes to cease replicating, regenerating, and/or producing viable progeny, e.g., by about 20%, 40%, 60%, 80%, or more. The effect may be apparent immediately or in successive generations.

The term "halo" or "halogen" refers to any radical of fluorine, chlorine, bromine or iodine.

The term "alkyl" as employed herein by itself or as part of another group refers to both straight and branched chain radicals of up to ten carbons. Typical $C_{1-10}$ alkyl groups include methyl, ethyl, propyl, isopropyl, butyl, sec-butyl, tert-butyl, 3-pentyl, hexyl and octyl groups, which may be optionally substituted.

The term "alkenyl" as employed herein by itself or as part of another group means a straight or branched chain radical of 2-10 carbon atoms, unless the chain length is limited thereto, including at least one double bond between two of the carbon atoms in the chain. Typical alkenyl groups include ethenyl, 1-propenyl, 2-propenyl, 2-methyl-1-propenyl, 1-butenyl and 2-butenyl.

The term "alkynyl" is used herein to mean a straight or branched chain radical of 2-10 carbon atoms, unless the chain length is limited thereto, wherein there is at least one triple bond between two of the carbon atoms in the chain. Typical alkynyl groups include ethynyl, 1-propynyl, 1-methyl-2-propynyl, 2-propynyl, 1-butynyl and 2-butynyl.

Alkoxy groups contain oxygen substituted by one of the $C_{1-10}$ alkyl groups mentioned above, which may be optionally substituted.

Alkylthio groups contain sulfur substituted by one of the $C_{1-10}$ alkyl groups mentioned above, which may be optionally substituted. Also included are the sulfoxides and sulfones of such alkylthio groups.

Amino groups include $-NH2$, $-NHR_{15}$ and $-NR_{15}R_{16}$, wherein $R_{15}$ and $R_{16}$ are C1-10 alkyl or cycloalkyl groups, or $R_{15}$ and $R_{16}$ are combined with the N to form a ring structure, such as a piperidine, or $R_{15}$ and $R_{16}$ are combined with the N and other group to form a ring, such as a piperazine. The alkyl group may be optionally substituted.

The term "aryl" as employed herein by itself or as part of another group refers to monocyclic, bicyclic or tricyclic aromatic groups containing from 6 to 14 carbons in the ring.

Common aryl groups include C6-14 aryl, preferably C6-10 aryl. Typical C6-14 aryl groups include phenyl, naphthyl, phenanthrenyl, anthracenyl, indenyl, azulenyl, biphenyl, biphenylenyl and fluorenyl groups.

Cycloalkyl groups are C3-8 cycloalkyl. Typical cycloalkyl groups include cyclopropyl, cyclobutyl, cyclopentyl, cyclohexyl and cycloheptyl.

The term "arylalkyl" is used herein to mean any of the above-mentioned C1-10 alkyl groups substituted by any of the above-mentioned C6-14 aryl groups. Preferably the arylalkyl group is benzyl, phenethyl or naphthylmethyl.

The term "arylalkenyl" is used herein to mean any of the above-mentioned C2-10 alkenyl groups substituted by any of the above-mentioned C6-14 aryl groups.

The term "arylalkynyl" is used herein to mean any of the above-mentioned C2-10 alkynyl groups substituted by any of the above-mentioned C6-14 aryl groups.

The term "aryloxy" is used herein to mean oxygen substituted by one of the above-mentioned C6-14 aryl groups, which may be optionally substituted. Common aryloxy groups include phenoxy and 4-methylphenoxy.

The term "arylalkoxy" is used herein to mean any of the above mentioned C1-10 alkoxy groups substituted by any of the above-mentioned aryl groups, which may be optionally substituted. Example arylalkoxy groups include benzyloxy and phenethyloxy.

Example haloalkyl groups include C1-10 alkyl groups substituted by one or more fluorine, chlorine, bromine or iodine atoms, e.g., fluoromethyl, difluoromethyl, trifluoromethyl, pentafluoroethyl, 1,1-difluoroethyl, chloromethyl, chlorofluoromethyl and trichloromethyl groups.

Acylamino (acylamido) groups include any C1-6 acyl (alkanoyl) attached to an amino nitrogen, e.g., acetamido, chloroacetamido, propionamido, butanoylamido, pentanoylamido and hexanoylamido, as well as aryl-substituted C1-6 acylamino groups, e.g., benzoylamido, and pentafluorobenzoylamido.

Common acyloxy groups are any C1-6 acyl (alkanoyl) attached to an oxy (—O—) group, e.g., formyloxy, acetoxy, propionoyloxy, butanoyloxy, pentanoyloxy and hexanoyloxy.

The term heterocycle is used herein to mean a saturated or partially saturated 3-7 membered monocyclic, or 7-10 membered bicyclic ring system, which consists of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on carbon or on a nitrogen atom if the resulting compound is stable.

Common saturated or partially saturated heterocyclic groups include tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl pyrazolinyl, tetronoyl and tetramoyl groups.

The term "heteroaryl" as employed herein refers to groups having 5 to 14 ring atoms; 6, 10 or 14 π electrons shared in a cyclic array; and containing carbon atoms and 1, 2 or 3 oxygen, nitrogen or sulfur heteroactoms.

Example heteroaryl groups include thienyl (thiophenyl), benzo[b]thienyl, naphtho[2,3-b]thienyl, thianthrenyl, furyl (furanyl), pyranyl, isobenzofuranyl, chromenyl, xanthenyl, phenoxanthiinyl, pyrrolyl, including without limitation 2H-pyrrolyl, imidazolyl, pyrazolyl, pyridyl (pyridinyl), including without limitation 2-pyridyl, 3-pyridyl, and 4-pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-α]pyrimidin-4-one, pyrazolo[1,5-α]pyrimidinyl, including without limitation pyrazolo[1,5-α]pyrimidin-3-yl, 1,2-benzoisoxazol-3-yl, benzimidazolyl, 2-oxindolyl and 2-oxobenzimidazolyl. Where the heteroaryl group contains a nitrogen atom in a ring, such nitrogen atom may be in the form of an N-oxide, e.g., a pyridyl N-oxide, pyrazinyl N-oxide and pyrimidinyl N-oxide.

The term "heteroaryloxy" is used herein to mean oxygen substituted by one of the above-mentioned heteroaryl groups, which may be optionally substituted. Useful heteroaryloxy groups include pyridyloxy, pyrazinyloxy, pyrrolyloxy, pyrazolyloxy, imidazolyloxy and thiophenyloxy.

The term "heteroarylalkoxy" is used herein to mean any of the above-mentioned C1-10 alkoxy groups substituted by any of the above-mentioned heteroaryl groups, which may be optionally substituted.

A permeation enhancer is generally an agent that facilitates the active compounds of the invention.

A co-solvent (i.e., a latent solvent or indirect solvent) is an agent that becomes an effective solvent in the presence of an active solvent and can improve the properties of the primary (active) solvent.

The composition can be produced in concentrated form that includes little or no water. The composition can be diluted with water or some other solvent prior to use to treat plants, seeds, soil or vertebrates.

The details of one or more embodiments of the invention are set forth in the accompanying drawings and the description below. Other features, objects, and advantages of the invention will be apparent from the description and drawings, and from the claims.

DESCRIPTION OF THE PREFERRED EMBODIMENTS

Figure 1:
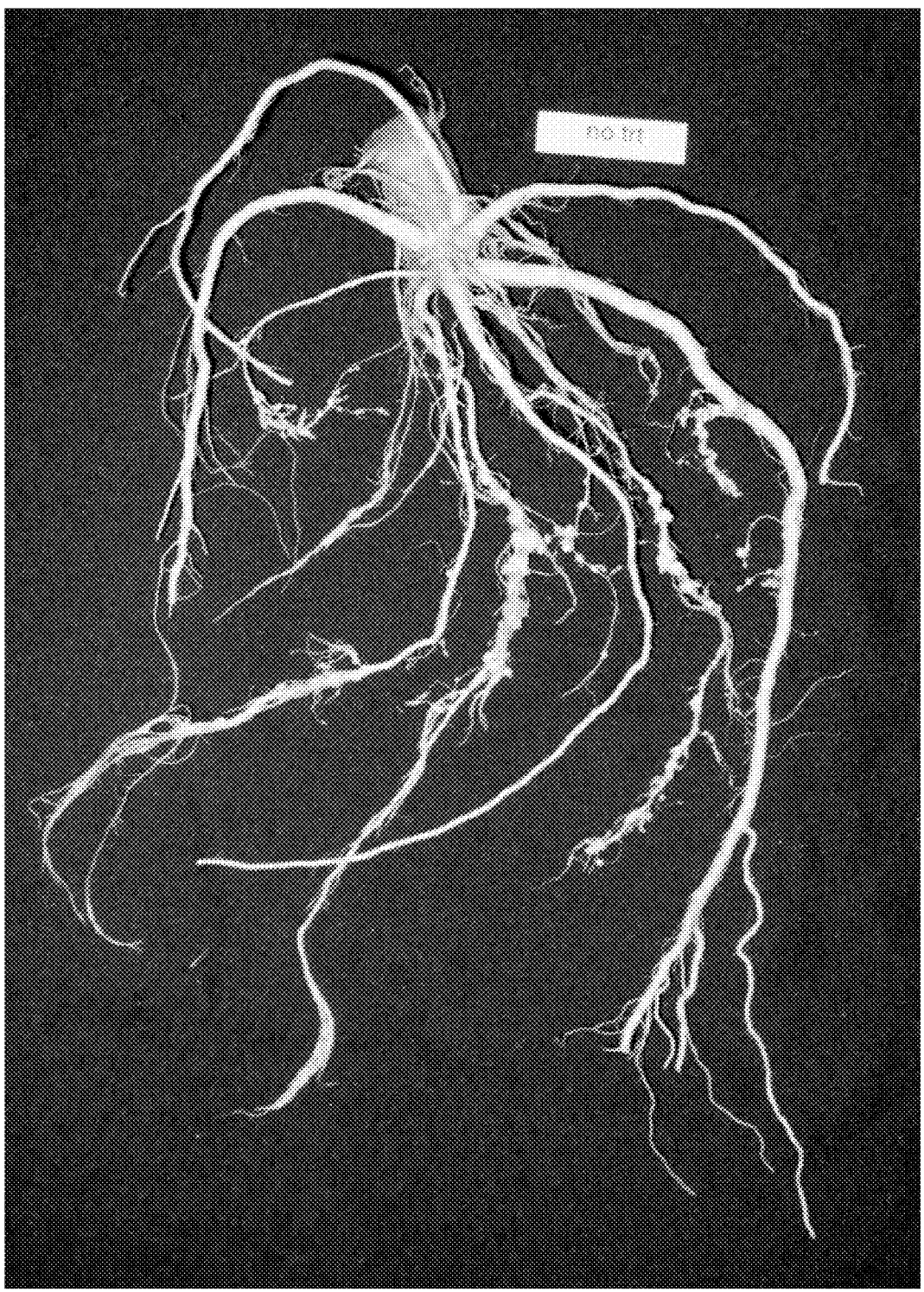
FIG. 1: Root galling seen in plants with no chemical applications (Fall trial).
Figure 2:
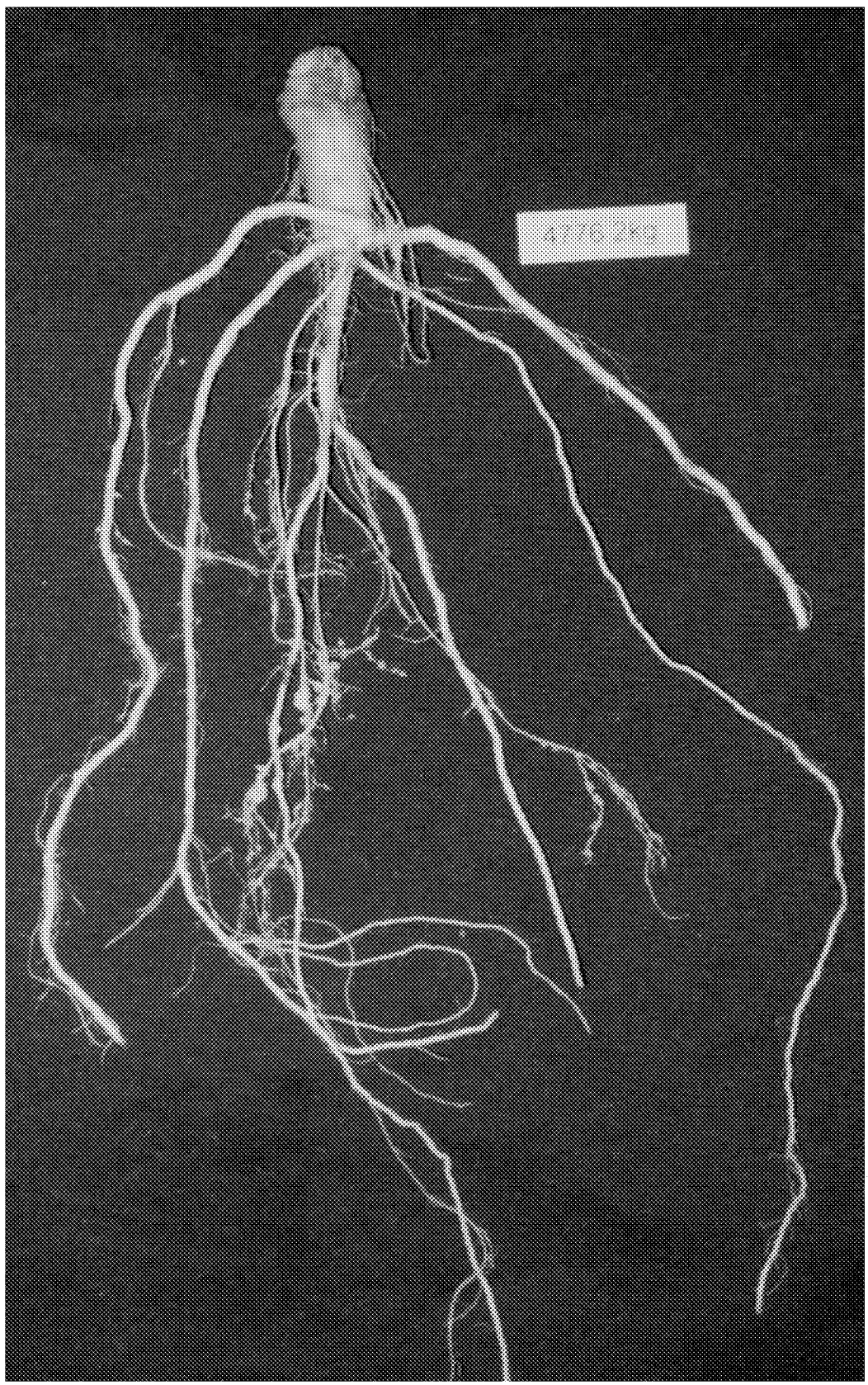
FIG. 2: Typical root galling seen in plants treated with 2 kg/ha 4776 (Fall trial).
Figure 3:
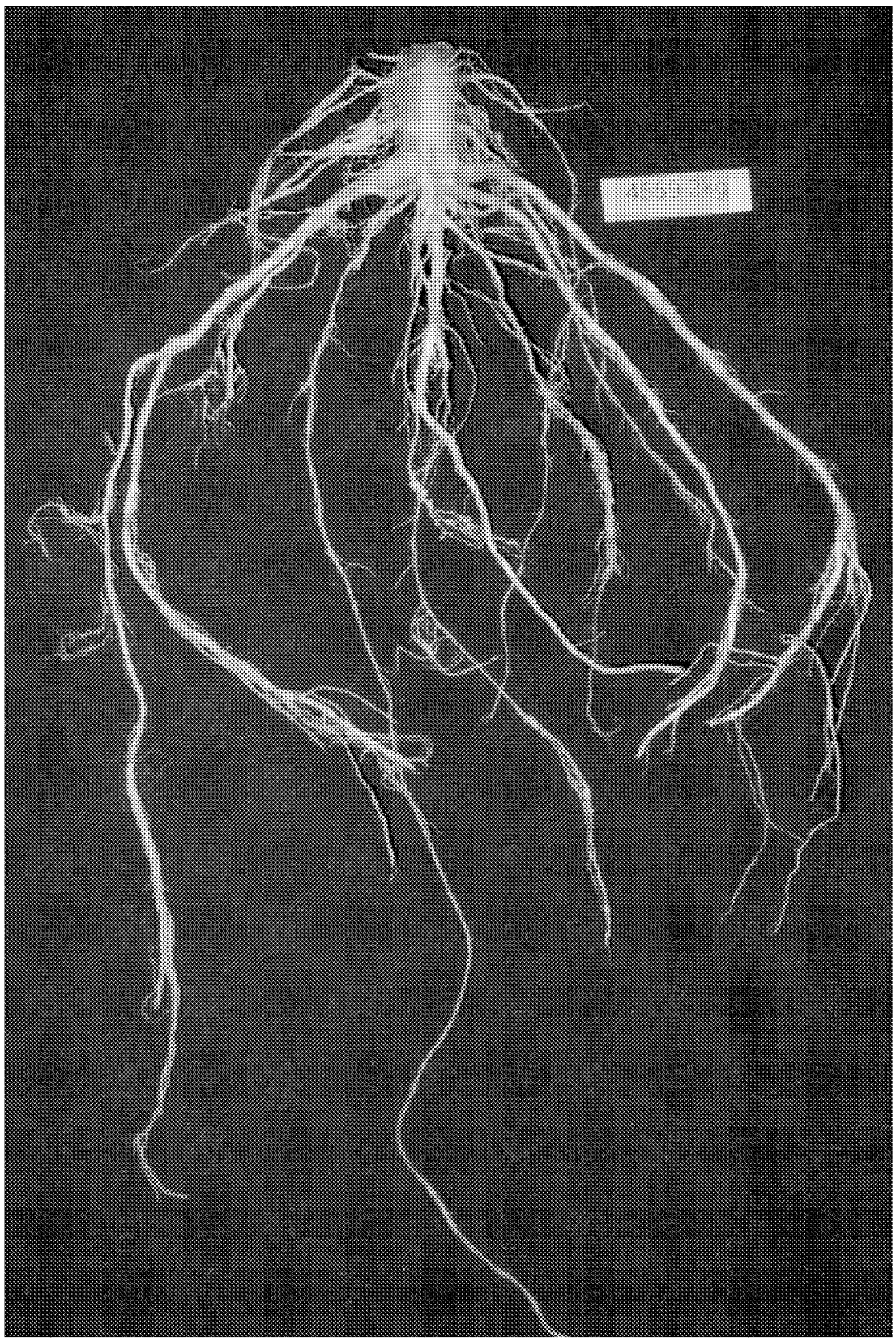
FIG. 3: Typical root galling in plants treated with 2 kg/ha 4559 (Fall trial).
Figure 4:
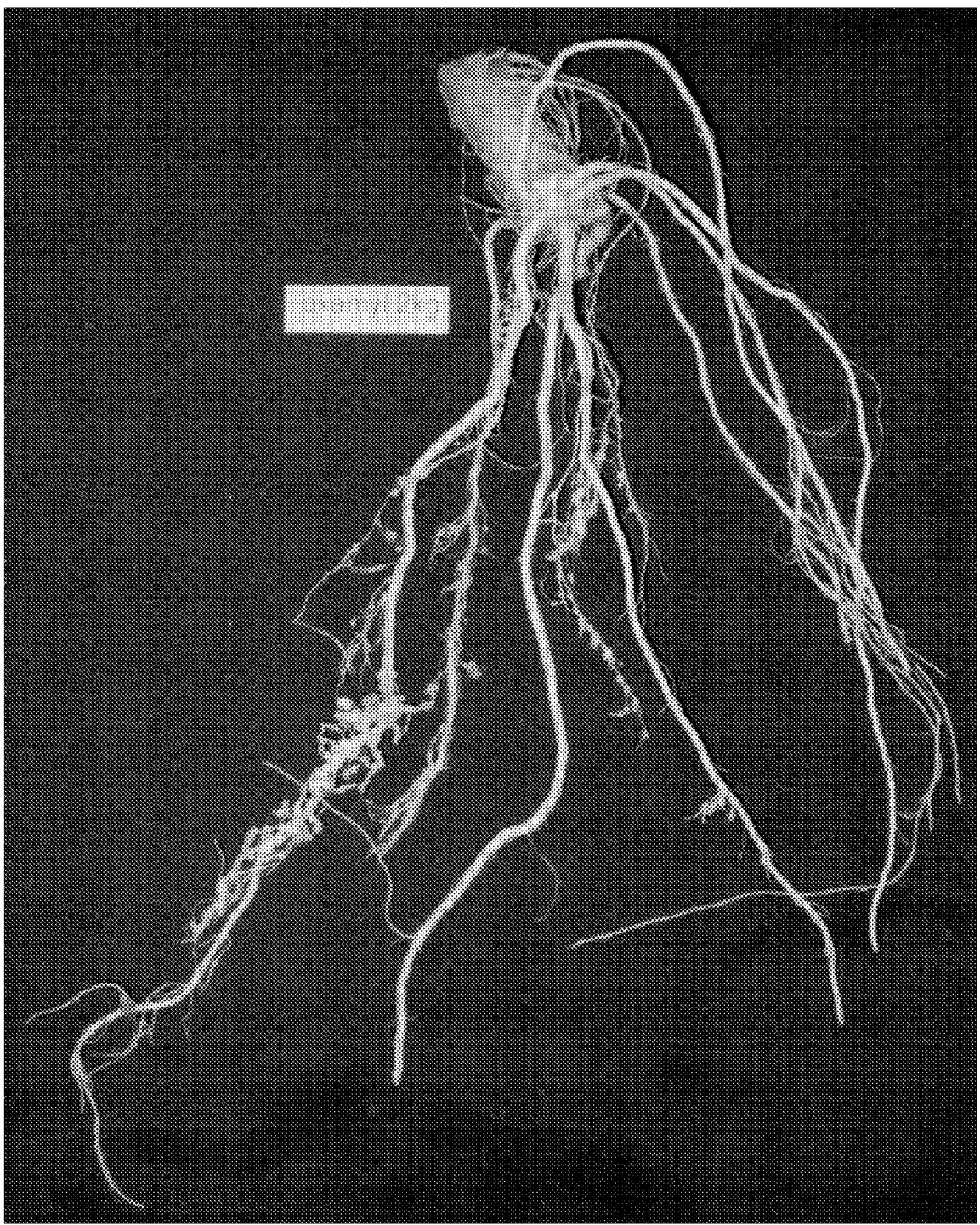
FIG. 4: Typical root galling in plants treated with 2 kg/ha of the commercial nematicide oxamyl (Fall trial).
Figure 5:
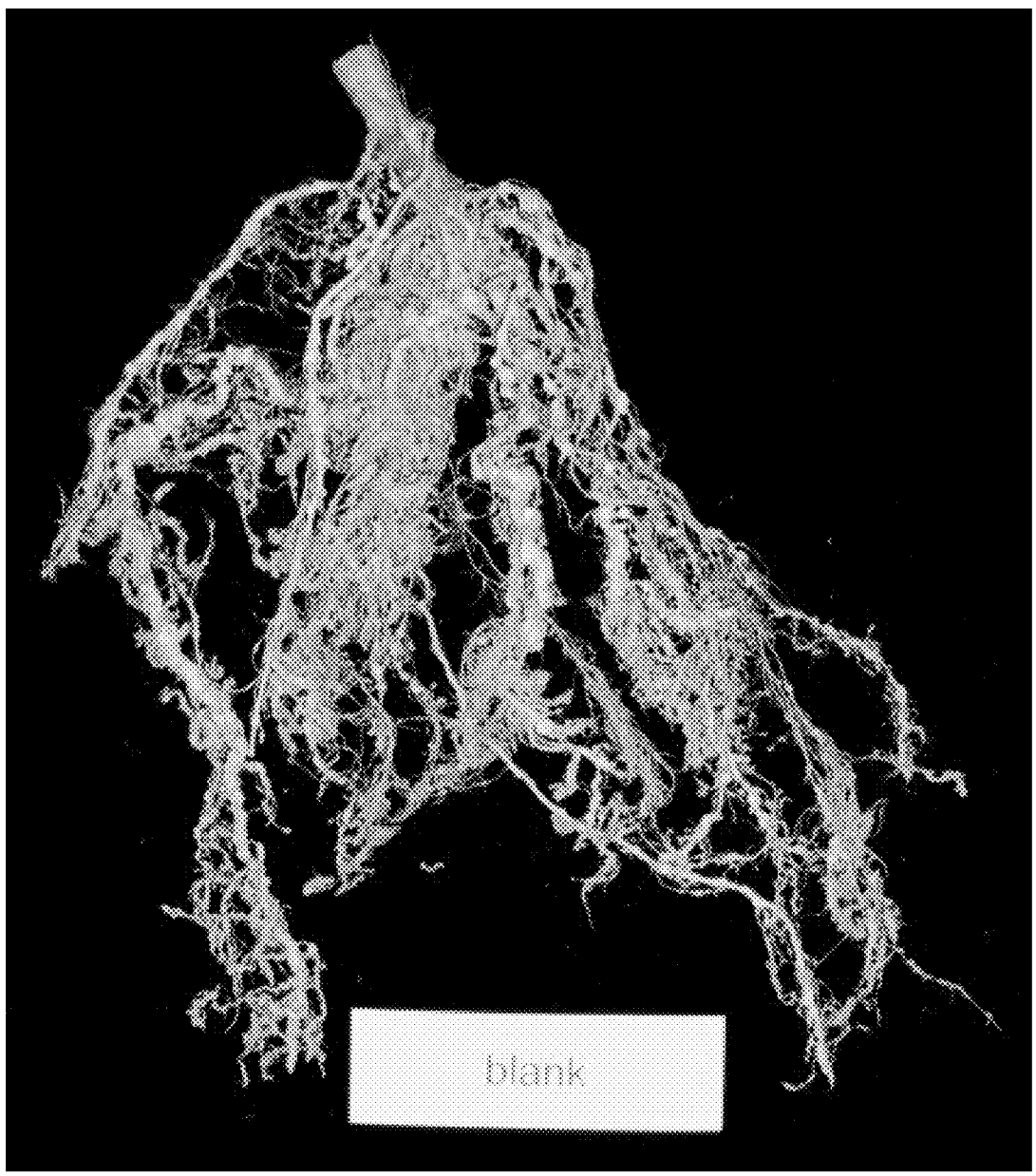
FIG. 5: Root galling seen in plants with no chemical applications (Summer trial).
Figure 6:
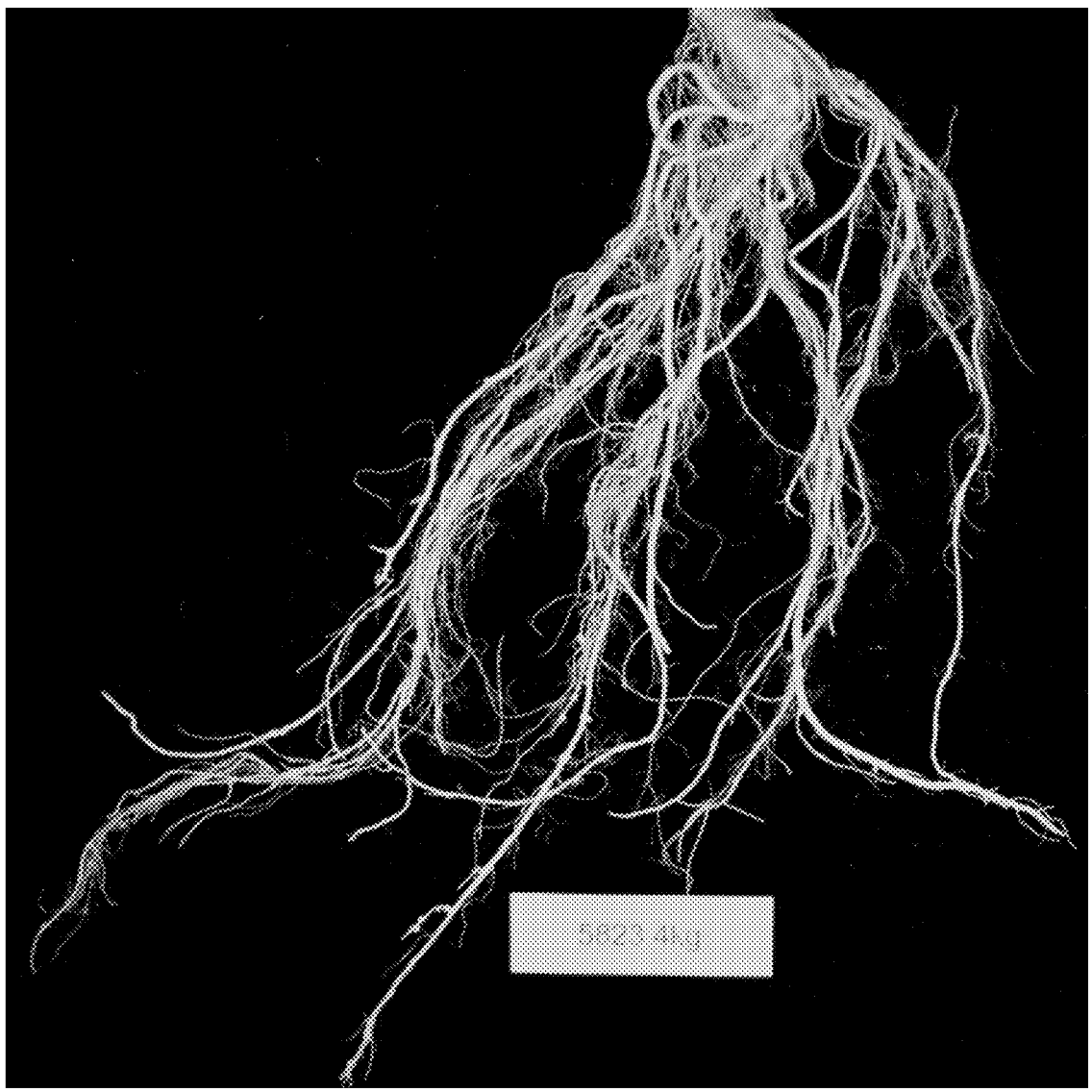
FIG. 6: Typical root galling seen in plants treated with 4 kg/ha 5823 (Summer trial).
Figure 7:
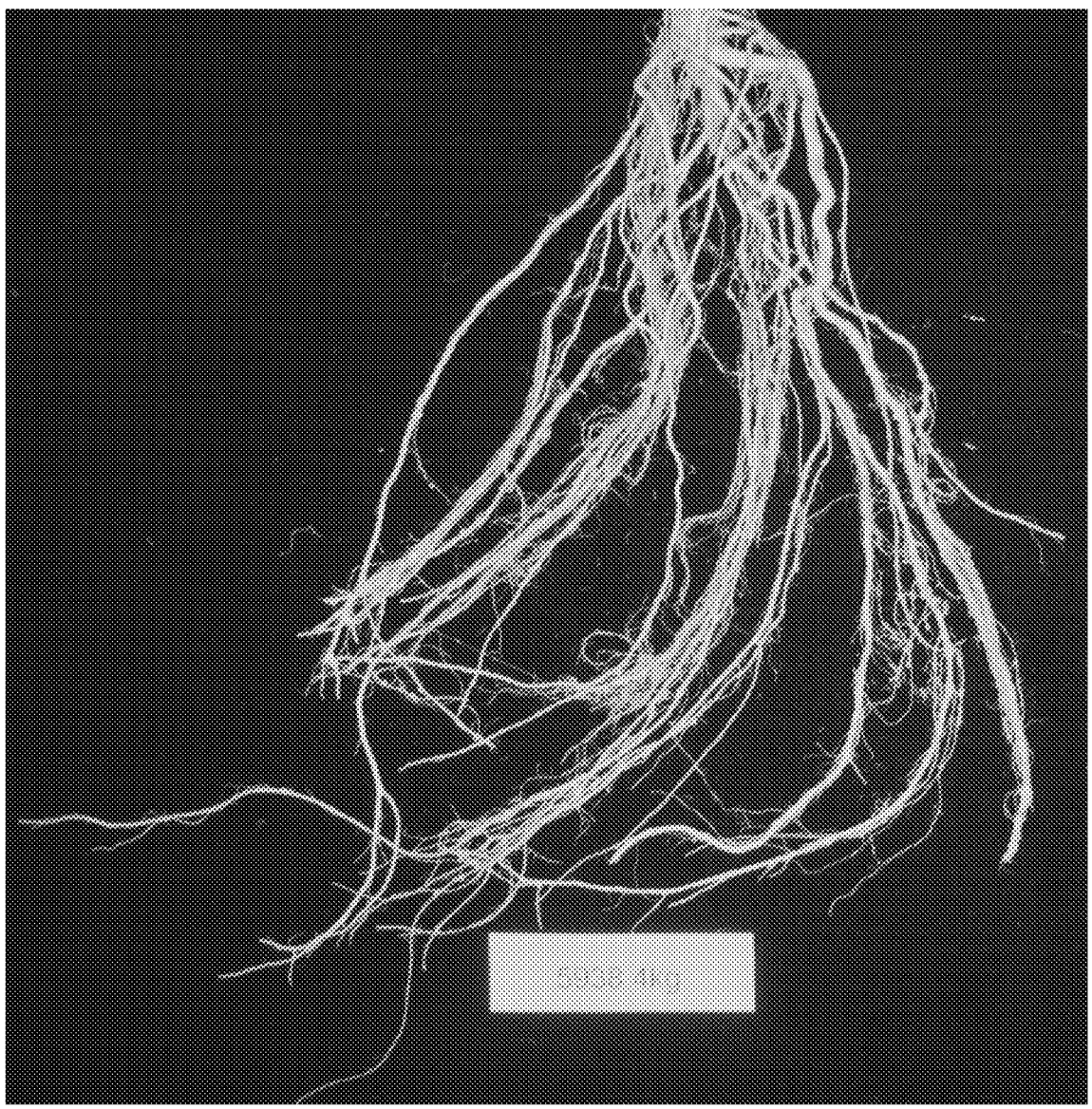
FIG. 7: Typical root galling in plants treated with 4 kg/ha 5938 (Summer trial).

Described herein are certain compounds, some of which are oxazole, oxadiazole and thiadiazole analogs with potent broad spectrum nematicidal activity.

The nematicidal compounds may be supplied to plants exogenously, through sprays for example. These compounds may also be applied as a seed coat. The compounds can be applied to plants or the environment of plants needing nematode control, or to animals or the food of animals needing nematode parasite control. The compositions may be applied by, for example drench or drip techniques. With drip applications compounds can be applied directly to the base of the plants or the soil immediately adjacent to the plants. The composition may be applied through existing drip irrigation systems. This procedure is particularly applicable for cotton, strawberries, tomatoes, potatoes, vegetables and ornamental plants. Alternatively, a drench application can be used where a sufficient quantity of nematicidal composition is applied such that it drains to the root area of the plants. The drench technique can be used for a variety of crops and turf grasses. The drench technique can also be used for animals. Preferably, the nematicidal compositions would be administered orally to promote activity against internal parasitic nematodes. Nematicidal compositions may also be administered in some cases by injection of the host animal or by topical applications.

The concentration of the nematicidal composition should be sufficient to control the parasite without causing significant phytotoxicity to the desired plant or undue toxicity to the animal host. The compounds disclosed in this invention have a good therapeutic window.

We have surprisingly found that certain oxazole, oxadiazole and thiadiazole analogs (e.g., 5-(4-chloro-2-fluorophenyl)-2-(thiophen-2-yl)oxazole, 3-(4-chloro-2-methylphenyl)-5-(furan-2-yl)-1,2,4-oxadiazole, 3-(2,4-dichlorophenyl)-5-(furan-2-yl)-1,2,4-thiadiazole) have nematicidal potencies comparable with organophosphate and carbamate standards yet display excellent selectivity for nematodes over plants and animals. Thus, these analogs will provide useful compounds for nematode parasite control.

The nematicidal agents described herein can be applied in conjunction with another pesticidal agents. The second agent may, for example, be applied simultaneously or sequentially. Such pesticidal agents can include for example, avermectins for animal applications.

The aforementioned nematicidal compositions can be used to treat diseases or infestations caused by nematodes of the following non-limiting, exemplary genera: *Anguina, Ditylenchus, Tylenchorhynchus, Pratylenchus, Radopholus, Hirschmanniella, Nacobbus, Hoplolaimus, Scutellonema, Rotylenchus, Helicotylenchus, Rotylenchulus, Belonolaimus, Heterodera*, other cyst nematodes, *Meloidogyne, Criconemoides, Hemicycliophora, Paratylenchus, Tylenchulus, Aphelenchoides, Bursaphelenchus, Rhadinaphelenchus, Longidorus, Xiphinema, Trichodorus*, and *Paratrichodorus, Dirofiliaria, Onchocerca, Brugia, Acanthocheilonema, Aelurostrongylus, Anchlostoma, Angiostrongylus, Ascaris, Bunostomum, Capillaria, Chabertia, Cooperia, Crenosoma, Dictyocaulus, Dioctophyme, Dipetalonema, Dracunculus, Enterobius, Filaroides, Haemonchus, Lagochilascaris, Loa, Manseonella, Muellerius, Necator, Nematodirus, Oesophagostomum, Ostertagia, Parafilaria, Parascaris, Physaloptera, Protostrongylus, Setaria, Spirocerca, Stephanogilaria, Strongyloides, Strongylus, Thelazia, Toxascaris, Toxocara, Trichinella, Trichostrongylus, Trichuris, Uncinaria,* and *Wuchereria*. Particularly preferred are nematodes including *Dirofilaria, Onchocerca, Brugia, Acanthocheilonema, Dipetalonema, Loa, Mansonella, Parafilaria, Setaria, Stephanofilaria,* and *Wucheria, Pratylenchus, Heterodera, Meloidogyne, Paratylenchus*. Species that are particularly preferred are: *Ancylostoma caninum, Haemonchus contortus, Trichinella spiralis, Trichurs muris, Dirofilaria immitis, Dirofilaria tenuis, Dirofilaria repens, Dirofilari ursi, Ascaris suum, Toxocara canis, Toxocara cati, Strongyloides ratti, Parastrongyloides trichosuri, Heterodera glycines, Globodera pallida, Meloidogyne javanica, Meloidogyne incognita,* and *Meloidogyne arenaria, Radopholus similis, Longidorus elongatus, Meloidogyne hapla,* and *Pratylenchus penetrans*.

The following examples are, therefore, to be construed as merely illustrative, and not limitative of the remainder of the disclosure in any way whatsoever. All of the publications cited herein are hereby incorporated by reference in their entirety.

EXAMPLES

Example 1: *M. Incognita* Testing of Several Nematicidal Compounds in a Miniaturized Greenhouse Assay Overview:

The test compound is dissolved in an acetone solution and added to water. A sprouted cucumber seedling is placed into a vial with dry sand and the water-chemical solution is added immediately. Twenty four hours later *Meloidogyne incognita* eggs are added to the vials and 10 to 12 days later the roots are evaluated for nematode galling.

Procedure:

Cucumber seeds are sprouted for 3 days in moist paper towels. Acceptable sprouts should be 3 to 4 cm long with several lateral roots just emerging. Stock solutions of chemistry are prepared in a mixture of acetone and Triton X100 (412 mg in 500 mL) to a final concentration of 5 mg/mL. The chemical stock solution is then added to 10 mL deionized water plus 0.015% Triton X100 and mixed thoroughly. This is enough to test each condition in triplicate. Ten mL dry sand is added to each vial. At this time the solubility of the chemistry is visually determined and recorded as either ppt (large precipitates) or cloudy (fine precipitates). Seedlings are planted by tilting the vial and laying the seedling in the correct orientation so that the cotyledons are just above the sand and then tilting back to cover the radicles with sand. 3.3 ml water/chemical mix is added to each vial and the vials placed in racks under fluorescent light banks. The vials are inoculated two days after planting by adding 500 vermiform *M. incognita* eggs to each vial in 50 uL of deionized or spring water. The vials are then kept under the fluorescent lamps at ambient room temperature and watered as needed with 1 mL deionized water, usually twice during duration of test. Harvest of the cucumber plants is done 10 to 12 days after inoculation by washing sand off the roots. A root gall rating and visual phytotoxicity rating is assigned using the following scales: Gall rating scale (Gall: % root mass galled): 0=0-5%; 1=6-20%; 2=21-50%; and 3=51-100%. The average of the triplicate gall rating is then calculated: green=0.00-0.33 (no galls); yellow=0.67-1.33 (mild galling); orange=1.67-2.33 (moderate galling); red=2.67-3.00 (severe galling). Visual phytotoxicity scale is also assigned (Vis. tox; visual reduction in root mass compared to the control): rs1=mild stunting; rs2=moderate stunting; rs3=severe stunting.

TABLE 1A

Potent nematicidal oxadiazole and oxazole 2-thiophene and 2-furan analogs showing examples of substitutions compatible with high activity

| Name | Analog | 8 ppm gall ratings |
|---|---|---|
| 1822 | | 0 |
| 1846 | | 0 |
| 4417 | | 0.33 |
| 4559 | | 0 |
| 4775 | | 0 |
| 4776 | | 0 |

TABLE 1A-continued

Potent nematicidal oxadiazole and oxazole 2-thiophene and 2-furan analogs showing examples of substitutions compatible with high activity

| Name | Analog | 8 ppm gall ratings |
|---|---|---|
| 4948 | 5-(4-bromophenyl)-2-(thiophen-2-yl)-1,3,4-oxadiazole | 0 |
| 4971 | 5-(4-trifluoromethylphenyl)-2-(thiophen-2-yl)-1,3,4-oxadiazole | 0.67 |
| 5006 | 5-(4-methylphenyl)-2-(thiophen-2-yl)-1,3,4-oxadiazole | 0 |
| 5012 | 5-(3-chlorophenyl)-2-(thiophen-2-yl)-1,3,4-oxadiazole | 0.67 |
| 5082 | 5-(4-chlorophenyl)-2-(furan-2-yl)-1,3,4-oxadiazole | 1.67 |
| 5090 | 5-(2-methylphenyl)-2-(thiophen-2-yl)-1,3,4-oxadiazole | 1.67 |
| 5132 | 5-(4-trifluoromethylphenyl)-2-(furan-2-yl)-1,3,4-oxadiazole | 1.33 |
| 5181 | 3-(3-trifluoromethylphenyl)-5-(furan-2-yl)-1,2,4-oxadiazole | 0.33 |
| 5212 | 3-(3-trifluoromethylphenyl)-5-(thiophen-2-yl)-1,2,4-oxadiazole | 1 |
| 5213 | 3-(4-trifluoromethylphenyl)-5-(thiophen-2-yl)-1,2,4-oxadiazole | 0.33 |
| 5292 | 3-(pyridin-3-yl)-5-(furan-2-yl)-1,2,4-oxadiazole | 0.67 |
| 5297 | 3-(pyridin-3-yl)-5-(thiophen-2-yl)-1,2,4-oxadiazole | 0.33 |
| 5456 | 5-(naphthalen-1-yl)-2-(thiophen-2-yl)-1,3,4-oxadiazole | 0.67 |
| 5467 | 3-(4-bromophenyl)-5-(furan-2-yl)-1,2,4-oxadiazole | 0 |
| 5468 | 3-(4-iodophenyl)-5-(thiophen-2-yl)-1,2,4-oxadiazole | 1 |
| 5475 | 5-(4-bromophenyl)-3-(thiophen-2-yl)-1,2,4-oxadiazole | 1.33 |
| 5478 | 3-(4-fluorophenyl)-5-(furan-2-yl)-1,2,4-oxadiazole | 0 |
| 5479 | 3-(4-fluorophenyl)-5-(thiophen-2-yl)-1,2,4-oxadiazole | 0 |
| 5499 | 5-(2,4-dichlorophenyl)-2-(furan-2-yl)-1,3,4-oxadiazole | 0 |
| 5523 | 3-(4-chlorophenyl)-5-(furan-2-yl)-1,2,4-oxadiazole | 0 |

TABLE 1A-continued

Potent nematicidal oxadiazole and oxazole 2-thiophene and 2-furan analogs showing examples of substitutions compatible with high activity

| Name | Analog | 8 ppm gall ratings |
|---|---|---|
| 5527 | 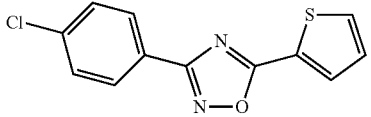 [SMILES: Clc1ccc(-c2noc(-c3cccs3)n2)cc1] | 0.67 |
| 5556 | 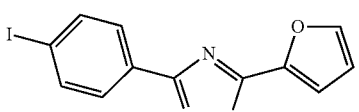 | 0.33 |
| 5586 | 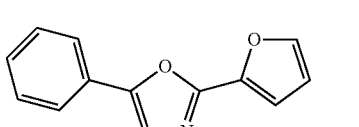 | 0.67 |
| 5587 | 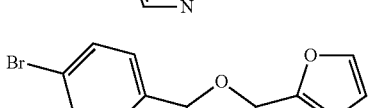 | 0 |
| 5618 | 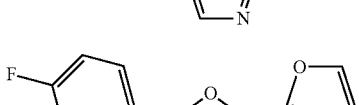 | 1.33 |
| 5622 | 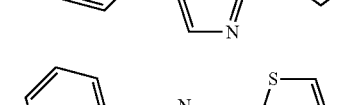 | 0 |
| 5623 | 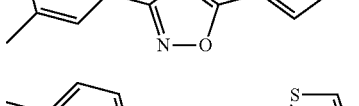 | 0 |
| 5625 | 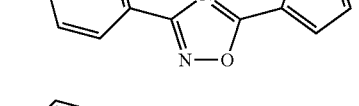 | 0.33 |
| 5663 | 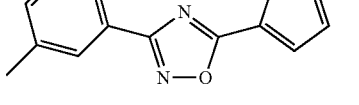 | 0 |
| 5666 | 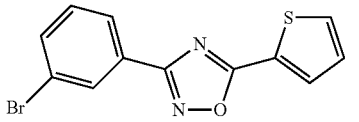 [SMILES: Brc1cccc(-c2noc(-c3cccs3)n2)c1] | 1.33 |
| 5671 | 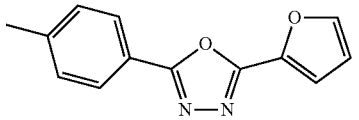 | 0.67 |

TABLE 1A-continued

Potent nematicidal oxadiazole and oxazole 2-thiophene and 2-furan analogs showing examples of substitutions compatible with high activity

| Name | Analog | 8 ppm gall ratings |
|---|---|---|
| 5672 | 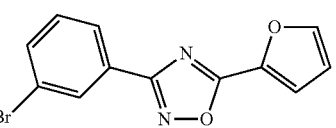 | 0 |
| Oxamyl | | 0.67 (1 ppm) |

A variety of single substitutions on or in the six membered aromatic ring (e.g., pyridine or pyrazine in place of phenyl) of the phenyl-2-furan and phenyl-2-thiophene oxadiazoles and oxazoles are compatible with high nematicidal activity. Examples of preferred single substitutions include halogens, $CH_3$, $CF_3$, $OCF_3$ and $OCH_3$ especially in the para position (4-position) of the phenyl ring. The phenyl ring can also be multiply substituted in a way compatible with high nematicidal efficacy. Ring numbering system is shown below.

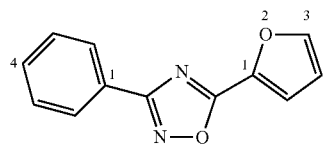

TABLE 1B

Examples of nematicidal thiadiazole, oxadiazole and oxazole analogs with potency comparable to commercial standards

| Name | Analog | 1 ppm gall ratings* |
|---|---|---|
| 4776 | 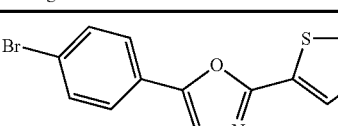 | $1^a$, $1^b$, $0.33^c$, $0.33^d$ |
| 1822 | 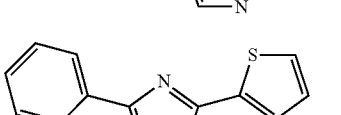 | $0.33^a$, $0.67^b$, $0.33^c$, $0^d$ |
| 4559 | 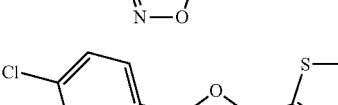 | $1^a$ |
| 5499 | 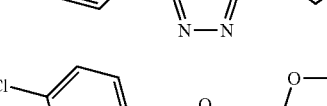 | $1^a$ |

TABLE 1B-continued

Examples of nematicidal thiadiazole, oxadiazole and oxazole analogs with potency comparable to commercial standards

| Name | Analog | 1 ppm gall ratings* |
|---|---|---|
| 1846 | [structure] | $1.33^a$, $0.67^b$ |
| 5467 | [structure] | $1.67^a$, $1.33^b$ |
| 5479 | [structure] | $1^a$, $0.67^b$ |
| 5523 | [structure] | $1^a$, $1.33^b$ |
| 5527 | [structure] | $1.67^a$, $1^b$ |
| 5823 | [structure] | $1.67^a$, $0.33^b$, $0.33^e$ |
| 5825 | [structure] | $0^a$, $0.33^b$ |
| 5383 | [structure] | $1.33^a$ |
| 5864 | [structure] | $1^a$ |
| 5882 | [structure] | $0.67^a$ |
| 5969 | [structure] | $1^e$ |
| 5915 | [structure] | $0.33^e$ |
| 5970 | [structure] | $1^e$ |
| 5938 | [structure] | $0.67^e$ |
| 5960 | [structure] | $0.33^e$ |
| Oxamyl | | $0.67^a$, $1^b$, $1.33^c$, $1.33^d$, $1^e$ |
| Fenamiphos | | $0^c$, $0^d$, $0^e$ |

*Data with the same letters are taken from the same test.

Several phenyl-2-furan and phenyl 2-thiophene oxadiazoles, oxazoles and thiadiazoles have nematicidal potency equivalent to the commercial carbamate nematicide oxamyl and the commercial organophosphate nematicide fenamiphos. Oxamyl and fenamiphos are highly toxic compounds classified as toxicity Class I chemicals by the US Environmental Protection Agency. Also noteworthy is the fact that some multiply substituted analogs are especially nematicidal.

TABLE 1C

Nematicidal activity 3-furan and 3-thiophene analogs

| Name | Analog | 1 ppm gall rating* |
|---|---|---|
| 5885 | [structure] | $1^a$ |

TABLE 1C-continued

Nematicidal activity 3-furan and 3-thiophene analogs

| Name | Analog | 1 ppm gall rating* |
|---|---|---|
| 5867 | [structure] | 1[a] |
| 5869 | [structure] | 1[a] |
| 5886 | [structure] | 1.33[b] |
| 5887 | [structure] | 1[b] |
| 1822 | [structure] | 0[a], 0.33[b] |
| 4776 | [structure] | 1[a], 0.33[b], 1[c] |
| 5882 | [structure] | 0.67[c] |
| 5876 | [structure] | 1.67[c] |
| Oxamyl | | 1.33[a], 1[b], 0.67[c] |

*Data with the same letters are taken from the same test.

Strong nematicidal activity is not limited to 2-furan and 2-thiophene analogs and is also seen with 3-furan and 3-thiophene. Additionally certain substitutions on the 5-membered thiophene or furan rings appear to be well tolerated.

TABLE 1D

Comparison of nematicidal oxazoles and oxadiazoles with nematicidal pyrazoles and thiazoles

| Name | Analog | 8 ppm gall rating* | 1 ppm gall rating* |
|---|---|---|---|
| 5725 | [structure] | 1.33[a] | 3[a] |
| 5735 | [structure] | 0[a] | 2[a] |
| 5738 | [structure] | 0[a] | 1.33[a] |
| 5741 | [structure] | 0[a] | 1[a] |
| 4776 | [structure] | 0[a] | 0[a] |
| 1822 | [structure] | 0[a] | 1.33[a] |
| 5663 | [structure] | 0[b] | 1.67[b] |
| 1787 | [structure] | 1.67[b] | 3[b] |
| 5645 | [structure] | 0[b] | 2[b] |
| Oxamyl | | | 1.33[a], 1[b] |

*Data with the same letters are taken from the same test.

Oxazoles and oxadiazole analogs of the current invention show significant enhancement in nematicidal potency over comparable nematicidal pyrazoles or nematicidal thiazoles.

Example 2: General Greenhouse Testing Protocols

Soybean Planting and Growth:

Soybeans seeds are planted in 100% sand in two inch square plastic pots.

Chemical treatment is done when the soybeans show the first trifoliate beginning to emerge about 10 to 12 days after planting. At least four hours after chemical application the nematode soybean cyst nematode (SCN) eggs are applied and 28 days after the egg inoculation the test is harvested.

Cucumber Planting and Growth

Cucumber seeds are planted in a sandy soil mixture in two inch square plastic pots. When the cotyledons are fully opened and just as the first leaf begins to emerge, usually 7 days after planting, chemistry for the 7 day treatment is applied. One week later the chemistry for the 0 day treatment is applied. Separate plants are used for each application. The plants are generally in the 1-2 leaf stage now. At least four hours after the chemistry application the pots are inoculated with root knot nematode (RKN) eggs. Plants are rated for galling 14 days after the egg inoculation.

Chemical Formulation and Application

One milligram of chemistry per four pots is equal to one kilogram per hectare of chemical. A standard test uses four replications. For rates above 2 kg/ha, the desired amount of chemical is weighed into a 30 ml vial (example: 8 kg/ha rate=8 mg chemical in 30 ml vial). The chemical is dissolved in 2 ml of appropriate solvent, generally acetone. For rates below 2 kg/ha, 2 milligrams of chemistry is weighed into the vial and dissolved in 2 ml of the solvent. The appropriate amount of chemical concentrate is then pipetted into a separate 30 ml vial and solvent is added to bring the volume to 2 ml (example 0.5 kg/ha=0.5 ml of concentrate+1.5 ml solvent). Each dissolved concentrate is then brought to a total of 20 milliliters using 0.05% Triton X 100 surfactant solution.

Chemical and Nematode Application

Pots to be treated are moist but not saturated. To each of four pots, five milliliters of the appropriate chemical solution is pipetted to the media surface making sure to avoid contact with the base of the plant. Immediately following chemical application, using a mist nozzle, the pot surface is wetted sufficiently to saturate the pot watering in the chemistry. The chemical application is done in the morning.

Nematode eggs, either SCN or RKN, are added to distilled water to create a concentration of 1000 vermiform eggs per liter of water. At least four hours after chemical treatment the eggs are applied to the treated pots plus non-treated check plants. A small hole about 1 cm deep is punched into the pot surface. One milliliter of the nematode egg slurry is pipetted into the hole. Immediately afterwards the hole is gently covered. Watering of the test plants is then restricted to only water as needed to prevent wilt for a period of 24 hours. After the 24 hour restricted watering, normal sub-irrigation watering is done for the duration of the test.

TABLE 2A

| | SCN greenhouse sand assay on soybean plants | | | | | |
|---|---|---|---|---|---|---|
| Name | Analog | 2 kg* | 1 kg* | 0.5 kg* | 0.25 kg* | 0.1 kg* |
| 1822 | 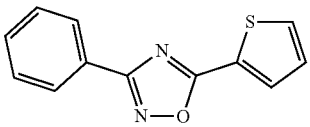 [SMILES: c1ccc(-c2noc(-c3cccs3)n2)cc1] | 100[a] | | | | |
| 4559 | 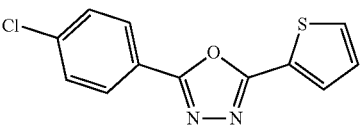 [SMILES: Clc1ccc(-c2nnc(-c3cccs3)o2)cc1] | 98[a] | | | | |
| 4776 | 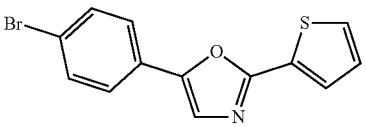 | 99[a] | | | 89[c] | 78[c] |
| 5181 | 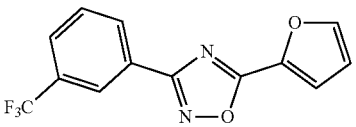 | 100[a] | | | | |
| 5292 | 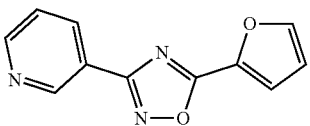 [SMILES: c1cncc(-c2noc(-c3ccco3)n2)c1] | 92[a] | | | | |
| 4417 | 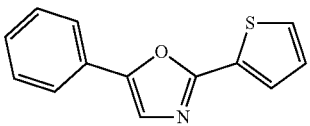 [SMILES: c1ccc(-c2cnc(-c3cccs3)o2)cc1] | | 94[b] | | | |

TABLE 2A-continued

SCN greenhouse sand assay on soybean plants

| Name | Analog | 2 kg* | 1 kg* | 0.5 kg* | 0.25 kg* | 0.1 kg* |
|---|---|---|---|---|---|---|
| 4775 | 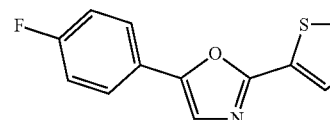 | 95[b] | | | | |
| 5823 | 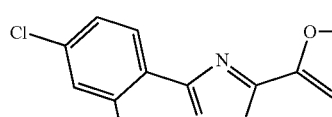 | | | | 69[d] | 38[d] |
| 5915 | 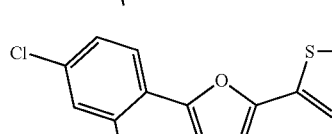 | | | | 74[d] | 44[d] |
| 5938 | 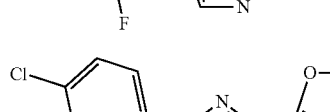 | | | | 89[d] | 60[d] |
| 5939 | 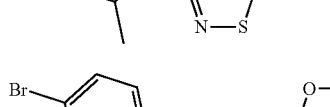 | | | | 88[d] | 64[d] |
| Fenamiphos | | 98[a] 98[b] 94[c] | | | 26[d] | 5[d] |

*Rate in kg/ha. Data shows percent control (i.e., cyst number reduction) relative to the control blank treatment. Data with the same letters are taken from the same test.

The oxazoles, oxadiazoles and thiadiazoles of this invention are highly efficacious nematicides against soybean cyst nematode with potencies comparable to fenamiphos demonstrating that this area of chemistry has broad nematicidal spectrum.

TABLE 2B

RKN greenhouse soil assay on cucumber plants

| | | 0 day kg/ha rate* | | | | 7 day kg/ha rate* | | | |
|---|---|---|---|---|---|---|---|---|---|
| Name | Analog | 1 | 0.25 | 0.1 | 0.05 | 1 | 0.25 | 0.1 | 0.05 |
| 5823 | 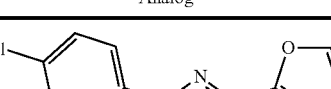 | | 95[a] 98[c] | 85[a] 91[c] | 53[a] 38[c] | | | | |
| 5825 | 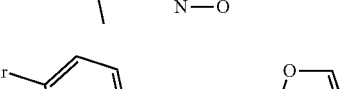 | 94[b] | 89[a] 84[b] | 50[a] | 53[a] | 97[b] | | | |

TABLE 2B-continued

RKN greenhouse soil assay on cucumber plants

| | | 0 day kg/ha rate* | | | | 7 day kg/ha rate* | | | |
|---|---|---|---|---|---|---|---|---|---|
| Name | Analog | 1 | 0.25 | 0.1 | 0.05 | 1 | 0.25 | 0.1 | 0.05 |
| 5860 | 4-Cl, 2-F-phenyl-1,2,4-oxadiazole-thiophene | 85[a] | 47[a] | | | 86[a] | | | |
| 1822 | phenyl-1,2,4-oxadiazole-thiophene | 89[a]<br>81[b] | 60[a]<br>64[b] | 47[a] | 7[a] | 85[a]<br>75[b] | | | |
| 4776 | 4-Br-phenyl-oxazole-thiophene | — | 99[b] | — | — | | | | |
| 5960 | 2,4-diCl-phenyl-1,3,4-thiadiazole-furan | — | — | — | | | | | |
| | | 76[c] | 75[c] | 75[c] | | | | | |
| 5961 | 4-Br, 2-Cl-phenyl-1,3,4-thiadiazole-furan | — | — | — | | | | | |
| | | 81[c] | 88[c] | 73[c] | | | | | |

*Data shows percent control (i.e., galling reduction) relative to the control blank treatment. Data with the same letters are taken from the same test.

Certain oxazoles, oxadiazoles and thiadiazoles are highly efficacious nematicides in bioactive soil with potencies comparable to fenamiphos and activities that are resistant to biotic or abiotic degradation over a timeframe of least one week.

TABLE 2C

RKN greenhouse soil assay on cucumber plants showing comparison of two different formulations.

| Name | Analogs | Acetone 1 mg/kg* | Radex 1 mg/kg* |
|---|---|---|---|
| 1822 | phenyl-1,2,4-oxadiazole-thiophene | 94 | 98 |
| 5825 | 4-Br, 2-Me-phenyl-1,2,4-oxadiazole-furan | 96 | 96 |
| 1846 | 4-Br-phenyl-1,2,4-oxadiazole-thiophene | 88 | 86 |

TABLE 2C-continued

RKN greenhouse soil assay on cucumber plants showing comparison of two different formulations.

| Name | Analogs | Acetone 1 mg/kg* | Radex 1 mg/kg* |
|---|---|---|---|
| 5523 | 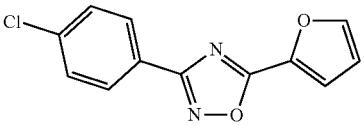 [SMILES: Clc1ccc(-c2noc(-c3cccs3)n2)cc1] | 86 | 86 |
| 5527 | 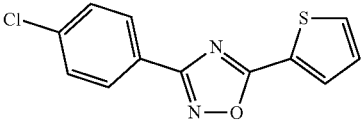 | 91 | 80 |
| 5479 | 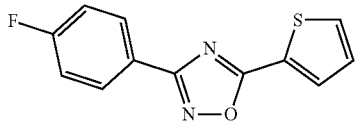 [SMILES: Fc1ccc(-c2noc(-c3cccs3)n2)cc1] | 91 | 96 |
| 5467 | 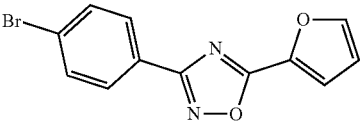 | 73 | 88 |
| Fenam | | 98 | 99 |

*Data shows percent control (i.e., galling reduction) relative to the appropriate control blank treatment. The Acetone formulation is the standard 10% acetone in 0.05% Triton X 100 formulation described above. The Radix formulation was prepared by adding 10 mg of each compound to 150 mg of a mixture of 12% Triton X 100, 11% Agsolex 8, 33% Agsolex 1 and 44% Steposol SC (all by weight). Final was 6.25% active ingredient by weight.

The nematicidal activity of this area of chemistry is not compromised on moving from a typical screening formulation with high amounts of acetone to an emulsifiable concentrate format typical used in commercial applications.

Example 3: *Belonalaimus longicaudatus* (Sting Nematode) Testing Protocols

Populations of sting (*Belonolaimus longicaudatus*) nematodes are maintained on St. Augustine turf grass on soil in 15-cm pots. At test initiation the turf is removed from the pots and the soil containing nematode eggs, juveniles, and adults is subdivided into pots each containing a volume of 125 cm³. The compounds to be tested are dissolved in 3 ml of acetone using 3, 6, or 15 mg to achieve equivalent surface area application rates of 2, 4, or 10 kg/ha, respectively. The 3 ml acetone stock solution is added to 30 ml of water, and 5 ml of that solution is used to drench each of 6 replicate test pots prepared as described above. The treated pots containing nematodes are incubated in the laboratory at ambient temperature of approximately 25° C. After 3 days the soil from each pot is washed onto a modified Baermann apparatus comprised of a screen supporting a layer of filter paper on which the soil sample is placed and set in a dish of water. The samples are then incubated at 25° C. for 24 hours to allow the live nematodes to migrate through the paper and screen and into a water reservoir to be collected for counting with a light microscope. Nematodes that have been killed or immobilized by the test compounds are not able to migrate into the reservoir.

TABLE 3

Efficacy against the sting nematode in a bench top soil assay

| Name | Analog | 2 kg/ha | 4 kg/ha | 10 kg/ha | Other |
|---|---|---|---|---|---|
| 4417 | 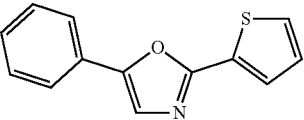 [SMILES: c1ccc(-c2cnc(-c3cccs3)o2)cc1] | 24 | 13 | 7 | |
| 4559 | 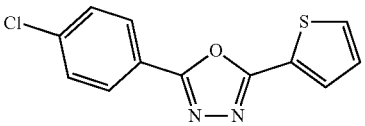 [SMILES: Clc1ccc(-c2nnc(-c3cccs3)o2)cc1] | 39 | 47 | 33 | |

TABLE 3-continued

Efficacy against the sting nematode in a bench top soil assay

| Name | Analog | 2 kg/ha | 4 kg/ha | 10 kg/ha | Other |
|---|---|---|---|---|---|
| 4775 | 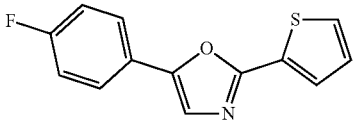 [SMILES: Fc1ccc(-c2cnc(-c3cccs3)o2)cc1] | 15 | 7 | 4 | |
| 4776 | 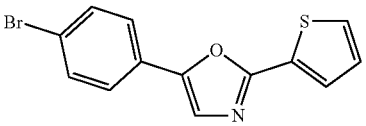 | 16 | 19 | 20 | |
| Positive[#] | | | | | 20 |
| Negative[#] | | | | | 65 |
| Water | | | | | 62 |

*Number of nematodes recovered from treated soil after 3 days incubation with the compound
[#]11.1 kg fenamiphos used as positive control, acetone formulation blank used to dissolve compounds in the negative control.

Certain oxazoles and oxadiazoles are highly efficacious nematicides against the sting nematode which is a serious pest on turf grass. These analogs have potencies comparable to fenamiphos demonstrating that this area of chemistry has broad nematicidal spectrum.

Example 4: *C. Elegans* Testing Protocols

Various compounds were tested for nematicidal activity against *C. elegans* using contact assays in wells. The assays were performed as described below. The test compounds were solubilized in DMSO at 10 mg/ml to create 100× stock solutions. A dilution series was created by diluting the stock solution with DMSO. For each well assay 4 ul of the appropriate dilution is added to a well of a test plate. A 400 ul aliquot of bacterial stock (in M9 buffer with ampicillin and nystatin) are added to each well of the test plate. Worms are added and the test plate placed on a rotary shaker and held at 20° C. Worms are examined and scored at 4 hrs, 24 hrs, 48 hrs and 72 hours.

L1 worms and L4 worms were used in the assay. L1 worms are prepared by plating eggs on a plate without a bacterial feeding layer. The eggs hatch and arrest at the L1 stage. This L1 stage population is then used to create a stock for the experiments. To create an L4 stage stock a small number of worms are taken from an overgrown and starved plate of worms and seeded on a plate with a bacterial feeder layer. A 25 ul aliquot of worms is added to each well in the assay.

TABLE 4

Three day *C. elegans* well assay of nematicidal oxadiazole and oxazole analogs

| Name | Analog | L1 1D* | L1 2D* | L1 3D* | L4 1D* | L4 2D* | L4 3D* |
|---|---|---|---|---|---|---|---|
| 5820 | 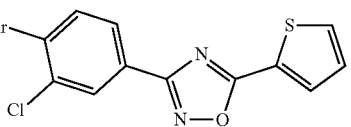 | 0.4 | 0.4 | 0.4 | no | (25 F1) | (6.3 F1) |
| 5821 | 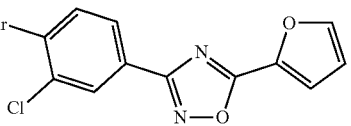 | 0.4 | 0.4 | 0.4 | no | (0.4 F1) | (0.4 F1) |
| 5822 | 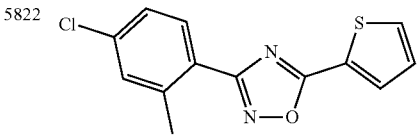 | 1.6 | 0.4 | 0.4 | no | 1.6 | (1.6 F1) |
| 5823 | 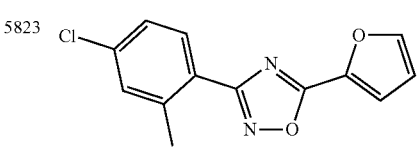 | 0.4 | 0.4 | 0.4 | 1.6 | 0.4 | (0.4 F1) |

TABLE 4-continued

Three day *C. elegans* well assay of nematicidal oxadiazole and oxazole analogs

| Name | Analog | L1 1D* | L1 2D* | L1 3D* | L4 1D* | L4 2D* | L4 3D* |
|---|---|---|---|---|---|---|---|
| 5824 | | 1.6 | 0.4 | 0.4 | no | no | (1.6 F1) |
| 5825 | | 0.4 | 0.4 | 0.4 | 1.6 | 1.6 | (1.6 F1) |
| 5826 | | 6.3 | 1.6 | 1.6 | 6.3 | 6.3 | (6.3 F1) |
| 5827 | | 6.3 | 1.6 | 1.6 | 25 | 6.3 | (6.3 F1) |
| 5828 | | 1.6 | 1.6 | 1.6 | no | no | no |
| 5845 | | no | 1.6 | 0.4 | no | 25 | (25 F1) |
| 5846 | | 1.6 | 0.4 | 0.4 | 1.6 | 1.6 | (1.6 F1) |
| 5847 | | no | 0.4 | 0.4 | no | 1.6 | (1.6 F1) |
| 5848 | | 1.6 | 0.4 | 0.4 | 1.6 | 1.6 | (1.6 F1) |
| 5849 | | 6.3 | 0.4 | 1.6 | no | (6.3 F1) | (6.3 F1) |

TABLE 4-continued

Three day *C. elegans* well assay of nematicidal oxadiazole and oxazole analogs

| Name | Analog | L1 1D* | L1 2D* | L1 3D* | L4 1D* | L4 2D* | L4 3D* |
|---|---|---|---|---|---|---|---|
| 5850 | [structure] | 1.6 | 0.4 | 0.4 | 1.6 | 1.6 | (1.6 F1) |
| 5860 | [structure] | 1.6 | 0.4 | 0.4 | 1.6 | 1.6 | (1.6 F1) |
| 5861 | [structure] | 0.4 | 0.4 | 0.4 | 1.6 | 1.6 | (1.6 F1) |
| 5905 | [structure] | 0.4 | 0.4 | 0.4 | ND | ND | ND |
| 5906 | [structure] | 0.4 | 0.4 | 0.4 | ND | ND | ND |
| 5938 | [structure] | 1.6 | 1.6 | 1.6 | ND | ND | ND |
| 5939 | [structure] | 0.4 | 0.4 | 0.4 | ND | ND | ND |
| 5915 | [structure] | 0.4 | 0.4 | 0.4 | ND | ND | ND |

*EC50 in parts per million of compound after one day, two days or three days of exposure for L1 larvae or L4 larvae. L4 data in parentheses refer to effects on the second generation larvae.
ND: Experiment not done.

The free living nematode *C. elegans* is highly diverged genetically from the tylenchid parasites such as soybean cyst nematode and root knot nematode. Therefore the nematicidal activity of these oxazoles, oxadiazoles and thiadiazoles against *C. elegans* L1 larvae and L4 larvae further confirms that this is chemistry is broadly active against various nematode species and stages.

Example 5: Mouse Acute Toxicity Testing

Acute oral toxicity testing was performed in mice in accordance with test method P203.UDP, as administered by Eurofins/Product Safety Laboratories (Dayton, N.J.). CD-1/Swiss derived albino mice were obtained and group housed in suspended solid bottom caging. The mice were fed rodent chow and filtered tap water was supplied ad libitum. Following acclimation to the laboratory setting, a group of animals was fasted overnight by removing food from the cages. After the fasting period, three female mice were selected based on vitality and initial body weights. The individual compound doses were calculated from these body weights.

The test substance was prepared as a 1% (50 mg/kg) or 5% (500 mg/kg) weight to weight (w/w) mixture in a 0.5% w/w solution of carboxymethylcellulose (CMC) in distilled water. A tissue homogenizer was used to create a homogeneous mixture. A dose of 50 or 500 mg/kg was administered to three healthy mice per dose level by oral intubation using a ball-tipped gavage needle attached to a syringe. After administration, the animals were returned to their cages, and feed was replaced immediately after dosing.

The animals were observed for mortality, signs of gross toxicity and behavioral changes during the first several hours post dosing and at least once daily for up to 14 days. Body weights were recorded prior to initiation and on Days 7 and 14 or a soon as possible after death.

Results were obtained for the following compounds:

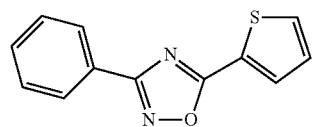

1822

At a dose of 50 mg/kg all animals survived, gained body weight, and appeared active and healthy. There were no signs of gross toxicity, adverse pharmacologic effects, or abnormal behavior. At a dose of 500 mg/kg all animals died within three days of test substance administration.

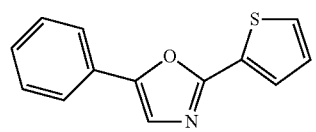

4417

At a dose of 500 mg/kg two animals appeared active and healthy and gained body weight over the 14-day observation period. One animal died within four days of substance administration.

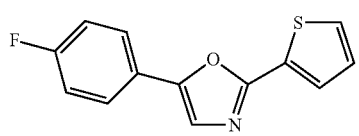

4775

At a dose of 500 mg/kg all animals survived, gained body weight, and appeared active and healthy. There were no signs of gross toxicity, adverse pharmacologic effects, or abnormal behavior.

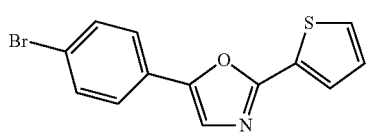

4776

At a dose of 500 mg/kg two animals died within three days of substance administration. One animal appeared active and healthy during the entire study and gained weight over the 14-day observation period

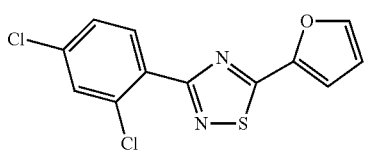

5960

At a dose of 500 mg/kg all animals survived, gained body weight, and appeared active and healthy. There were no signs of gross toxicity, adverse pharmacologic effects, or abnormal behavior.

Based on these mouse studies the oral toxicity of 1822 appears to be between 50 mg/kg and 500 mg/kg, that of 4776 mg/kg to be slightly lower than 500 mg/kg, that of 4417 to be slightly higher than 500 mg/kg and that of 4775 and 5960 to be greater than 500 mg/kg. In comparison, the oral LD50 for aldicarb, oxamyl and fenamiphos in mice are 300 ug/kg, 2.3 mg/kg and 22.7 mg/kg respectively.

Consequently, although the oxazole and oxadiazole chemistry of this invention has broad spectrum nematicidal activity these compounds nonetheless show considerable improvement in safety over the commercial organophosphate and carbamate standards and over abamectin (oral mouse LD50 13.6 mg/kg) the active ingredient the nematicidal seed treatment Avicta™.

Example 6: Advanced Greenhouse Testing Protocols

Pre-Plant Incorporated Test (PPI)

The PPI test examines the effect of pre-incorporation of compounds in soil and longer aging to simulate in furrow methods of nematicide application in the field. The PPI test exposes compounds to a higher volume of soil and drying which can result in more severe soil binding. Compounds are also aged for longer periods which can lead to more extensive biotic and abiotic degradation further limiting activity.

The chemically treated soil (sandy soil mix) for all treatment days (e.g., 7 days, 14 days, 21 days) treatments is potted into their appropriate pots. On the same day the 7 day treatment pots are seeded. One week later eggs are applied and 14 days after egg application the test is harvested. The 14 day treatments are planted 7 days after the first planting. The 14 day planting and 7 day inoculation happen on the same day. One week later the 14 day treatments are inoculated with eggs. These are harvested 14 days after the inoculation. The 21 day treatments are planted 14 days after the first planting. The 14 day inoculation and 21 day planting are done on the same day. One week later the 21 day plants are inoculated with eggs. The 7 day treatment is harvested the same day as the 21 day inoculation. Fourteen days after inoculation the 21 day plants are harvested.

| Treatment | Planting | Inoculation | Harvest |
| --- | --- | --- | --- |
| 7 day | day 0 | day 7 | day 21 |
| 14 day | day 7 | day 14 | day 28 |
| 21 day | day 14 | day 21 | day 35 |

For each compound a stock is prepared using 4 mg material in 4 ml of acetone. The soil is mixed by placing 80 ml of field soil and 320 ml of sand in a plastic bag and mixing well. The formulation for treatment is done by adding 2.13 ml (8 kg/ha rate), 1.06 ml (4 kg/ha rate) or 0.53 ml (2 kg/ha rate) to a vial and raising it with 10 ml in 0.05%×100. Soil is then treated by adding the entire 10 ml to the 400 ml of mix in the bag. The treated soil is immediately mixed well in the sealed bag to distribute the compound evenly. Approximately 95 ml is used to fill each 2-inch square pot up to the top with some soil compression and flattening. For each compound and for the control treatments 4 pots are filled. All pots are watered until moist but with no run-out through the bottom.

The PPI test simulates 8, 4 and 2 kg/ha rates incorporated 15 cm deep in the field and is equivalent to the 2, 1 and 0.5 kg/ha drench application rates in the standard 2-inch pot cucumber greenhouse assay.

TABLE 6A

Seven day pre-plant incorporated greenhouse studies of root knot nematode on cucumber plants

| Name | Analog | 8 ka/ha rate* | 4 kg/ha rate* |
|---|---|---|---|
| 1822 | 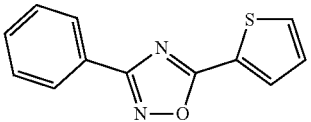 [SMILES: c1ccc(-c2noc(-c3cccs3)n2)cc1] | 99 | 99 |
| 5213 | 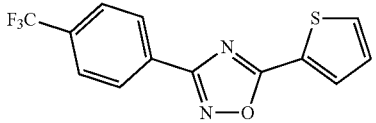 [SMILES: FC(F)(F)c1ccc(-c2noc(-c3cccs3)n2)cc1] | 98 | 85 |
| Fenamiphos | | 100 | 96 |

*Data shows percent control (i.e., galling reduction) relative to the control blank treatment.

TABLE 6B

Fourteen day pre-plant incorporated greenhouse studies of root knot nematode on cucumber plants

| Name | Analog | 8 ka/ha rate* | 4 kg/ha rate* | 2 kg/ha rate* |
|---|---|---|---|---|
| 1822 | 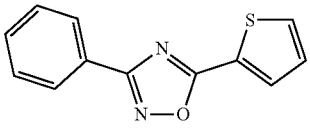 | 100$^a$ | 97$^a$ | 67$^a$ |
| 5467 | 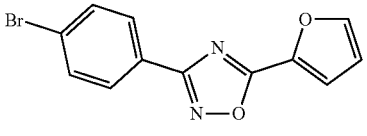 | 100$^a$ | 76$^a$ | 71$^a$ |
| 5479 | 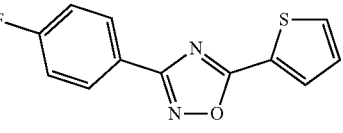 | 100$^a$ | 89$^a$ | 71$^a$ |
| 5523 | 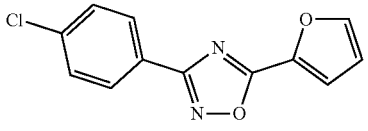 | 99$^a$ | 87$^a$ | 59$^a$ |
| 5527 | 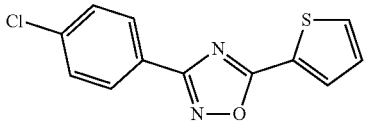 [SMILES: Clc1ccc(-c2noc(-c3cccs3)n2)cc1] | 96$^a$ | 90$^a$ | 57$^a$ |

TABLE 6B-continued

Fourteen day pre-plant incorporated greenhouse studies of root knot nematode on cucumber plants

| Name | Analog | 8 ka/ha rate* | 4 kg/ha rate* | 2 kg/ha rate* |
|---|---|---|---|---|
| 5823 | [4-Cl-2-methylphenyl-1,2,4-oxadiazole-furan structure] | $100^a$ $100^b$ | $98^a$ $94^b$ | $85^a$ |
| 5825 | [4-Br-2-methylphenyl-1,2,4-oxadiazole-furan structure] | $96^a$ | $98^a$ | $69^a$ |
| 5915 | [4-Cl-2-F-phenyl-oxazole-thiophene structure] | $99^b$ | $70^b$ | |
| 5938 | [4-Cl-2-methylphenyl-1,2,4-thiadiazole-furan structure] | $100^b$ | $90^b$ | |
| Fenamiphos | | $100^a$ $100^b$ | $99^a$ $100^b$ | $88^a$ |

*Data shows percent control (i.e., galling reduction) relative to the control blank treatment. Data with the same letters are taken from the same test.

TABLE 6C

Twenty one day pre-plant incorporated greenhouse studies of root knot nematode on cucumber plants

| Name | Analog | 8 ka/ha rate* | 4 kg/ha rate* |
|---|---|---|---|
| 1822 | [phenyl-1,2,4-oxadiazole-thiophene structure] | 95 | 82 |
| 4776 | [4-Br-phenyl-oxazole-thiophene structure] | 80 | 50 |
| Fenamiphos | | 99 | 84 |

*Data shows percent control (i.e., galling reduction) relative to the control blank treatment.

Example 7: Fall Nematicidal Field Testing

Site Establishment

The test site was located at 3511 Highway F in New Melle, Mo., Saint Charles county. The soil was a native prairie/pasture covering silty clay loam soil. Holes were dug using a Bobcat 763 skid loader with a 12-inch auger to a depth of 18 inches. Total volume of each hole was about 1.2 cubic feet. Six cubic yards of topsoil and 9 tons of river sand were purchased from Dardenne Farms Topsoil. Mixing to a ratio of 4 volumes sand to 1 volume soil was accomplished using a trailer-mounted 9 cubic foot concrete mixer. Holes were filled and then re-filled 5 days later after settling. The mixture was 92.5% sand, 2.5% silt, and 5% clay. Organic matter was 0.2% and pH was 6.8.

Plots were planted with squash seeds and had a uniform stand of squash seedlings (2 per plot, 10 cm apart) with the first true leaf emerging just prior to treatment.

Treatment and Inoculation

Treatments were arranged in a block design with the blocks laid out perpendicular to the primary slope and parallel to secondary slope. There are 7 inoculated controls and 5 non-inoculated controls and the distributions of disease severity appeared independent of location.

| Randomized complete block design | | | | ←N | |
|---|---|---|---|---|---|
| blk 1 | blk 2 | blk 3 | blk 4 | blk 5 | blk 6 |
| 1 | 6 | 8 | 3 | 7 | 9 |
| 5 | 10 | 5 | 1 | 9 | 9 |
| 2 | 7 | 9 | 4 | 9 | 8 |
| 4 | 5 | 7 | 2 | 2 | 7 |
| 6 | 2 | 6 | 10 | 8 | 6 |
| 3 | 1 | 3 | 10 | 6 | 5 |
| 8 | 9 | 4 | 8 | 1 | 4 |
| 9 | 3 | 10 | 5 | 4 | 3 |
| 7 | 4 | 1 | 7 | 3 | 2 |
| 10 | 8 | 2 | 6 | 5 | 1 |

Application rates are expressed as kg of active material per hectare, and the mg per plot is based on the surface area of the bored and filled holes (0.000008559 Ha). The DC compounds were formulated immediately before application as follows: 1) the amount required to treat all six replicates was dissolved in 300 ml of acetone, 2) for each plot 50 ml of that solution was added to a graduated cylinder with 2 ml of 12.5% Triton X100 and the volume was raised to 500 ml with tap water. The resultant mix is the same as used in the standard greenhouse assays (10% acetone, 0.05%×100). The oxamyl treatments were prepared from Vydate 2 L formulated the same way. The 500 ml was placed in a watering can and the entire volume was evenly sprinkled over the surface of the plot. No runoff occurred and pooling, if any, was short lived. The final drench volume was 0.58 ml/cm$^2$, compared to 0.2 ml/cm$^2$ used in our greenhouse, however the microplots are much deeper so the drench volume applied per soil volume treated is roughly the same.

TABLE 7A

| | Compound treatment list | | |
|---|---|---|---|
| Name | Analog | Field Rate* | Amount* |
| 4417 | [phenyl-oxazole-thiophene structure] | 2 | 17 |
| 4776 | [Br-phenyl-oxazole-thiophene structure] | 2 | 17 |
| 4559 | [Cl-phenyl-oxadiazole-thiophene structure] | 2 | 17 |
| Oxamyl | | 5 | 43 |
| | | 2 | 17 |
| NT | | | |
| NI | | | |

*Field rate in kg ai per hectare and amount of compound added in mg ai per plot.
NT = non treated (i.e., inoculated with nematodes but not treated with chemicals)
NI = non inoculated (i.e., not treated with chemicals or inoculated with nematodes)

*Meloidogyne incognita* eggs were harvested over a two week period and stored at approximately 5° C. until needed. A stock of 5.6 million vermiform eggs was adjusted to 9000/ml in 620 ml. One day after treatment, two holes were made in each plot about 7 cm apart and equidistant from the squash plants. Five ml of egg suspension was pipetted into each hole, which was then sealed and the plot lightly watered. A total of 90,000 vermiform eggs were added to each plot.

Early Observations

Two days after treatment slight phytotoxicity was seen with the 4417 2 kg/ha treatment. The hypocotyls of affected seedlings were water-soaked at the soil line. Leaf diameter of the first true leaves measured five days after treatment (5 DAT) also showed a slight reduction for the 4417 treatment. None of the compounds appeared to affect the onset of bloom.

TABLE 7B

| | Root Ratings | | | | | |
|---|---|---|---|---|---|---|
| Name | Analog | TW28 | RG28 | RW28 | RG43 | RW43 |
| 4417 | [phenyl-oxazole-thiophene structure] | 97.5 cde | 25.5 abc | 5.3 ab | 38.2 bc | 16.4 a |
| 4776 | [Br-phenyl-oxazole-thiophene structure] | 250.8 abc | 19.0 bc | 7.5 ab | 26.8 cd | 13.0 ab |
| 4559 | [Cl-phenyl-oxadiazole-thiophene structure] | 150.8 cd | 34.2 ab | 6.4 ab | 24.0 cde | 13.2 ab |

TABLE 7B-continued

| | | Root Ratings | | | | |
|---|---|---|---|---|---|---|
| Name | Analog | TW28 | RG28 | RW28 | RG43 | RW43 |
| Oxamyl5 | | 232.1 abcd | 10.5 c | 6.6 ab | 17.3 def | 12.7 b |
| Oxamyl2 | | 136.8 d | 45.0 a | 5.6 b | 42.3 ab | 14.3 ab |
| NT | | 322.4 a | 38.6 a | 7.9 a | 54.7 a | 15.5 ab |
| NI | | 263.1 ab | 0.4 c | 6.9 ab | 0.0 g | 14.4 ab |

*Means with a letter in common are not significantly different at P = 0.1 using Students T test.
TW28 = top weight at 28 days after treatment
RG28 = % root galls at 28 days after treatment
TW28 = root weight at 28 days after treatment
RG43 = % root galls at 43 days after treatment
TW43 = root weight at 43 days after treatment
NT = non treated (i.e., inoculated with nematodes but not treated with chemicals)
NI = non inoculated (i.e., not treated with chemicals or inoculated with nematodes)
Oxamyl5 and Oxamyl2 are oxamyl at 5 kg ai/ha and 2 kg ai/ha respectively The first root evaluation was at 28 DAT. The tops were cut off and weighed immediately in the field, and the roots were carefully dug out so as not to disturb the remaining plant.

The earlier phytotoxicity seen with 4417 is mirrored in a reduction in top weights at 28 DAT. However root weights 28 DAT were not affected and roots weights recorded from the second harvest (43 DAT) revealed no effect from any of the treatments.

Root gall damage was estimated at 28 DAT and 43 DAT using a percent binning scale of 0, 1, 5, 10, 25, 33, 50, 66, 75, 90, and 100% representing the % of root mass significantly impacted by galls. At both sampling times all three compounds provided control of root galling that was numerically superior to oxamyl at an equivalent rate. 4776 was statistically better than oxamyl at both the 28 day and the 43 day time point whereas 4559 was significantly better than oxamyl at the 43 day time point.

In summary all three compounds provide equivalent or superior nematode control to oxamyl under field conditions. Thus these nematicidal analogs are superior to many of the newer more selective nematicide candidates which lack field efficacy at reasonable use rates and are lack sufficient longevity to be of commercial interest.

Example 8: Summer Nematicidal Field Evaluation of Pre-Plant Incorporated (PPI) Compounds for Control of *Meloidogyne incognita* on Squash Test plots of 33 cm diameter holes were bored 41 cm deep into clay soil and filled with a mixture of 80% sand and 20% silt loam soil. Technical compound for each treatment was dissolved in 50 ml acetone containing 250 ul of Triton X-100 surfactant. This solution was added to 450 ml water and poured onto 95 liters of sand/soil mixture in a rotating drum mixer. While continuing to rotate the mixing drum 66 grams of chopped, galled, tomato roots was added and thoroughly distributed. The treated soil was sufficient to fill the top 15 cm of each of the 6 replicate plots, thus simulating a PPI treatment. The plots were then watered lightly and a mixture of *M. incognita* eggs and larvae were injected 5 cm deep at 5 points within the plot (100 k eggs/larvae in 10 ml per plot). Three-week old squash (cv. Liberator III) with 1 fully expanded true leaf was planted 4 days after soil treatment, one per plot.

| | 0-3 vigor 16 DAP | 0-3 vigor 21 DAP | root wgt (g) 31 DAP | top wgt (lbs) 31 DAP | total fruit (lbs) | gall % 31 DAP | feeder root (3 = ave) 31 DAP |
|---|---|---|---|---|---|---|---|
| 5523 4 kg | 3.0 | 3.0 | 26.3 | 1.31 | 1.24 | 26 | 3.0 |
| 5823 4 kg | 3.0 | 3.0 | 22.6 | 1.45 | 1.44 | 3 | 2.7 |
| 5891 4 kg | 3.0 | 2.8 | 27.5 | 1.43 | 1.22 | 28 | 3.0 |
| 5938 4 kg | 2.5 | 2.7 | 24.1 | 1.60 | 1.22 | 9 | 2.7 |
| 5960 4 kg | 3.0 | 3.0 | 32.6 | 1.58 | 1.61 | 24 | 3.3 |
| fosthiazate 2 kg | 3.0 | 3.0 | 26.4 | 2.01 | 1.25 | 5 | 2.3 |
| oxamyl 4 kg | 2.7 | 2.5 | 37.0 | 1.16 | 1.09 | 85 | 3.0 |
| Blank | 1.5 | 1.2 | 23.4 | 0.30 | 0.38 | 90 | 2.7 |

Chopped gall inoculum combined with eggs/juveniles provided high pressure and rapid development of symptoms. PPI applications of DC5823 and DC5938 provided excellent control at 4 kg/ha. DC5523, DC5891, and DC5960 also provided significant control at 4 kg/ha.

Example 9: Seed Treatment Test of Root Knot Nematode on Cucumber Plants and Soybean Cyst Nematode on Soybean Plants For a given concentration the chemical is dissolved in 500 ul of acetone and one gram of cucumber seed (RKN test) or soybean seed (SCN test) is added (e.g., 20 mg active ingredient in 500 ul acetone plus 1 gram of seed). The seed solutions are agitated until all seeds were thoroughly covered with the chemical solution. The acetone is then allowed to evaporate by air drying the seeds. The seeds are planted in 2-inch pots containing sandy soil and then the pots are inoculated with 1000 *Meloidogyne incognita* (RKN) or 1000 *Heterodera glycines* (SCN) eggs per pot three days after planting. Plants are rated for galling 14 days after egg inoculation for RKN or 28 days after egg inoculation for SCN.

TABLE 9A

Seed treatment activity against root knot nematode using cucumber seeds

| Name | Analog | 20 mg ai/gram seed* |
|---|---|---|
| 1822 | [3-phenyl-5-(thiophen-2-yl)-1,2,4-oxadiazole structure] | 76 |
| 4775 | [5-(4-fluorophenyl)-2-(thiophen-2-yl)oxazole structure] | 77 |
| 4776 | [5-(4-bromophenyl)-2-(thiophen-2-yl)oxazole structure] | 58 |
| Abamectin[#] | | 84 |

*Data shows percent control (i.e., galling reduction) relative to the control blank treatment.
[#]Abamectin positive control at 10 mg ai/gram seed.

TABLE 9B

Seed treatment activity against soybean cyst nematode using soybean seeds

| Name | Analog | 1.5 mg* | 0.375 mg* |
|---|---|---|---|
| 5527 | [Cl-phenyl oxadiazole-thiophene structure] | 71[a] | 43[a] |
| 5479 | [F-phenyl oxadiazole-thiophene structure] | 88[a] / 83[b] | 67[a] / 69[b] |
| 1822 | [phenyl oxadiazole-thiophene structure] | 70[a] | 58[a] |
| 5847 | [F,F-phenyl oxadiazole-thiophene structure] | 80[b] | 66[b] |
| 5878 | [F,F,F-phenyl oxadiazole-thiophene structure] | 77[b] | 43[b] |
| 5953 | [Cl,F-phenyl thiadiazole-furan structure] | 77[b] | 44[b] |
| Oxamyl | | — | — |
| | | 71[b] | -4[b] |
| Thiodicarb | | -23[a] | 6[a] |
| Abamectin | | -24[a] | -14[a] |

*Data shows percent cyst reduction relative to control blank treatment. Rates are mg ai/gram seed. Data with the same letters are taken from the same test.

Oxadiazole, thiadiazole and oxazole analogs are versatile nematicides showing activity as seed treatments in addition to drench applications and soil pre-incorporation methods.

Example 10: The Claimed Structures do not Induce an Apoptosis Marker in Mammalian Cells and do not Kill Nematodes by Causing Apoptosis Previous studies have shown that induction of the pro-apoptotic caspase-3 protease through the cleavage of specific fluorogenic substrates is a reliable method of measuring the induction of apoptosis, and certain chloro and bromo substituted thiophene and furan oxadiazoles were identified after high-throughput screening for caspase-3 induction in mammalian cells (Zhang H Z, Kasibhatla S, Kuemmerle J, Kemnitzer W, Ollis-Mason K, Qiu L, Crogan-Grundy C, Tseng B, Drewe J, Cai S X. Discovery and structure-activity relationship of 3-aryl-5-aryl-1,2,4-oxadiazoles as a new series of apoptosis inducers and potential anticancer agents. J Med Chem. 2005 48(16):5215-23).

To evaluate whether the compound classes of this invention are able to induce apoptosis, caspase-3 activity was determined after compound exposure in rat hepatoma derived H4IIE cells using a caspase substrate (DEVD, Asp-Glu-Val-Asp) labeled with a fluorescent molecule, 7-Amino-4-methylcoumarin (AMC). Caspase 3 cleaves the tetrapeptide between D and AMC, thus releasing the fluorogenic green AMC. Following the test article exposure to cells in 96-well plates, medium was aspirated from plates and PBS added to each well. Plates were stored at −80° C. to lyse cells and store samples until further analysis. On the day of analysis, plates were removed from freezer and thawed. Caspase buffer with fluorescent substrate was added to each well and incubated at room temperature for one hour. AMC release was measured in a spectrofluorometer at an excitation wavelength of 360 nm and an emission wavelength of 460 nm. Values are expressed as relative fluorescent units (RFU). In contrast to paclitaxel, camptothecin, and staurosporine, which were reportedly capable of inducing apoptosis in a variety of cell lines at or below doses of 1 μM doses, no induction of caspase-3 is observed for DC1822, DC5823, DC5915, and DC5938 at concentrations up to 300 μM in this system.

To confirm that these compounds do not affect nematodes by induction of apoptosis, Caenorhabditis elegans mutants defective in the apoptotic pathway, ced-3(n717) and ced-4 (N1162) mutants (Ellis H M, Horvitz H R. Genetic control of programmed cell death in the nematode C. elegans. 1986

Cell 44:817-829), were evaluated for susceptibility to 10 μg/ml DC5823 on NGM agar plates. No observable phenotypic difference in susceptibility between the wild-type *C. elegans* strain (N2 Bristol) and the ced-3 and ced-4 mutants were observed, including time to mortality.

These data indicate that the claimed structures do not affect apoptosis in either mammalian cells or nematodes.

Example 11: Description of Synthesis of the Compounds of the Formula I to VII

The compounds of this invention of the Formulas I to VII may be prepared using methods known to those skilled in the art. Specifically, the compounds of this invention with Formulae Ia and Ib can be prepared as illustrated by the exemplary reaction in Scheme 1. The alpha aminoketones 3 are prepared from the acetophenones 1 in a two-step procedure that involves bromination with 4(-dimethylamino) pyridine tribromide and subsequent amination of the bromide intermediate 2 with sodium diformylamide. The aminoketone 3 is then reacted with an appropriate acyl chloride 4 to yield the acylaminoketone 5. A cyclization of the linear precursor 5 to the 2,5-disubstituted-1,3-oxazole analog 6 is accomplished with phosporousoxychloride in DMF in good yields.

Scheme 1: Synthetic scheme to compounds of the Formula Ia and Ib

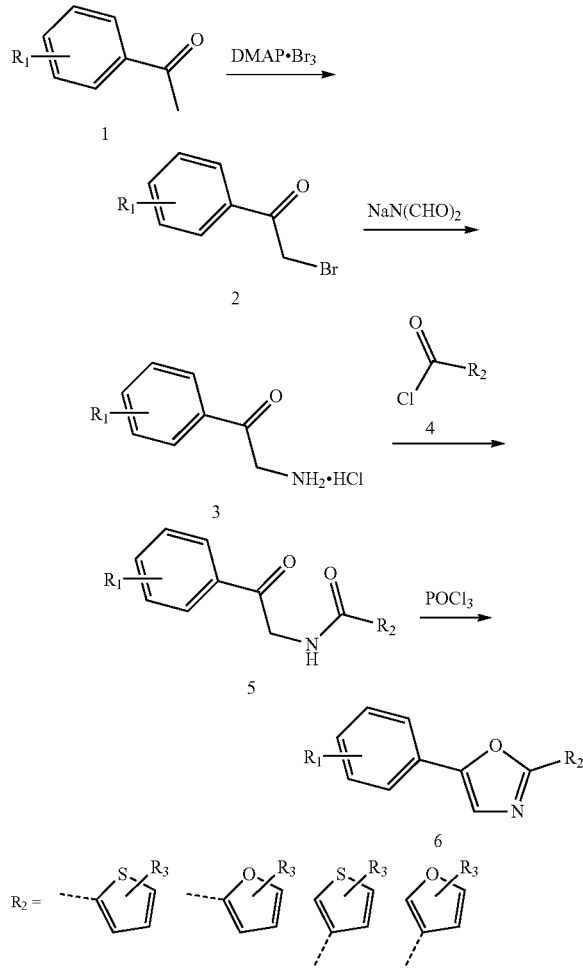

Specifically, the compounds of this invention with Formulae IIa and IIb can be prepared as illustrated by the exemplary reaction in Scheme 2. The alpha aminoketone 2 is prepared from the bromide precursor 1 by amination with sodium diformylamide and then reacted with acyl chloride 3 to yield the acylaminoketone 4. A cyclization of the linear precursor 4 to the 2,5-disubstituted-1,3-oxazole analog 5 is accomplished with phosporousoxychloride in DMF in good yields.

Scheme 2: Synthetic scheme to compounds of the Formula IIa and IIb

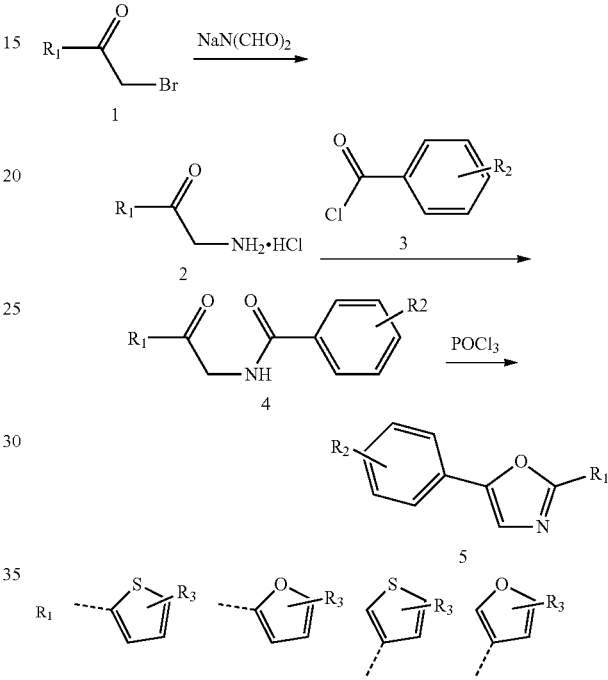

Specifically, the compounds of this invention with Formulae IIIa and III b can be prepared as illustrated by the exemplary reaction in Scheme 3. The benzohydrazide 1 is reacted with the acyl chloride 2 in chloroform in the presence of trietylamine (TEA) at ambient temperature to give acyl benzohydrazide 3. A cyclization of the diacylhydrazine 3 to the 2,5-disubstituted-1,3,4-oxadizaole compound 4 is accomplished with phosporouschloride (POCl3) in DMF.

Scheme 3: Synthetic scheme to compounds of the Formula IIIa and IIIb

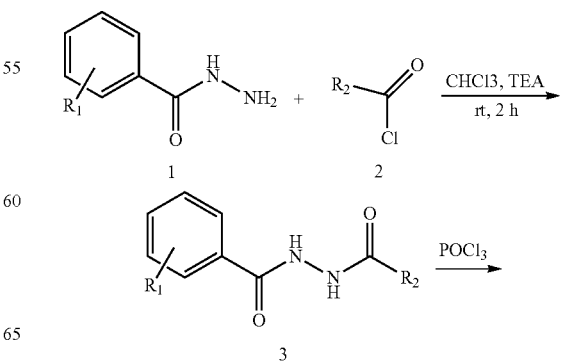

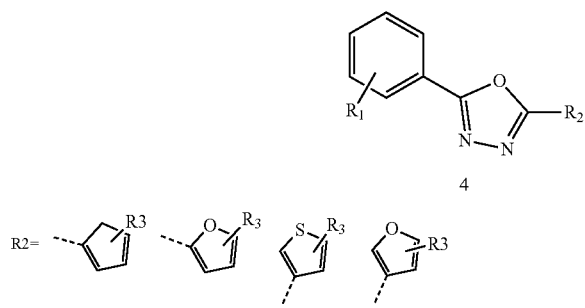

Specifically, the compounds of this invention with Formulae IVa and IVb can be prepared as illustrated by the exemplary reaction in Scheme 4. The benzonitrle 1 is converted to the corresponding hydroxyimidate 2 when reacted with hydroxylamine hydrochloride in the presence of DIEA in methanol at room temperature overnight. Then the benzohydroxyimidate 2 is acylated with an appropriate furan or thiophene carbonyl chloride (R2-CO—Y) in the presence of pyridine, followed with DCC dehydration to give the 3,5-disubstituted-1,2,4-oxadiazole product.

Scheme 4: Synthetic scheme to compounds of the Formula IVa and IVb

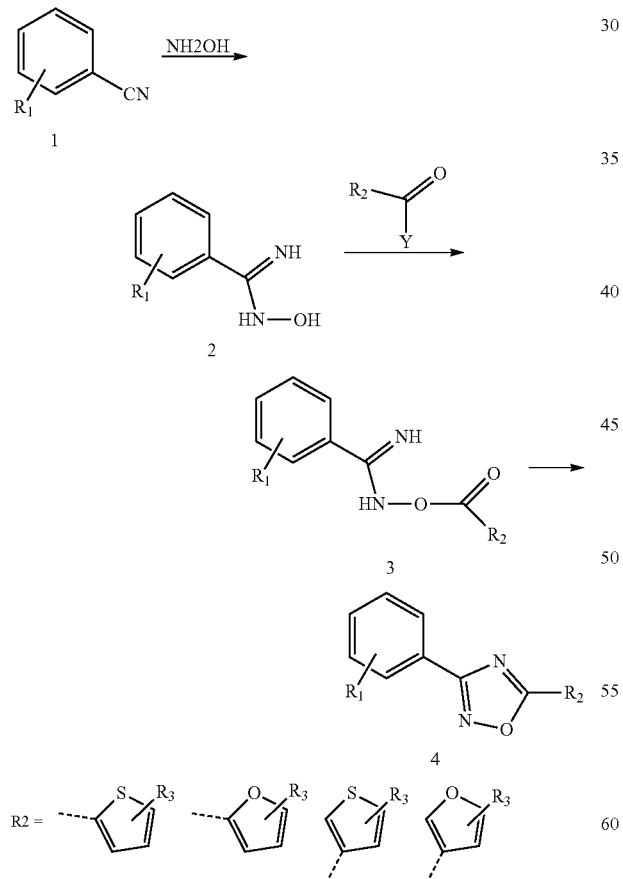

Specifically, the compounds of this invention with Formulae Va and Vb can be prepared as illustrated by the exemplary reaction in Scheme 5.

Scheme 5: Synthetic schemes to compounds of the Formula Va and Vb

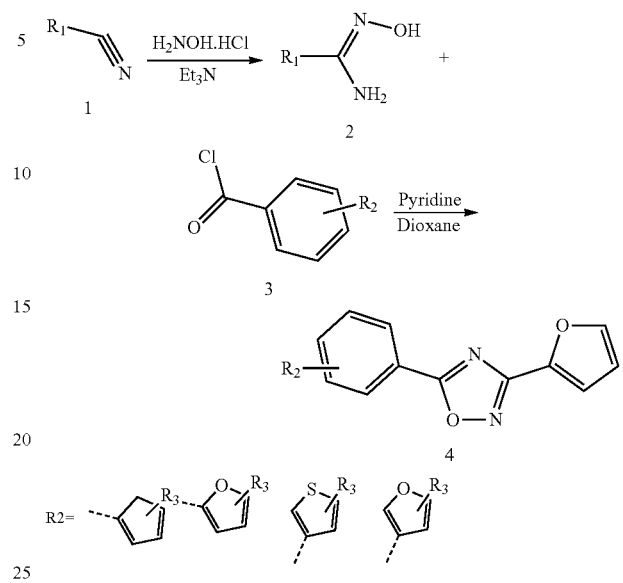

First, the appropriate analog of furan or thiophene nitrile 1 is converted to the corresponding hydroxyimidate 2 by reacting with hydroxylamine in methanol in the presence of DIEA. Then, the intermediate 2 is reacted with the appropriately substituted benzoyl chloride 3 in pyridine-dioxane to give the desired 3,5-disubstituted-1,2,4-oxadiazole product 4.

Specifically, the compounds of this invention with Formulae VIa and VIb can be prepared as illustrated by the exemplary reaction in Scheme 6. The synthesis starts with the reaction of an appropriate benzamide substrate 1 with chlorocarbonylsulfenyl chloride to yield the oxathiazolone compound 2. In the next step the oxathiazoline intermediate 2 is reacted with an appropriate furan or thiophene nitrile in toluene under microwave conditions to give the desired 3,5-disubstituted-1,2,4-thiadiazole product 3.

Scheme 6: Synthetic scheme to compounds of the Formula VIa and VIb

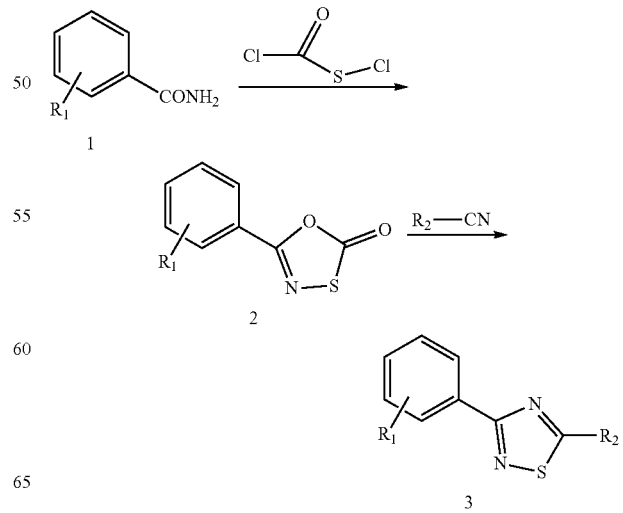

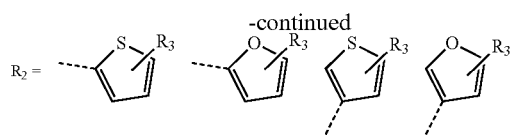

Specifically, the compounds of this invention with Formulae VIIa and VIIb can be prepared as illustrated by the exemplary reaction in Scheme 7. An appropriate furan or thiophene carboxamide substrate 1 is converted to the oxathiazolone intermediate by reacting with chlorocarbonylsulfenyl chloride. Then, the oxathiazoline intermediate 2 is reacted with an appropriate benzonitrile compound in toluene under microwave conditions to give the desired 3,5-disubstituted-1,2,4-thiadiazole product 4.

Scheme 7: Synthetic scheme to compounds of the Formula VIIa and VIIb

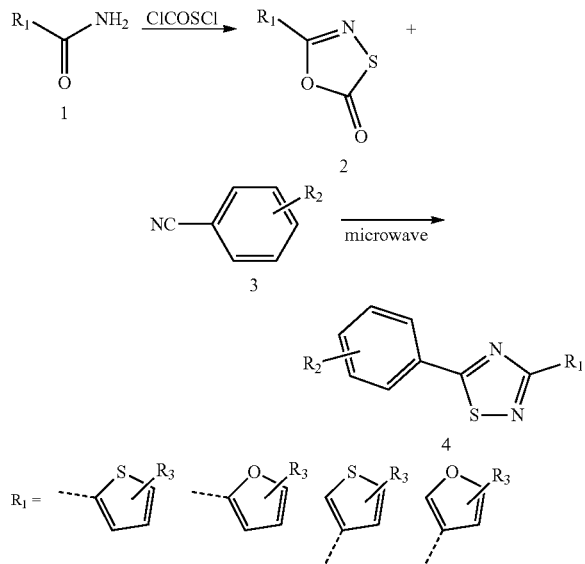

Formula Ia Example: 5-(4-chloro-2-fluorophenyl)-2-(thiophen-2-yl)oxazole

A mixture of 4'-chloro-2'-fluoroacetophenone (17.5 g, 100 mmol), 4-(dimethylamino)pyridine tribromide (40.0 g, 110 mmol) and acetic acid (100 mL) was stirred at room temperature for 24 h. Water (150 mL) was added and after stirring for 30 min the precipitated solid was collected by filtration, washed with water, and dried in vacuo to give the desired bromide intermediate as a white solid (24 g, 95%).

To a solution of the bromide compound (24 g, 90 mmol) in acetonitrile (300 mL) was added sodium diformylamide (9.0 g, 95 mmol). The mixture was heated to reflux for 2 h and cooled to r.t overnight. The mixture was filtered to remove NaBr. The filtrate was concentrated to give diformylamide intermediate as a brown oil, 23.6 g. EtOH (300 mL) and 30% HCl (90 mL) were added and the mixture was stirred at 50° C. for 5 h and cooled to room temperature overnight, during which time the product crystallized out. The solid was collected by filtration, washed with dichloromethane, and dried to constant weight to give the desired aminoketone hydrochloride as white solid (6.3 g, 31%). that was sued as is in the next step.

The synthesis of acylamino ketone was performed as described in the literature (*J. Med. Chem.* 1986, 29, 333-341). A suspension of 2-amino-1-(4-chloro-2-fluorophenyl) ethanone hydrochloride (6.3 g, 28 mmol) in water (50 mL) and EtOAc (100 mL) was cooled in an ice-bath. $NaHCO_3$ (11.9 g, 140 mmol) was added in portions, followed by 2-thiophene carbonyl chloride (4.25 g, 29 mmol). The mixture was stirred at room temperature for 16 h. Water (50 mL) was added and the mixture was extracted with EtOAc (2×50 mL). The organic layers were combined, washed with brine, dried ($MgSO_4$), filtered, and concentrated in vacuo to give acylamino ketone 5 as yellow solid (7.7 g, 92%). The organic layers were combined, dried ($MgSO_4$), and concentrated in vacuo to give crude product, 7.8 g, which was purified by crystallization from EtOH (25 mL). Yield 5.0 g (69%) of yellow solid.

Molecular Formula: $C_{13}H_7ClFNOS$; MW 279.72

HPLC-ESMS: $t_R$=6.04 min; m/z: 279.9 (M+H); HPLC purity 98.0% (216 nm); 99% (250 nm)

$^1$H-NMR (300 MHz, $CDCl_3$): 7.74-7.85 (m, 2H), 7.52-7.56 (m, 1H), 7.46-7.51 (m, 1H), 7.21-7.31 (m, 2H), 7.14-7.20 (m, 1H)

Formula IIa Example: 2-(4-chloro-2-fluorophenyl)-5-(thiophen-2-yl) oxazole

A mixture of 2-(2-bromoacetyl)thiophene (2.05 g, 10 mmol), sodium diformyl amide (1.05 g, 11 mmol) and acetonitrile (20 mL) was heated to reflux for 4 h. The mixture was cooled to r.t. and filtered to remove NaBr. The filtrate was concentrated in vacuo to give a brown oil, 2.0 g. EtOH 930 mL) was added followed by concentrated HCl (30%, 10 mL). The mixture was stirred at r.t. overnight. Concentration in vacuo gave a sticky solid, 2.1 g. The resulted aminoketone hydrochloride was contaminated by some $NH_4Cl$ (based on H1-NMR spectra) and used as is in the next step.

A mixture of the crude amine.HCl in EtOAc (40 mL) and water (20 mL) was vigorously stirred and cooled in ice-water bath. $NaHCO_3$ (8.3 g, 100 mmol) was added, followed by 4-chloro-2-fluorobenzoyl chloride (1.9 g, 10 mmol). The mixture was stirred at r.t. overnight. The layers were separated. The water layer was extracted with EtOAc (50 mL). The combined organic layers were washed with water, dried ($MgSO_4$) and concentrated to a brown solid, 2.0 g. The resulted crude product was a mixture of the desired acylaminoketone and 4-chloro-2-fluorobenzamide (formed by reaction of ammonium chloride present in the starting aminoketo compound with the acyl chloride).

The acylaminoketone intermediate was dissolved n DMF (25 mL). and then $POCl_3$ (2.3 g, 15 mmol) was added and the mixture was stirred at r.t. for 2.5 days. Ice-water was added and the mixture was extracted with EtOAc (3×50 mL). The organic layer was washed with water (3×30 mL), dried ($MgSO_4$) and concentrated to a brown solid/oil, 1.7 g. A column chromatography (Hep/EtOAc 2/1) gave 1.0 g of a solid which was still not pure. Crystallization from MeOH (5 mL) gave pure (0.6 g, 22%) 2-(4-chloro-2-fluorophenyl)-5-(thiophen-2-yl)oxazole with HPLC purity>99.0% (215 and 254 nm).

Molecular Formula: $C_{13}H_7ClFNOS$, MW 279.72; LC-MS: $t_R$=9.46 min m/z: 279.9 (M+H).

$^1$H-NMR (300 MHz, $CDCl_3$): 7.98-8.08 (m, 1H), 7.22-7.42 (m, 5H), 7.08-7.14 (m, 1H)

Formula IIIa Example: 2-(4-Chloro-phenyl)-5-thiophen-2-yl-[1,3,4]oxadiazole

To 250 mL round bottom flask was added 2.0 g (11.7 mmol, 1 eq) of 4-chlorobenzhydrazide (1) in 100 mL of amelene stabilized chloroform, followed by addition of 4 mL (29.25 mmol, 2.5 eq) of TEA. Then, 1.4 mL (12.87 mmol, 1.1 eq) of 2-thiophenecarbonyl chloride (2) was added drop-wise and the mixture was stirred at ambient temperature for 1 h. Reaction progress was monitored by LCMS on a twelve minute gradient. The formed white precipitate was filtered, washed with chloroform and then dried on the high vacuum for two hours. The resulting material was confirmed to be the desired diacylhydrazide and was used in the next step without further purification. The crude diacyl-hydrazide was dissolved in 60 mL of $POCl_3$ under heating. The resulting mixture was then heated under reflux in oil bath (100-110° C.) for 5-7 h. The reaction progress was monitored by LCMS on a twelve minute gradient. Once the cyclization reaction was completed as determined by LCMS, $POCl_3$ was carefully evaporated in vacuum and the reaction was then neutralized with a 1 N solution of ammonium hydroxide. The product was extracted with ethyl acetate (300 mL) from saturated solution of $NaHCO_3$ (200 mL), washed with a brine (2×200 mL), then dried over sodium sulfate, filtered and evaporated to dryness. The product was purified by flash column chromatography (hexane→12% ethyl acetate/hexane), and then recrystallized from mixture of hexane/ethyl acetate (5:1) to give 1.3 g of the desired compound 2-(4-Chloro-phenyl)-5-thiophen-2-yl-[1,3,4]oxadiazole (42%) as a white solid.

Chemical Formula: $C_{12}H_7ClN_2OS$; MW 262.71; ESMS: m/z 263 (M+H);

$^1$H-NMR (250 MHz, $D_6$-DMSO): 8.08-8.12 (m, 2H), 7.96-7.99 (m, 2H), 7.69-7.72 (m, 2H), 7.32-7.35 (m, 1H)

Formula IVa Example: 3-(4-Chloro-2-methyl-phenyl)-5-furan-2-yl-[1,2,4-]oxadiazole In a 500 mL round-bottom flask, 4-chloro-2-methylbenzonitrile (10 g, 66 mmol) was dissolved in 200 mL of methanol. To the mixture was added hydroxylammonium chloride (4.56 g, 66 mmol) followed by DIEA (diisopropylethylamine) (23 mL, 132 mmol). The mixture was heated at reflux for overnight. The solvents were removed. The residue was dissolved in 200 mL of $CHCl_3$. To the mixture was added 2-furoyl chloride (10.5 ml, 66 mmol) followed by DIEA (23 mL, 132 mmol). After reaction completion, the mixture was extracted with chloroform and water. The organic layer was separated, washed with brine, dried over $Na_2SO_4$, filtered and evaporated to dryness. The residue was dissolved in 200 mL of dioxanes. To the mixture was added 1 eq of DIC (N, N'-diisopropylcarbodiimide) followed by 1 eq of DIEA. The mixture was then heated at reflux overnight. After reaction completion, the mixture was cooled down. The solvents were removed in vacuo. The residue was then extracted with ethyl acetate and water. The organic layer was separated, washed with brine, dried over $Na_2SO_4$, filtered and evaporated to dryness. The crude was purified by flash chromatography on silica gel in a 0-20% ethyl acetate/hexanes gradient to afford 4.96 g of the desired compound 3-(4-Chloro-2-methyl-phenyl)-5-furan-2-yl-[1,2,4-]oxadiazole as a white powder in an overall yield of 28.8%.

Molecular Formula: $C_{13}H_9ClN_2O_2$; MW 260.04; HPLC purity 99.9% (254 nm); LC-ESMS: $t_R$=7.55 min; m/z 261.1 (M+1);

$^1$H-NMR (250 MHz, $D_6$-DMSO): 8.18-8.19 (m, 1H), 7.98-8.01 (d, J=8.3, 1H), 7.64-7.65 (m, 1H), 7.52-7.56 (m, 1H), 7.46-7.50 (m, 1H), 6.87-6.89 (m, 1H), 2.59 (s, 3H)

Formula IVa Example: 3-(4-Bromo-2-methyl-phenyl)-5-furan-2-yl-[1,2,4]-oxadiazole In a 500 mL round-bottom flask, 4-bromo-2-methylbenzonitrile (5 g, 25 mmol) was dissolved in 200 mL of methanol. To the mixture was added hydroxylammonium chloride (1.72 g, 25 mmol) followed by DIEA (diisopropylethylamine) (8.7 mL, 50 mmol). The mixture was heated at reflux for overnight. The solvents were removed. The residue was dissolved in 200 mL of $CHCl_3$. To the mixture was added 2-furoyl chloride (3.97 ml, 25 mmol) followed by DIEA (8.7 mL, 50 mmol). After reaction completion, the mixture was extracted with chloroform and water. The organic layer was separated, washed with brine, dried over $Na_2SO_4$, filtered and evaporated to dryness. The residue was dissolved in 200 mL of dioxanes. To the mixture was added 1 eq of DIC (N, N'-diisopropylcarbodiimide) followed by 1 eq of DIEA. The mixture was then heated at reflux overnight. After reaction completion, the mixture was cooled down. The solvents were removed in vacuo. The residue was then extracted with ethyl acetate and water. The organic layer was separated, washed with brine, dried over $Na_2SO_4$, filtered and evaporated to dryness. The crude was purified by flash chromatography on silica gel in a 0-20% ethyl acetate/hexanes gradient to afford 2.23 g of the desired compound 3-(4-Bromo-2-methyl-phenyl)-5-furan-2-yl-[1,2,4]-oxadiazole as a white powder in an overall yield of 36%.

Chemical Formula: $C_{13}H_9BrN_2O_2$; MW: 305.13; HPLC Purity>99.0%; (254 nm) ESMS: $t_R$=7.81 min; m/z 305.1 (M+1);

$^1$H-NMR (250 MHz, $D_6$-DMSO): 8.18-8.19 (m, 1H), 7.92 (d, J=8.3, 1H), 7.58-7.70 (m, 3H), 6.86-6.90 (m, 1H), 2.59 (s, 3H)

Formula Va Example: 5-(4-chloro-2-methylphenyl)-3-(furan-2-yl)-1,2,4-oxadiazole

To a solution of 2-furonitrile (1.9 g, 20 mmol) in MeOH (50 mL) was added hydroxylamine hydrochloride (1.4 g, 20 mmol) and triethylamine (2.1 g, 20 mmol). The mixture was heated to reflux overnight. After cooling to room temperature the mixture was concentrated in vacuo. The residue was stirred with EtOAc (50 mL). The solid was filtered off and the filtrate was concentrated to a thick oil, 2.5 g (99%). The H-NMR spectra was in accordance with the desired hydroxyamidine compound which was contaminated with $Et_3N.HCl$. The crude product resulted in this reaction was used without the purification in the next step.

To a suspension of 4-chloro-2-methylbenzoic acid (3.4 g, 20 mmol) in dichloromethane (50 mL) was added one drop of DMF followed by oxalylchloride (3.2 g, 25 mmol). The mixture was stirred overnight during which time all solid dissolved. The mixture was concentrated in vacuo and stripped with dichloromethane to remove excess oxalylchloride. The residual acid chloride was taken in dioxane/pyridine (10/1, 55 mL) and hydroxyamidine compound (2.5 g, 20 mmol) was added. The mixture was heated to reflux for 3 h. After cooling to room temperature, water was added (100 mL) and the resulting solid was collected by filtration and dried to give 6.2 g of crude product. Recrystallizaton from MeOH (40 mL) gave pure 5-(4-chloro-2-methylphenyl)-3-(furan-2-yl)-1,2,4-oxadiazole 2.6 g (yield 47%).

Molecular Formula: $C_{13}H_9ClN_2O_2$; MW 260.04; HPLC purity: >99.9% (216 nm); 99.9% (324 nm); LC-ESMS: $t_R$=9.46 min; m/z 261.1 (M+1);

$^1$H-NMR (300 MHz, $CDCl_3$): 8.10 (dd, J=8.1, 1H), 7.63-7.66 (m, 1H), 7.32-7.42 (m, 2H), 7.18-7.22 (d d, J=2.7, 0.9, 1H), 6.58-6.62 (m, 1H), 2.89 (s, 3H)

Formula VIa Example: (2,4-dichlorophenyl)-5-(furan-2-yl)-1,2,4-thiadiazole

A mixture of 2,4-dichlorobenzamide (25 g, 131.5 mmol) and chlorocarbonylsulfenylchloride (19 g, 145 mmol) in toluene (150 mL) was heated to reflux for 4 h (HCl-gas formation was observed with pH paper). After cooling to r.t. the mixture was concentrated in vacuo to give the desired oxathiazolone compound as an off-white solid (32.4 g, 99%). that was used in the next without purification. In a 20 mL vial a mixture of oxathiazolone 8a (2 g, 8 mmol) and 2-furonitrile (10 g, 107 mmol) was heated in the microwave at 190° C. for 20 min. The reaction was performed 10 times and the combined mixture was distilled (Kugerrohr) at 100° C./20 mbar to remove excess 2-furonitrile (the recovered 2-furonitrile was used again). The mixture was further distilled at 150° C./10 mbar to remove the byproduct nitrile 10 (yellow solid, 6.5 g, 47%). The residue of the distillation (circa 10 g) was taken in dichloromethane (50 mL), filtered and the filtrate concentrated to a brown solid, 8 g. Recrystallization by dissolution in hot MeOH (50 mL) and addition of water (10 mL) gave pure (2,4-dichlorophenyl)-5-(furan-2-yl)-1,2,4-thiadiazole as brown solid, 4.7 g, in a 20% yield.

Chemical Formula: $C_{12}H_6C_{12}N_2OS$; MW: 297.16; HPLC-ESMS: $t_R$=6.5; m/z: 296.96; 298.95 (M+1); HPLC purity>99% (221 nm), >99% (263 nm), >99.0% (306 nm)

$^1$H-NMR (300 MHz, CDCl$_3$): 7.90 (dd, J=8.4, 1H), 7.57-7.58 (m, 1H), 7.29 (dd, J=8.4, 1.8) 7.48, d, J=1.8, 1H), 7.15-7.20 (m, 1H), 6.55-6.59 (m, 1H)

Formula VIa Example: 3-(4-chloro-2-methylphenyl)-5-(furan-2-yl)-1,2,4-thiadiazole A magnetically stirred mixture of acid 4-chloro-2-methylbenzoic acid (50 g, 0.29 mol), dichloromethane (200 mL), and 0.5 mL DMF was cooled in an ice-bath. The cooler was connected to a gas absorption trap. Oxalyl chloride (44.5 g, 0.35 mmol) was added dropwise in 1 h. The mixture was stirred at r.t. overnight during which time all solid dissolved. The solution was concentrated in vacuo and stripped with dichloromethane to remove excess oxalyl chloride. The residue was taken in THF (200 mL) and mechanically stirred in an ice-water bath. Aqueous 25% ammonia (100 mL) was added in 15 min, which resulted in the formation of a precipitate. The THF was removed with the rotavap and extra water (100 mL) was added. The suspension was stirred at r.t. overnight. The solid was collected by filtration and dried in vacuo to give 2-methyl-4-chlorobenzamide (43.7 g, yield 89%) that was used without purification in the next step.

A mechanically stirred mixture of 2-methyl-4-chlorobenzamide (31.35 g, 185 mmol), toluene (400 mL), and chlorocarbonylsulfenylchloride (25 g, 190 mmol) was heated to reflux for 3 h. After cooling to room temperature the mixture was concentrated in vacuo to give a yellow solid 40 g (95%). H-NMR showed that this was a mixture of the desired oxathiazolone compound and nitrie by-product and starting amide in a ratio 85:10:5. This mixture was used in the next step without further purification.

The crude oxathiazolone compound (2.0 g, 8.8 mmol) and 2-furonitrile (16 g, 170 mmol) were mixed and heated for 20 min at 190° C. in the microwave. Ten batches were combined and Kugelrohr distilled at 100° C./30 mbar to recover excess 2-furonitrile (used again in next microwave reactions). The residue was further distilled at 150° C./20 mbar to remove the nitrile by-product. The residue, 5.5 g was combined with the residue of another ten microwave reactions (4.5 g) and purified by column chromatography. The resulting 4.5 g (85% pure by HPLC) was recrystallized from MeOH (50 mL) to give pure 3-(4-chloro-2-methylphenyl)-5-(furan-2-yl)-1,2,4-thiadiazole as light brown solid, 3.6 g (7.5% yield).

Chemical Formula: $C_{13}H_9ClN_2OS$; MW: 278.7; HPLC-ESMS: $t_R$=6.36 min and m/z 277.0 (M+1); HPLC purity: >95% (220 nm) 95% (270 nm).

$^1$H-NMR (300 MHz, CDCl$_3$): 8.06, (dd, J=7.8, 1H), 7.62-7.63 (m, 1H), 7.22-7.31 (m, 3H), 6.61-6.63 (m, 1H), 2.66 (s, 3H)

Formula VIa Example: 3-(4-chlorophenyl)-5-(furan-2-yl)-1,2,4-thiadiazole

A mechanically stirred mixture of 4-chlorobenzamide (20.23 g, 130 mmol), toluene (150 mL), and chlorocarbonylsulfenylchloride (19 g, 145 mmol) was heated to reflux for 3 h. After cooling to r.t. the mixture was concentrated in vacuo to give a yellow solid foam, 27.65 g (100%). H-NMR showed that this was almost pure oxathiazolone compound that was used as is in the next step. The oxathiazolone compound (1.71 g, 8 mmol) and 2-furonitrile (15 g, 160 mmol) were mixed and heated for 20 min at 190° C. in the microwave. Ten batches were combined and Kugelrohr distilled at 100° C./30 mbar to recover excess 2-furonitrile (used again in next microwave reactions). The residue was further distilled at 150° C./20 mbar to remove the nitrile byproduct. The residue, 5 g, was recrystallized from MeOH to give 3.5 g of solid. This was combined with the residue of another 5 microwave reactions (2.6 g) and purified by column chromatography. The resulting 4.4 g (90% pure by HPLC) was recrystallized from Heptane/EtOAc=7/1 (50 mL) to give pure 3-(4-chlorophenyl)-5-(furan-2-yl)-1,2,4-thiadiazole as light brown solid, 3.35 g (10% yield).

Chemical Formula: $C_{12}H_7ClN_2OS$; Molecular Weight: 262.71; HPLC-ESMS: $t_R$=6.06 min; m/z: 263.00, 264.99 (M+1)

$^1$H-NMR (300 MHz, CDCl$_3$): 8.24-8.33 (m, 2H), 7.63-7.65 (m, 1H), 7.42-7.50 (m, 2H), 7.23-7.28 (m, 1H), 6.62-64 (m, 1H)

Formula VIIa Example: 5-(2-chloro-4-methylphenyl)-3-(furan-2-yl)-1,2,4-thiadiazole A magnetically stirred mixture of 2-furoylamide (prepared from 2-furoylchloride and aqueous ammonia, 1.13 g, 10 mmol) and chlorocarbonylsulfenylchloride (2.0 g, 15 mol) in toluene (20 mL) was heated to reflux for 4 h. After cooling to room temperature the mixture was concentrated to give 1.7 g of the desired oxathiazolone as a yellow solid (almost in a quantitative yield) that was used in the next step without further purification.

A mixture of the oxathiazolone compound (170 mg, 1 mmol) and 4-chloro-2-methylbenzonitrile (3.03 g, 20 mmol) was heated in the microwave at 190° C. for 20 min. A second reaction was performed and the mixtures were combined. Excess of the nitrile by-product (furonitrile) were removed in vacuo (120° C., 0.3 mbar). The residual brown solid (100 mg) was taken in hot MeOH (10 mL) and decanted from insoluble material (presumably sulphur). The MeOH solution was left at room temperature overnight. The precipitated solid was collected and dried to give compound 5-(2-chloro-4-methylphenyl)-3-(furan-2-yl)-1,2,4-thiadiazole as brown solid, 40 mg (7%). NMR conform structure.

Chemical Formula: $C_{13}H_9ClN_2OS$; MW: 278.7; HPLC-ESMS: $t_R$=6.36 min and m/z 277.01 (M+1); HPLC purity: 93.5 (216 nm) 91% (324 nm); $^1$H-NMR (300 MHz, CDCl$_3$): 7.87 (dd, J=8.1, 1H), 7.51-7.60 (m, 1H), 7.24-7.32 (m, 2H), 7.15-7.20 (m, 1H), 6.50-6.56 (m, 1H), 2.58 (s, 3H)

What is claimed is:

1. A nematicidal composition comprising:
an effective amount of a compound of Formula IV, Formula V, or a salt thereof

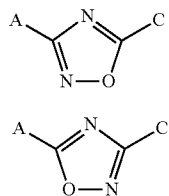

Formula IV

Formula V wherein,
A is phenyl, pyrazyl, oxazolyl or isoxazolyl, each of which can be optionally independently substituted with one or more substituents selected from the group consisting of halogen, $CF_3$, $CH_3$, $OCF_3$, $OCH_3$, CN, and C(H)O; and
C is thienyl, furanyl, oxazolyl or isoxazolyl, each of which can be optionally independently substituted with one or more substituents selected from the group consisting of fluorine, chlorine, $CH_3$, and $OCF_3$; and
one or more of an insecticide, a fungicide, a herbicide, or another pesticide selected from the group consisting of an avermectin, milbemycin, imidacloprid, aldicarb, oxamyl, fenamiphos, fosthiazate, metam sodium, etridiazole, penta-chloro-nitrobenzene (PCNB), flutolanil, metalaxyl, mefonoxam, fosetyl-al, silthiofam, fludioxonil, myclobutanil, azoxystrobin, chlorothalonil, propiconazole, tebuconazole, pyraclostrobin, trifloxysulfuron, glyphosate, and halosulfuron.

2. The composition of claim 1 wherein A is phenyl.
3. The composition of claim 1 wherein A is pyrazyl.
4. The composition of claim 1 wherein A is oxazolyl.
5. The composition of claim 1 wherein A is isoxazolyl.
6. The composition of claim 1 wherein C is thienyl.
7. The composition of claim 1 wherein C is furanyl.
8. The composition of claim 1 wherein C is oxazolyl.
9. The composition of claim 1 wherein C is isoxazolyl.
10. The composition of claim 1 comprising a compound of Formula IVa or a salt thereof,

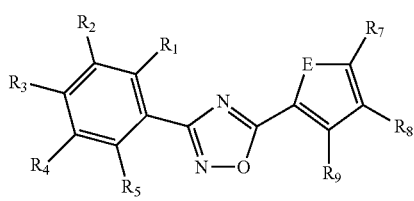

Formula IVa wherein $R_1$ and $R_5$ are independently selected from hydrogen, $CH_3$, F, Cl, Br, $CF_3$ and $OCF_3$;
$R_2$ and $R_4$ are independently selected from hydrogen, F, Cl, Br, and $CF_3$;
$R_3$ is selected from hydrogen, $CH_3$, $CF_3$, F, Cl, Br, $OCF_3$, $OCH_3$, CN, and C(H)O;
$R_7$ and $R_8$ are independently selected from hydrogen and fluorine;
$R_9$ is selected from hydrogen, F, Cl, $CH_3$, and $OCF_3$; and E is O or S.

11. The composition of claim 1 comprising a compound of Formula IVb or a salt thereof,

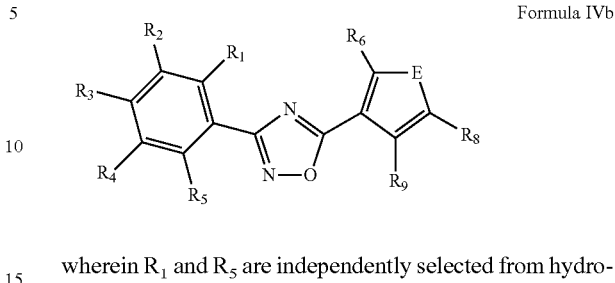

Formula IVb wherein $R_1$ and $R_5$ are independently selected from hydrogen, $CH_3$, F, Cl, Br, $CF_3$ and $OCF_3$;
$R_2$ and $R_4$ are independently selected from hydrogen, F, Cl, Br, and $CF_3$;
$R_3$ is selected from hydrogen, $CH_3$, $CF_3$, F, Cl, Br, $OCF_3$, $OCH_3$, CN, and C(H)O;
$R_8$ is selected from hydrogen and fluorine;
$R_6$ and $R_9$ are independently selected from hydrogen, F, Cl, $CH_3$, and $OCF_3$; and
E is O or S.

12. The composition of claim 1 comprising a compound of Formula Va or a salt thereof,

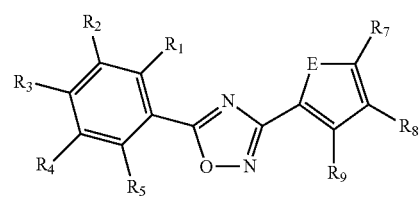

Formula Va wherein, $R_1$ and $R_5$ are independently selected from hydrogen, $CH_3$, F, Cl, Br, $CF_3$ and $OCF_3$;
$R_2$ and $R_4$ are independently selected from hydrogen, F, Cl, Br, and $CF_3$;
$R_3$ is selected from hydrogen, $CH_3$, $CF_3$, F, Cl, Br, $OCF_3$, $OCH_3$, CN, and C(H)O;
$R_7$ and $R_8$ are independently selected from hydrogen and fluorine;
$R_9$ is selected from hydrogen, F, Cl, $CH_3$, and $OCF_3$;
and E is O or S.

13. The composition of claim 1 comprising a compound of Formula Vb or a salt thereof,

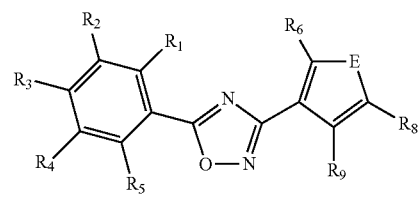

Formula Vb wherein $R_1$ and $R_5$ are independently selected from hydrogen, $CH_3$, F, Cl, Br, $CF_3$ and $OCF_3$;
$R_2$ and $R_4$ are independently selected from hydrogen, F, Cl, Br, and $CF_3$;

$R_3$ is selected from hydrogen, $CH_3$, $CF_3$, F, Cl, Br, $OCF_3$, $OCH_3$, CN, and C(H)O;

$R_8$ is selected from hydrogen and fluorine;

$R_6$ and $R_9$ are independently selected from hydrogen, F, Cl, $CH_3$, and $OCF_3$; and E is O or S.

14. The composition of claim 10 wherein E is O.

15. The composition of claim 10 wherein E is S.

16. The composition of claim 1 comprising a compound selected from the group consisting of:

3-phenyl-5-(thiophen-2-yl)-1,2,4-oxadiazole,
5-(furan-2-yl)-3-phenyl-1,2,4-oxadiazole,
3-(4-fluorophenyl)-5-(thiophen-2-yl)-1,2,4-oxadiazole,
3-(4-fluorophenyl)-5-(furan-2-yl)-1,2,4-oxadiazole,
3-(4-chlorophenyl)-5-(thiophen-2-yl)-1,2,4-oxadiazole,
3-(4-chlorophenyl)-5-(furan-2-yl)-1,2,4-oxadiazole,
3-(4-bromophenyl)-5-(thiophen-2-yl)-1,2,4-oxadiazole,
3-(4-bromophenyl)-5-(furan-2-yl)-1,2,4-oxadiazole,
3-(4-chloro-2-methylphenyl)-5-(furan-2-yl)-1,2,4-oxadiazole,
3-(2,4-dichlorophenyl)-5-(furan-2-yl)-1,2,4-oxadiazole,
3-(4-chlorophenyl)-5-(thiophen-3-yl)-1,2,4-oxadiazole,
3-(4-chlorophenyl)-5-(furan-3-yl)-1,2,4-oxadiazole,
3-(4-fluorophenyl)-5-(thiophen-3-yl)-1,2,4-oxadiazole, and
3-(4-fluorophenyl)-5-(furan-3-yl)-1,2,4-oxadiazole.

17. The composition of claim 16 comprising 3-phenyl-5-(thiophen-2-yl)-1,2,4-oxadiazole.

18. The composition of claim 1 further comprising water.

19. The composition of claim 1 in the form of a concentrate.

20. The composition of claim 1 further comprising a solvent in which the compound of Formula IV, Formula V, or a salt thereof is dissolved.

21. The composition of claim 20 further comprising a co-solvent.

22. The composition of claim 21 wherein the co-solvent is selected from the group consisting of ethyl lactate, methyl soyate, isopropanol, acetone, 1,2-propanediol, n-alkylpyrrolidone, petroleum-based oil and mineral oil.

23. The composition of claim 1 further comprising an aqueous surfactant.

24. The composition of claim 1 further comprising a permeation enhancer.

25. The composition of claim 16 comprising 5-(furan-2-yl)-3-phenyl-1,2,4-oxadiazole.

* * * * *